US011779563B2

(12) United States Patent
Rudnic et al.

(10) Patent No.: US 11,779,563 B2
(45) Date of Patent: Oct. 10, 2023

(54) ORAL CANNABINOID PHARMACEUTICAL COMPOSITIONS AND METHODS OF TREATING SLEEP DISORDERS

(71) Applicant: Curio IP, LLC, Towson, MD (US)

(72) Inventors: Edward M. Rudnic, Georgetown, TX (US); Michael Bronfein, Palm Beach Gardens, FL (US)

(73) Assignee: Curio IP, LLC, Towson, MD (US)

( * ) Notice: Subject to any disclaimer, the term of this patent is extended or adjusted under 35 U.S.C. 154(b) by 0 days.

(21) Appl. No.: 18/297,973

(22) Filed: Apr. 10, 2023

(65) Prior Publication Data

US 2023/0248693 A1 Aug. 10, 2023

Related U.S. Application Data

(62) Division of application No. 17/586,119, filed on Jan. 27, 2022, now Pat. No. 11,654,130.

(60) Provisional application No. 63/143,320, filed on Jan. 29, 2021.

(51) Int. Cl.
| | |
|---|---|
| *A61K 31/352* | (2006.01) |
| *A61P 25/20* | (2006.01) |
| *A61K 9/00* | (2006.01) |
| *A61K 9/20* | (2006.01) |
| *A61K 47/02* | (2006.01) |
| *A61K 47/12* | (2006.01) |
| *A61K 47/32* | (2006.01) |
| *A61K 47/38* | (2006.01) |

(52) U.S. Cl.
CPC .......... *A61K 31/352* (2013.01); *A61K 9/0053* (2013.01); *A61K 9/2095* (2013.01); *A61K 47/02* (2013.01); *A61K 47/12* (2013.01); *A61K 47/32* (2013.01); *A61K 47/38* (2013.01); *A61P 25/20* (2018.01)

(58) Field of Classification Search
CPC .................................................. A61K 31/352
See application file for complete search history.

(56) References Cited

U.S. PATENT DOCUMENTS

| | | | | |
|---|---|---|---|---|
| 11,654,130 B2 * | 5/2023 | Rudnic | ................... | A61K 47/12 514/454 |
| 2020/0281890 A1 | 9/2020 | Macnair et al. | | |

FOREIGN PATENT DOCUMENTS

| | | |
|---|---|---|
| WO | 2011/063164 | 5/2011 |
| WO | 2015/025312 | 2/2015 |
| WO | 2018/165740 | 2/2015 |
| WO | 2019/082171 | 5/2019 |
| WO | 2019/082181 | 5/2019 |

OTHER PUBLICATIONS

International Search Report and Written Opinion for PCT Patent Application No. PCT/US2022/014063, dated May 17, 2022; 14 pages.
Altman, Brianna R., et al. "Cannabis expectancies for sleep." Journal of psychoactive drugs 51.5 (2019): 405-412.
Babson, Kimberly A., James Sottile, and Danielle Morabito. "Cannabis, cannabinoids, and sleep: a review of the literature." Current psychiatry reports 19.4 (2017): 1-12.
Barratt, Ernest S., Wes Beaver, and Robert White. "The effects of marijuana on human sleep patterns." Biological Psychiatry (1974).
Bowles, Nicole P., Maya X. Herzig, and Steven A. Shea. "Recent legalization of cannabis use: effects on sleep, health, and workplace safety." Nature and science of sleep 9 (2017): 249.
Chait, L. D. "Subjective and behavioral effects of marijuana the morning after smoking." Psychopharmacology 100.3 (1990): 328-333.
Watson et al., Consensus Conference Panel:, et al. "Joint consensus statement of the American Academy of Sleep Medicine and Sleep Research Society on the recommended amount of sleep for a healthy adult: methodology and discussion." *Journal of Clinical Sleep Medicine* 11.8 (2015): 931-952.
Cousens, Kenneth, and Alberto DiMascio. "(—) Delta 9 THC as an hypnotic." Psychopharmacologia 33.4 (1973): 355-364.
Dance, S. (Mar. 24, 2020). Even without 'shelter in place' order, Maryland faces some of nation's strictest orders to contain coronavirus. The Baltimore Sun. Retrieved from https://www.baltimoresun.com/coronavirus/bs-md-shelter-in-place-order-20200324-43irmfpnzbee3d5mz23acqkuaa-story.html.
Edinger et al., 2004, Derivation of Research Diagnostic Criteria for Insomnia: Report of an American Academy of Sleep Medicine Work Group, SLEEP, vol. 27, No. 8, 2004, pp. 1567-1596.
Feinberg, Irwin, et al. "Effects of high dosage delta-9-tetrahydrocannabinol on sleep patterns in man." Clinical Pharmacology & Therapeutics 17.4 (1975): 458-466.
Gates, Peter J., Lucy Albertella, and Jan Copeland. "The effects of cannabinoid administration on sleep: a systematic review of human studies." Sleep medicine reviews 18.6 (2014): 477-487.
Huestis, Marilyn A. "Human cannabinoid pharmacokinetics." *Chemistry & biodiversity* 4.8 (2007): 1770.
Kessler, Ronald C., et al. "Insomnia and the performance of US workers: results from the America insomnia survey." Sleep 34.9 (2011): 1161-1171.
Laugsand, Lars Erik, et al. "Insomnia symptoms and risk for unintentional fatal injuries—the HUNT study." Sleep 37.11 (2014): 1777-1786.
Liu, Yong, et al. "Prevalence of healthy sleep duration among adults—United States, 2014." Morbidity and Mortality Weekly Report 65.6 (2016): 137-141.
National Conference of State Legislatures. (Mar. 10, 2020). State Medical Marijuana Laws. http://www.ncsl.org/research/health/state-medical-marijuana-laws.aspx.
National Sleep Foundation What is Insomnia? https://www.sleepfoundation.org/insomnia/what-insomnia, Accessed 2019.

(Continued)

*Primary Examiner* — Nizal S Chandrakumar
(74) *Attorney, Agent, or Firm* — McDermott Will & Emery

(57) ABSTRACT

Oral cannabinoid pharmaceutical compositions and methods of treating sleep disorders using the oral cannabinoid pharmaceutical compositions are described.

40 Claims, 22 Drawing Sheets

(56) References Cited

OTHER PUBLICATIONS

NHLBI (National Heart, Lung, and Blood Institute). National Sleep Disorders Research Plan, 2003. Bethesda, MD: National Institutes of Health; 2003.

Nicholson, Anthony N., et al. "Effect of A-9-tetrahydrocannabinol and cannabidiol on nocturnal sleep and early-morning behavior in young adults." *Journal of clinical psychopharmacology* 24.3 (2004): 305-313.

O'Hare, Emer, et al. "A comparison of radio-frequency biomotion sensors and actigraphy versus polysomnography for the assessment of sleep in normal subjects." *Sleep and Breathing* 19.1 (2015): 91-98.

Ogeil, Rowan P., et al. "Risky drug use and effects on sleep quality and daytime sleepiness." *Human Psychopharmacology: Clinical and Experimental* 30.5 (2015): 356-363.

Ohayon, Maurice M., et al. "Meta-analysis of quantitative sleep parameters from childhood to old age in healthy individuals: developing normative sleep values across the human lifespan." *Sleep* 27.7 (2004): 1255-1273.

Ohayon, Maurice, et al. "National Sleep Foundation's sleep quality recommendations: first report." *Sleep health* 3.1 (2017): 6-19.

Piper, Brian J., et al. "Substitution of medical cannabis for pharmaceutical agents for pain, anxiety, and sleep." *Journal of Psychopharmacology* 31.5 (2017): 569-575.

Pivik, R. T., et al. "Delta-9-tetrahydrocannabinol and synhexl: Effects on human sleep patterns." *Clinical Pharmacology & Therapeutics* 13.3 (1972): 426-435.

Russo, Ethan B. "Taming THC: potential cannabis synergy and phytocannabinoid-terpenoid entourage effects." *British journal of pharmacology* 163.7 (2011): 1344-1364.

Schade, Margeaux M., et al. "Sleep validity of a non-contact bedside movement and respiration-sensing device." *Journal of Clinical Sleep Medicine* 15.7 (2019): 1051-1061.

SleepScore Labs. (Apr. 22, 2020). Are We Getting More Sleep During COVID-19 Restrictions? Effects of THC combined with CBN on staying asleep. https://www.sleepscore.com/category/trouble-staying-asleep/.

SleepScore Labs (Nov. 16, 2020) CBD and Sleep: Does CBD Help with Sleep?, https://www.sleepscore.com/blog/cbd-and-sleep/.

SleepScore Labs (Mar. 31, 2022) What You Should Know About Marijuana and Sleep, https://www.sleepscore.com/blog/marijuana-and-sleep/.

The American Academy of Sleep Medicine. Insomnia. https://aasm.org/resources/factsheets/insomnia.pdf, Accessed 2019.

Tringale, Rolando, and Claudia Jensen. "Cannabis and insomnia." *Depression* 4.12 (2011): 0-68.

Wenger, Y., & Wood, P., "Gov. Hogan issues stay-at-home order for Maryland to stop spread of the coronavirus," Retrieved from The Baltimore Sun, Mar. 30, 2020.

Yoshida, H., Usami, N., Ohishi, Y, Watanabe, K., Yamamoto, I., & Yoshimura, H. (1995). Yoshida, Hisatoshi, et al. "Synthesis and pharmacological effects in mice of halogenated cannabinol derivatives." Chemical and pharmaceutical bulletin 43.2 (1995): 335-337. cannabinol derivatives. Chemical and Pharmaceutical Bulletin, 43(2), 335-337. https://doi.org/10.1248/cpb.43.335.

Zaffaroni, Alberto, et al. "Non-contact estimation of sleep staging." *EMBEC & NBC 2017.* Springer, Singapore, 2017. 77-80.

Zaffaroni, Alberto, et al. "Sleep staging monitoring based on sonar smartphone technology." *2019 41st Annual International Conference of the IEEE Engineering in Medicine and Biology Society (EMBC).* IEEE, 2019.

Abyadeh, et al., "A proteomic View of Cellular and Molecular Effects of Cannabis," Biomolecules 2021, 11, 1411, at p. 2 of 17.

Jain, et al., "Recent technologies in pulsatile drug delivery systems," Biomatter 1:1, 57-65; Jul./Aug./Sep. 2011.

Atakan, Zerrin, "Cannabis, a complex plant: different compounds and different effects on indivisuals," Therapeutic Advances in Psychopharmacology (2012) 2(6) 241-254.

\* cited by examiner

|  | Pre Product Use (Baseline) | | | Product In Use | | | Post Product Use |
|---|---|---|---|---|---|---|---|
| Study Week | -1 | -2 | -3 | 1 | 2 | 3 | |
| SleepScore Max Measurement | ➔ | | | ➔ | | | |
| Product Use | | | | ➔ | | | |
| Brief Daily Questionnaire | ➔ | | | ➔ | | | |
| Sleep experience questionnaire | | | X | X | | X | X |

FIG. 3

|  | Pre-product use period (3 weeks) | Product use period (3 weeks) |
|---|---|---|
| SleepScore Max measurement |  |  |
| Use of product |  |  |
| Brief daily questionnaire |  |  |
| Sleep experience questionnaire |  |  |

FIG. 13

ORAL CANNABINOID PHARMACEUTICAL COMPOSITIONS AND METHODS OF TREATING SLEEP DISORDERS

RELATED APPLICATIONS

This application is a Divisional Application of U.S. patent application Ser. No. 17/586,119 filed Jan. 27, 2022, which claims the benefit of U.S. Provisional Application 63/143,320 filed Jan. 29, 2021, the contents of which are herein incorporated by reference in their entirety.

TECHNICAL FIELD

The present disclosure relates to oral cannabinoid pharmaceutical compositions and methods of treating sleep disorders using the oral cannabinoid pharmaceutical compositions.

BACKGROUND

The Centers for Disease Control and Prevention have declared insufficient sleep a public health problem. It is recommended that adults get at least 7 hours of sleep per night for optimal health and wellbeing (Watson et al., Sleep. 2015 Aug. 1; 38(8):1161-83). However, one-third of US adults report getting less than 7 hours of sleep per night and up to 70 million suffer from sleep disorders (Liu Y et al., Morb Mortal Wkly Rep. 2016 Feb. 19; 65(6):137-41; National Heart, Lung, and Blood Institute, National Sleep Disorders Research Plan, 2003. Bethesda, MD: National Institutes of Health; 2003). Insufficient sleep is associated with a plethora of adverse health conditions including diabetes, hypertension, heart disease, stroke, depression, obesity, impaired immune function and increased risk of death (Watson et al., Sleep. 2015 Aug. 1; 38(8):1161-83). Existing sleep aids can often be ineffective or only marginally effective, and some may have a profound deleterious impact on quality of sleep, in particular on REM sleep and deep sleep components of the sleep experience. However, development of improved sleep medications is challenging.

SUMMARY

According to a first aspect, the present disclosure relates provides an oral pulse-release dosage form, comprising a total daily dose of a first cannabinoid active pharmaceutical ingredient ($API_1$) and a total daily dose of a second cannabinoid API ($API_2$). The oral pulse-release dosage form comprises a first pulse-release component ($C_1$) comprising a first portion ($P_1$) of the first cannabinoid API ($API_1P_1$) and a first portion ($P_1$) of the second cannabinoid API ($API_2P_1$). The oral pulse-release dosage form also comprises at least a second pulse-release component ($C_2$) comprising a second portion ($P_2$) of the first cannabinoid API ($API_1P_2$) and a second portion ($P_2$) of the second cannabinoid API ($API_2P_2$). The total daily dose of each of the $API_1$ and the $API_2$ is divided between the first portion ($P_1$) in the first pulse-release component ($C_1$) and at least the second portion ($P_2$) in the at least second pulse-release component ($C_2$). When the pulse-release dosage form is placed in an aqueous solution of 0.1N HCl pH 1.1 for 2 hours followed by 8 hours in sodium phosphate buffer at pH 6.8, at 37° C.±0.5° C., the pulse-release dosage form provides release of the $API_1P_2$ and the $API_2P_2$ beginning from 2 to 6 hours after release of the $API_1P_1$ and the $API_2P_1$ begins.

The oral pulse-release dosage form may include the following details, which can be combined with one another in any combinations unless clearly mutually exclusive:

The pulse-release dosage form may provide a second time of peak release rate ($PRR_2$) of each of the $API_1$ ($PRR_2API_1$) and the $API_2$ ($PRR_2API_2$) from about 2 to 6 hours after a first time of PRR ($PRR_1$).

The $PRR_1$ may be after 1-2 hours.

The first cannabinoid $API_1$ may be delta-9-tetrahydrocannabinol (THC) and the second cannabinoid $API_2$ may be cannabinol (CBN). The total daily dose of the THC may be from 1 mg to 40 mg and the total daily dose of the CBN may be from 2.5 mg to 100 mg.

The first cannabinoid $API_1$ may be THC and the second cannabinoid $API_2$ may be CBN. The total daily dose of the THC may be selected from: at least 1 mg, at least 2 mg, at least 3 mg, at least 4 mg, at least 5 mg, at least 6 mg, at least 8 mg, at least 10 mg, at least 15 mg, at least 20 mg, at least 25 mg, at least 30 mg, and at least 35 mg, and the total daily dose of the CBN may be selected from: at least 2.5 mg, at least 3 mg, at least 4 mg, at least 5 mg, at least 15 mg, at least 20 mg, at least 25 mg, at least 30 mg, at least 35 mg, and at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

The first pulse-release component ($C_1$) may be an immediate release (IR) formulation of the first cannabinoid $API_1$ and the second cannabinoid $API_2$, comprising: the first portion ($P_1$) of the first cannabinoid API ($API_1P_1$) and a first portion ($P_1$) of the second cannabinoid API ($API_2P_1$), and one or more binders, one or more disintegrants, one or more lubricants, one or more flow aids, or any combinations thereof. The second pulse-release component ($C_2$) may be a delayed release (DR) formulation of the first cannabinoid APIs and the second cannabinoid $API_2$, comprising: the second portion ($P_2$) of the first cannabinoid API ($API_1P_2$) and a second portion ($P_2$) of the second cannabinoid API ($API_2P_2$), and one or more binders, one or more lubricants, one or more flow aids, or any combinations thereof. The second pulse-release component may be coated with a delayed-release layer comprising one or more pH-dependent and/or non-pH-dependent polymers, and optionally one or more plasticizers, one or more pore formers, or one or more lubricants, or any combinations thereof.

For each API, the first portion ($P_1$) may be independently selected from 25% to 75% of the total daily dose, and for each API the second portion ($P_2$) may be independently selected from 25% to 75% of the total daily dose.

In the first pulse-release component ($C_1$), the second pulse-release component ($C_2$), or both, when present: the binders may comprise from 1 to 60% (w/w), the disintegrants may comprise from 0.05 to 15% (w/w), the lubricants may comprise from 0.5 to 5% (w/w), the flow aids may comprise from 0.05 to 0.5% (w/w), and the pH-dependent and/or non-pH-dependent polymers may comprise from 0.5 to 35% (w/w).

The first pulse-release component ($C_1$) may comprise from 0.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The first pulse-release component ($C_1$) may comprise microcrystalline cellulose, hydroxypropylmethylcellulose, and magnesium stearate. The second pulse-release component ($C_2$) may comprise from 0.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The second pulse-release component ($C_2$) may comprise microcrystalline cellulose, methacrylic acid copolymer, magnesium stearate, and colloidal silicone dioxide.

According to a second aspect, the present disclosure relates provides an oral pulse-release dosage form, comprising a total daily dose of a first cannabinoid active pharmaceutical ingredient ($API_1$) and a total daily dose of a second cannabinoid API ($API_2$). The pulse-release dosage form comprises a first pulse-release component ($C_1$) comprising a first portion ($P_1$) of the first cannabinoid API ($API_1P_1$) and a first portion ($P_1$) of the second cannabinoid API ($API_2P_1$), a second pulse-release component ($C_2$) comprising a second portion ($P_2$) of the first cannabinoid API ($API_1P_2$) and a second portion ($P_2$) of the second cannabinoid API ($API_2P_2$), and at least a third pulse-release component ($C_3$) comprising a third portion ($P_3$) of the first cannabinoid API ($API_1P_3$) and a third portion ($P_3$) of the second cannabinoid API ($API_2P_2$). The total daily dose of each of the APIs and the $API_2$ may be divided between the first portion ($P_1$) in the first pulse-release component ($C_1$), the second portion ($P_2$) in the second pulse-release component ($C_2$), and at least the third portion ($P_3$) in the at least third pulse-release component ($C_3$). When the pulse-release dosage form is placed in an aqueous solution of 0.1N HCl pH 1.1 for 2 hours followed by 8 hours in sodium phosphate buffer at pH 6.8, at 37° C.±0.5° C., the pulse-release dosage form provides release of the $API_1P_2$ and the $API_2P_2$ beginning from 1 to 4 hours after release of the $API_1P_1$ and the $API_2P_1$ begins, and release of the $API_1P_3$ and the $API_2P_3$ beginning from 1 to 4 hours after release of the $API_1P_2$ and the $API_2P_2$ begins.

The oral pulse-release dosage form may include the following details, which can be combined with one another in any combinations unless clearly mutually exclusive:

The pulse-release dosage form may provide a second time of peak release rate ($PRR_2$) of each of the $API_1$ ($PRR_2API_1$) and the $API_2$ ($PRR_2API_2$) from about 1 to 4 hours after a first time of PRR ($PRR_1$) and a third time of peak release rate ($PRR_3$) of each of the $API_1$ ($PRR_3API_1$) and the $API_2$ ($PRR_3API_2$) from about 1 to 4 hours after the second time of PRR ($PRR_2$).

The $PRR_1$ may be after 1-2 hours.

The first cannabinoid $API_1$ may be delta-9-tetrahydrocannabinol (THC) and the second cannabinoid $API_2$ may be cannabinol (CBN). The total daily dose of the THC may be from 10 mg to 40 mg and the total daily dose of the CBN may be from 5 mg to 100 mg.

The first cannabinoid $API_1$ may be THC and the second cannabinoid $API_2$ may be CBN, and the total daily dose of the THC may be selected from: at least 10 mg, at least 15 mg, at least 20 mg, at least 25 mg, at least 30 mg, and at least 35 mg, and the total daily dose of the CBN may be selected from: at least 5 mg, at least 10 mg, at least 15 mg, at least 20 mg, at least 25 mg, at least 30 mg, at least 35 mg, and at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

The first pulse-release component ($C_1$) may be an immediate release (IR) formulation of the first cannabinoid $API_1$ and the second cannabinoid $API_2$, comprising the first portion ($P_1$) of the first cannabinoid API ($API_1P_1$) and a first portion ($P_1$) of the second cannabinoid API ($API_2P_1$). The first pulse-release component ($C_1$) may comprise one or more binders, one or more disintegrants, one or more lubricants, one or more flow aids, or any combinations thereof. The second pulse-release component ($C_2$) may be a delayed release (DR) formulation of the first cannabinoid APIs and the second cannabinoid $API_2$, comprising the second portion ($P_2$) of the first cannabinoid API ($API_1P_2$) and a second portion ($P_2$) of the second cannabinoid API ($API_2P_2$). The second pulse-release component ($C_2$) may comprise one or more binders, one or more lubricants, one or more flow aids, or any combinations thereof. The second pulse-release component may be coated with a first delayed-release layer comprising one or more pH-dependent and/or non-pH-dependent polymers, and optionally one or more plasticizers, one or more pore formers, one or lubricants, or any combinations thereof. The third pulse-release component ($C_3$) may be a delayed release (DR) formulation of the first cannabinoid $API_1$ and the second cannabinoid $API_2$, comprising the third portion ($P_3$) of the first cannabinoid API ($API_1P_3$) and a third portion ($P_3$) of the second cannabinoid API ($API_2P_3$). The third pulse-release component ($C_3$) may comprise one or more binders, one or more lubricants, one or more flow aids, or any combinations thereof. The third pulse-release component may be coated with a second delayed-release layer comprising one or more pH-dependent and/or non-pH-dependent polymers, and optionally one or more plasticizers, one or more pore formers, one or lubricants, or any combinations thereof.

For each API, the first portion ($P_1$) may be independently selected from 25% to 75% of the total daily dose, for each API, the second portion ($P_2$) may be independently selected from 25% to 75% of the total daily dose, and, for each API, the third portion ($P_3$) may be independently selected from 25% to 75% of the total daily dose.

In the first pulse-release component ($C_1$), the second pulse-release component ($C_2$), and/or the third pulse-release component ($C_3$), when present: the binders may comprise from 1 to 60% (w/w), the disintegrants may comprise from 0.05 to 15% (w/w), the lubricants may comprise from 0.5 to 5% (w/w), the flow aids may comprise from 0.05 to 0.5% (w/w), and the pH-dependent and/or non-pH-dependent polymers may comprise from 0.5 to 35% (w/w).

The first pulse-release component ($C_1$) may comprise from 2.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The first pulse-release component ($C_1$) may comprise microcrystalline cellulose, hydroxypropylmethylcellulose, croscormellose sodium, magnesium stearate, or any combinations thereof. The second pulse-release component ($C_2$) may comprise from 2.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The second pulse-release component ($C_2$) may comprise microcrystalline cellulose, cellulose acetate phthalate, magnesium stearate, or any combinations thereof. The third pulse-release component ($C_3$) may comprise from 2.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The third pulse-release component ($C_3$) may comprise microcrystalline cellulose, methacrylic acid copolymer, magnesium stearate, or any combinations thereof.

According to a third aspect, the present disclosure provides a method of treating a sleep disorder in a subject in need thereof, the method comprising: administering to the subject an oral pulse-release dosage form described herein.

The method may include the following details, which can be combined with one another in any combinations unless clearly mutually exclusive:

The administering may result in an increase in the subject's total sleeping time during the night.

The administering may result in an increase in the subject's total light sleeping time during the night.

The administering may result in an increase in the subject's light sleeping time as a proportion of total sleeping time during the night.

The administering may result in an increase in the subject's total time in bed during the night.

The increase may be measured using a SleepScore Max® system.

The administering may result in an increase in SleepScore number as determined using a SleepScore Max® system.

The administering may result in the subject experiencing an increase in one or more of: feeling well rested in the morning and/or during the day, perceived sleep quality, perceived total sleep time during the night, or sleep satisfaction. Additionally or alternatively, the subject may experience a decrease in one or more of: perceived frequency of awakenings during the night, number of times out of bed at night, number of naps during the day, or perceived time awake at night.

The sleep disorder may comprise insomnia, wherein the insomnia is primarily characterized by an inability to stay asleep during the night.

The insomnia may be characterized using a SleepScore Max® system.

Characterization of the sleep disorder may be reported by the subject.

The administering may not result in a decrease in latency to sleep onset, an alteration of time in deep sleep and/or REM sleep, a hangover effect during the day after the administering, or any combinations thereof.

The subject may have previously been administered with one or more cannabinoids for treating a medical condition.

The administering may be up to 30 minutes, 1 hour, or 2 hours before the subject intends to begin sleeping at night.

BRIEF DESCRIPTION OF THE DRAWINGS

The present disclosure may be further understood through reference to the attached figures in combination with the detailed description that follows.

FIG. 3 is a schematic showing an example clinical study timeline.

FIG. 13 is a schematic showing an example clinical study timeline.

DETAILED DESCRIPTION

Figure 1:
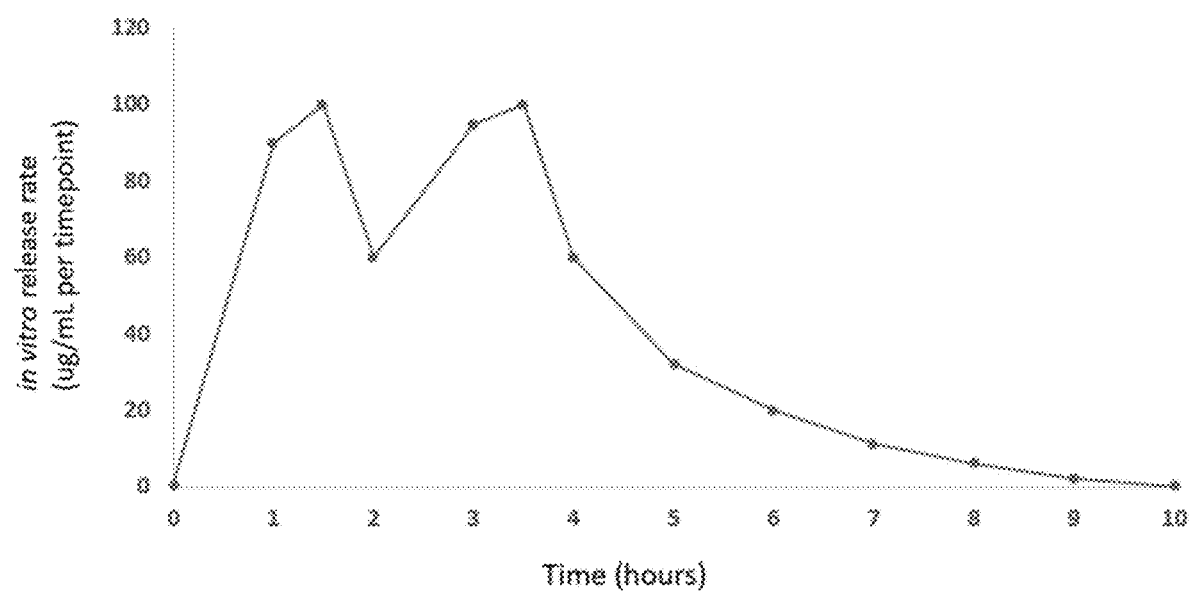
FIG. 1 is a graph reporting an example in vitro dissolution release rate (μg/mL per timepoint) of delta-9 Tetrahydrocannabinol (THC) versus time in hours of an example 2-pulse oral pharmaceutical composition tablet.

Insomnia, defined as difficulty falling asleep or staying asleep, is the most common sleep disorder with approximately 30% of adults having symptoms each year (National Sleep Foundation. What is Insomnia? https://www.sleepfoundation.org/insomnia/what-insomnia, Accessed 2019; The American Academy of Sleep Medicine. Insomnia. https://aasm.org/resources/factsheets/insomnia.pdf, Accessed 2019.). It is a major contributing factor to motor vehicle deaths, and loss of productivity, due to insomnia, costs the US workforce $63.2 billion annually (The American Academy of Sleep Medicine. Insomnia. https://aasm.org/resources/factsheets/insomnia.pdf, Accessed 2019; Laugsand L E, Strand L B, Vatten L J, et. al. Insomnia Symptoms and Risk for Unintentional Fatal Injuries—The HUNT Study. Sleep. 2014 Nov. 1; 37(11):1777-86; Kessler R C, Berglund P A, Coulouvrat C, et al. Insomnia and the performance of US workers: results from the America insomnia survey. Sleep. 2011 Sep. 1; 34(9):1161-71). A number of sleep medications are available to improve sleep quality including prescription drugs, over-the-counter medication and alternative treatments. Of the alternative solutions available, *Cannabis* has received increased attention over the last two decades with the legalization of medical *Cannabis* in 33 states and Washington DC (National conference of state legislatures, State Medical Marijuana Laws. http://www.ncsl.org/research/health/state-medical-marijuana-laws.aspx, Accessed 2019). According to recent studies, two-thirds of medical *Cannabis* users have reduced their sleep medication use since starting medical *Cannabis*, and they expect medical *Cannabis* to improve their sleep quality (Piper B J, DeKeuster R M, Beals M L, et al. Substitution of medical *Cannabis* for pharmaceutical agents for pain, anxiety and sleep. J Psychopharmacol. 2017 May; 31(5):569-575; Altman B R, Mian M N, Slavin M, Earleywine M. *Cannabis* Expectancies for Sleep. J Psychoactive Drugs. 2019 Jul. 18:1-8.). To date, the impact of cannabinoids on sleep is unclear.

Delta-9 Tetrahydrocannabinol (THC) is one of the most widely studied cannabinoids on sleep, yet its effects are not well understood (Babson K A, Sottile J, Morabito D. *Cannabis*, Cannabinoids, and Sleep: A Review of the Literature. Curr Psychiatry Rep. 2017 April; 19(4):23; Gates P J, Albertella L, Copeland J. The effects of cannabinoid administration on sleep: a systematic review of human studies. Sleep Med Rev. 2014 December; 18(6):477-87.). Early studies focused on the connection between THC and polysomnography. Cousens and DiMascio showed that THC significantly decreased time to fall asleep yet it causes a hangover effect, defined as continued effects of a cannabinoid drug felt by the subject during the following day (Cousens K, DiMascio A. (−) Delta 9 THC as a hypnotic. An experimental study of three dose levels. Psychopharmacologia. 1973 Dec. 20; 33(4):355-64.). Conversely, Chait reported that THC is not associated with a hangover effect (Chait L D. Subjective and behavioral effects of marijuana the morning after smoking. Psychopharmacology (Berl). 1990; 100(3):328-33.). Other polysomnography studies suggested that THC reduces the duration of REM sleep and may increase the duration of Stage 4 sleep (Feinberg I, Jones R, Walker J M, et al. Effects of high dosage delta-9-tetrahydrocannabinol on sleep patterns in man. Clin Pharmacol Ther. 1975 April; 17(4):458-66; Pivik R T, Zarcone V, Dement W C, Hollister L E. Delta-9-tetrahydrocannabinol and synhexl: effects on human sleep patterns. Clin Pharmacol Ther. 1972 May-June; 13(3):426-35.). Recent studies focusing on self-reported sleep quality are also inconsistent. A few studies have shown that THC is sedative and reduces sleep onset latency while many have found an association between THC and poor sleep quality (Nicholson A N, Turner C, Stone B M, Robson P J. Effect of delta 9 THC and Cannabidiol on Nocturnal Sleep and Early-morning Behavior in Young Adults. J Clin Psychopharmacol. 2004 June; 24(3):305-13; Tringale R, Jensen C. *Cannabis* and insomnia. Depression. 2011; 4(12):0-68; Ogeil R P, Phillips J G, Rajaratnam S M, Broadbear J H. Risky drug use and effects on sleep quality and daytime sleepiness. Hum Psychopharmacol. 2015 September; 30(5):356-63.). Ultimately, in previous studies, the optimal THC concentration, route of administration and administration time needed to positively impact sleep quality has not been determined (Watson N F, Badr M S, Belenky G, et al.; Consensus Conference Panel. Joint consensus statement of the American Academy of Sleep Medicine and Sleep Research Society on the recommended amount of sleep for a healthy adult: methodology and discussion. Sleep. 2015 Aug. 1; 38(8):1161-83.).

The present disclosure relates to oral cannabinoid pharmaceutical compositions and methods of treating sleep disorders using the oral cannabinoid pharmaceutical compositions.

A. Active Pharmaceutical Ingredients (API's)

In some embodiments, an API of the present disclosure can be a cannabinoid. The term "cannabinoid" as used herein refers to several classes of compounds that can be found in plants of the genus *Cannabis*. There are at least 144 different cannabinoids that have been isolated from *Cannabis*, exhibiting varied effects. Synthetic encompass a variety of distinct chemical classes: the classical cannabinoids structurally related to THC, the nonclassical cannabinoids (cannabimimetics) including the aminoalkylindoles, 1,5-diarylpyrazoles, quinolines, and arylsulfonamides as well as eicosanoids related to endocannabinoids.

The classical cannabinoids are concentrated in a viscous resin of *Cannabis* plants produced in structures known as glandular trichomes. The main classes of cannabinoids include, without limitation, THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCC (tetrahydrocannabiorcol), THCV (tetrahydrocannabivarin), THCP (tetrahydrocannabiphorol), CBDV (cannabidivarin), CBCV (cannabichromevarin), CBGV (cannabigerovarin), CBGM (cannabigerol monomethyl ether), CBE (cannabielsoin), and CBT (cannabicitran). Cannabinoids of the present disclosure include, without limitation: Cannabigerol-type (CBG) cannabinoids, such as Cannabigerol monomethyl ether, Cannabinerolic acid A, Cannabigerovarin, Cannabigerolic acid A, Cannabigerolic acid A monomethyl ether, and Cannabigerovarinic acid A; Cannabichromene-type (CBC) cannabinoids, such as (±)-Cannabichromene, (±)-Cannabichromenic acid A, (±)-Cannabivarichromene, (±)-Cannabichromevarin, and (±)-Cannabichromevarinic acid A; Cannabidiol-type (CBD) cannabinoids, such as (−)-Cannabidiol, Cannabidiol momomethyl ether, Cannabidiol-$C_4$, (−)-Cannabidivarin, Cannabidiorcol, Cannabidiolic acid, and Cannabidivarinic acid; Cannabinodiol-type (CBND) cannabinoids, such as Cannabinodiol and Cannabinodivarin; Tetrahydrocannabinol-type (THC) cannabinoids, such as $\Delta^9$-Tetrahydrocannabinol, $\Delta^9$-Tetrahydrocannabinol-$C_4$, $\Delta^9$-Tetrahydrocannabivarin, $\Delta^9$-Tetrahydrocannabiorcol, $\Delta^9$-Tetrahydrocannabinolic acid A, $\Delta^9$-Tetrahydro-cannabinolic acid B, $\Delta^9$-Tetrahydro-cannabinolic acid-$C_4$ A and/or B, $\Delta^9$-Tetrahydro-cannabivarinic acid A, $\Delta^9$-Tetrahydro-cannabiorcolic acid A and/or B, (−)-$\Delta^8$-trans-(6aR,10aR)-$\Delta^8$-Tetrahydrocannabinol, (−)-$\Delta^8$-trans-(6aR,10aR)-Tetrahydrocannabinolic acid A, and (−)-(6aS,10aR)-$\Delta^9$-Tetrahydrocannabinol; Cannabinol-type (CBN) cannabinoids, such as Cannabinol, Cannabinol-$C_4$, Cannabivarin, Cannabinol-$C_2$, Cannabiorcol, Cannabinolic acid A, and Cannabinol methyl ether; Cannabitriol-type (CBT) cannabinoids, such as (−)-(9R,10R)-trans-Cannabitriol, (+)-(9S,10S)-Cannabitriol, (±)-(9R,10S/9S,10R)-Cannabitriol, (−)-(9R,10R)-trans-10-O-Ethyl-cannabitriol, (±)-(9R,10R/9S,10S)-Cannabitriol-$C_3$, 8,9-Dihydroxy-$\Delta^{6a(10a)}$-tetrahydrocannabinol, Cannabidiolic acid A cannabitriol ester, (−)-(6aR,9S,10S,10aR)-9,10-Dihydroxy-hexahydrocannabinol, Cannabiripsol, (−)-6a,7, 10a-Trihydroxy-$\Delta^9$-tetrahydrocannabinol, 10-Oxo-$\Delta^{6a(10a)}$-tetrahydrocannabinol; Cannabielsoin-type (CBE) cannabinoids such as (5aS,6S,9R,9aR)-Cannabielsoin, (5aS,6S,9R,9aR)-$C_3$-Cannabielsoin, (5aS,6S,9R,9aR)-Cannabielsoic acid A, (5aS,6S,9R,9aR)-Cannabielsoic acid B, (5aS,6S,9R,9aR)-$C_3$-Cannabielsoic acid B, Cannabiglendol-$C_3$, Dehydrocannabifuran, and Cannabifuran; Isocannabinoids such as (−)-$\Delta^7$-trans-(1R,3R,6R)-Isotetrahydrocannabinol, (±)-$\Delta^7$-1,2-cis-(1R,3R,6S/1S,3S,6R)-Isotetrahydrocannabivarin, and (−)-$\Delta^7$-trans-(1R,3R,6R)-Isotetrahydrocannabivarin; Cannabicyclol-type (CBL) cannabinoids such as (±)-(1aS,3aR,8bR,8cR)-Cannabicyclol, (±)-(1aS,3aR,8bR,8cR)-Cannabicyclolic acid A, and (±)-(1aS,3aR,8bR,8cR)-Cannabicyclovarin; Cannabicitran-type (CBT) cannabinoids such as Cannabicitran; and Cannabichromanone-type (CBCN) cannabinoids such as Cannabichromanone, Cannabichromanone-$C_3$, and Cannabicoumaronone.

In some embodiments, the term "cannabinoid" as used herein refers to compounds that may be extracted from, and/or derived from *Cannabis* plants using methods known in the art. For example, cannabinoids can be separated from the *Cannabis* plant by extraction with organic solvents or using supercritical solvent extraction with carbon dioxide. Cannabinoids may be obtained in oils extracted from *Cannabis* plants, and thereafter further isolated, purified, and converted into derivatives. In some embodiments, the term "cannabinoid" as used herein may also refer to such compounds that may be produced synthetically or using recombinant biotechnology methods, as may be identified by persons of ordinary skill in the art.

Cannabinoids of the present disclosure may include stereoisomers thereof, and modified forms thereof, such as a pharmaceutically acceptable salt, ester, derivative, analog, prodrug, hydrate, or solvate thereof.

In some embodiments, a pharmaceutical compositions of the present disclosure can include, without limitation, one or more cannabinoids, two or more cannabinoids, or three or more cannabinoids. In some embodiments, the cannabinoid may be THC, CBN, CBD, or any combinations thereof.

The best studied cannabinoids include tetrahydrocannabinol (THC), cannabidiol (CBD) and cannabinol (CBN). $\Delta^9$-tetrahydrocannabinol ($\Delta^9$-THC or THC), is also known by its International Non-Proprietary Name (INN) as dronabinol. The unsaturated bond in the cyclohexene ring is located between C-9 and C-10 in the more common dibenzopyran ring numbering system. There are four stereoisomers of THC, but only the (−)-trans isomer occurs naturally (CAS-1972-08-03). The fully systematic name for this THC isomer is (−)-(6aR,10aR)-6,6,9-trimethyl-3-pentyl-6a,7,8,10a-tetrahydro-6H-benzo[c]chromen-1-ol. Two related substances, $\Delta^9$-tetrahydrocannabinol-2-oic acid and $\Delta^9$-tetrahydrocannabinol-4-oic acid (THCA), are also present in *Cannabis*, sometimes in large amounts. During smoking, THCA is partly converted to THC. The active isomer $\Delta^8$-THC, in which the unsaturated bond in the cyclohexene ring is located between C-8 and C-9, is found in much smaller amounts. Other closely related substances that occur in *Cannabis* include cannabidiol (CBD) and, in aged samples, cannabinol (CBN), both of which have quite different pharmacological effects to THC.

THC is the most known active component of *Cannabis*. The pharmacology of *Cannabis* is complicated by the presence of a wide range of cannabinoids. At small doses, *Cannabis* produces euphoria, relief of anxiety, sedation and drowsiness. In some respects, the effects are similar to those caused by alcohol. Anandamide has been identified as the endogenous ligand for the cannabinoid receptor and has pharmacological properties similar to those of THC. When *Cannabis* is smoked, THC can be detected in plasma within seconds of inhalation; it has a half-life of 2 hours. Following smoking of the equivalent of 10-15 mg over a period of 5-7 minutes, peak plasma levels of $\Delta^9$-THC are around 100 μg/L. It is highly lipophilic and widely distributed in the body. Two active metabolites are formed: 11-hydroxy-$\Delta^9$-THC and 8β-hydroxy-$\Delta^9$-THC. The first is further metabolized to $\Delta^9$-THC-11-oic acid. Two inactive substances are also formed—8α-hydroxy-$\Delta^9$-THC and 8α,11-dihydroxy-$\Delta^9$-THC—and many other minor metabolites, most of which appear in the urine and feces as glucuronide conjugates. Some metabolites can be detected in the urine for up to 2 weeks following smoking or ingestion.

Bioavailability following the smoking route was reported as 2-56%, due in part to intra- and inter-subject variability in smoking dynamics, which contributes to uncertainty in dose delivery. The number, duration, and spacing of puffs, hold time, and inhalation volume, or smoking topography, greatly influences the degree of drug exposure (Huestis M., "Human Cannabinoid Pharmacokinetics" Chem Biodivers. 2007 August; 4(8): 1770-1804).

The chemical structure of $\Delta^9$-THC may be represented as Formula I:

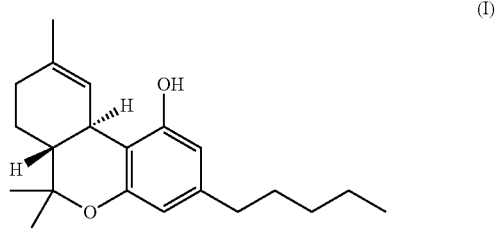 [SMILES: CCCCCc1cc(O)c2c(c1)OC(C)(C)[C@@H]1CCC(C)=C[C@@H]21]

(I)

The chemical structure of CBN may be represented as Formula II:

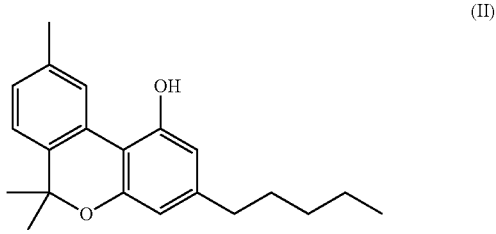 [SMILES: CCCCCc1cc(O)c2c(c1)OC(C)(C)c1ccc(C)cc1-2]

(II)

At least six CBN-type cannabinoids are known. With ring A aromatized, they may be formed as oxidation artifacts of THC and CBD, respectively. Their concentration in *Cannabis* products may depend on age and storage conditions. CBN has been shown to induce drowsiness, and reduced time to sleep, but has been shown to create "hangover" symptoms when used alone for sleep.

THC and CBN are known to be readily absorbed via the inhalation route, but very little is known about the biotransformation of CBN following oral administration and release in the gastrointestinal tract. Furthermore, to date, very little, if any, published information is available regarding the extent, or components of, biotransformation of cannabinoids, such as THC or CBN, following a delayed-release e.g. into the duodenum.

The pharmaceutical formulations described herein are provided to meet the need in the art for oral dosage forms that provide controlled release into the gastrointestinal tract of a subject, in order to provide delivery of cannabinoid APIs described herein that in some embodiments may be useful for treating sleep disorders.

B. Pharmaceutical Formulations

In some embodiments, the present disclosure provides oral pulse-release compositions and dosage forms thereof, comprising a dose, e.g. a total daily dose, of one or more cannabinoid active pharmaceutical ingredients.

The terms "pulse-release" or "pulsatile" formulation, as used herein refers in general to release of a portion of a total API dose, e.g. a portion of a total daily API dose, in a burst, followed by periods of little or no release (e.g., lag phase) in a defined temporal pattern. In particular, oral pulsatile drug release pertains to the burst delivery of drugs following a temporal pattern from the time of oral administration. In some embodiments, the pulse-release formulations of the present disclosure may combine a range of formulation approaches, including single- or multiple-unit immediate-release, delayed-release, and/or extended-release components. For example, in some embodiments, the delayed release components in the pulsatile formulations described herein may be configured to release an API at a desired site within the gastrointestinal tract, and/or release of the API after a defined time period. In some embodiments, an oral pulse-release dosage form of the present disclosure may comprise one or more immediate release oral pharmaceutical formulation components, one or more delayed release oral pharmaceutical formulation components, one or more extended release oral pharmaceutical formulation components, or any combinations thereof.

In some embodiments, when administered orally to a subject, an oral pulse-release dosage form of the present disclosure is configured to provide release of a dosage, e.g. a daily dosage, of the one or more cannabinoids into the gastrointestinal tract of the subject, divided into at least 2 separate releases, or pulses separated by at least 2 hours, and not more than 6 hours, between releases. In some embodiments, when administered orally to a subject, an oral pulse-release dosage form of the present disclosure is configured to provide release of a dosage, e.g. a daily dosage, of the one or more cannabinoids into the gastrointestinal tract of the subject, divided into at least 3 separate releases, or pulses separated by at least 1 hours, and not more than 4 hours, between releases.

In some embodiments, an oral pulse-release dosage form of the present disclosure may provide a total daily dose of a cannabinoid API, or a partial daily dose of a cannabinoid API. In some embodiment, a plurality, e.g. 2, 3, or more of the oral pulse-release dosage form of the present disclosure may be administered to a subject to provide a total daily dose. In some embodiments, the oral pulse-release dosage form of the present disclosure may be administered once, twice, three times or more, per day to provide a total daily dose of a cannabinoid API.

In some embodiments, the pulse-release dosage forms of the present disclosure are configured to release a portion of an API in the gastric region (e.g. in the stomach), and the remaining portion in the small intestine e.g. distal duodenum, or other distal sites in the gastrointestinal tract.

Accordingly, in some embodiments, the present disclosure provides an oral pulse-release dosage form, comprising a total dose, e.g. a total daily dose, of a cannabinoid active pharmaceutical ingredient (API), wherein the pulse-release dosage form comprises a first pulse-release component ($C_1$) comprising a first portion ($P_1$) of the cannabinoid API (API-$P_1$), and at least a second pulse-release component ($C_2$) comprising a second portion ($P_2$) of the first cannabinoid API (API$_1P_2$). In the oral pulse-release dosage form, the total dose, e.g. total daily dose, of the API is divided between the first portion ($P_1$) in the first pulse-release component ($C_1$) and at least the second portion ($P_2$) in the at least second pulse-release component ($C_2$). When the pulse-release dosage form is placed in a simulated gastrointestinal environment, the pulse-release dosage form provides release of the API-$P_2$ beginning from 2 to 6 hours after release of the API-$P_1$ begins.

The term "simulated gastrointestinal environment" is intended to be used herein to convey its ordinary meaning as understood in the art, and is understood in a broad sense to mean conditions that mimic oral administration, for example, an aqueous environment of low pH, 1-5 for example, followed after a period of up to about 2 hours with immersion in a higher pH aqueous environment, such as pH 6.8, for example, or a 3 stage environment in which the low pH is followed by an intermediate pH of about 6 wherein the environments are maintained at about 37.0° C. Alternatively, for certain embodiments a simulated gastrointestinal environment is described as the USP Apparatus I (Baskets) with agitation in which the composition is placed in 700 ml aqueous solution of 0.1N HCl pH 1.1, for up to 2 hours followed by 2-8 hours in sodium phosphate buffer at pH 6.0; followed by 6-20 hours in sodium phosphate buffer, pH 7.2, adding NaOH to adjust pH to 7.2. In some embodiments, the dissolution testing can include placing a dosage form in an aqueous solution of 0.1N HCl pH 1.1 for 2 hours followed by 8 hours in sodium phosphate buffer at pH 6.8, at 37° C.±0.5° C., and sampling at appropriate time intervals, e.g. at 1, 1.5, 2, 3, 3.5, 4, 5, 6, 7, 8, 9 and 10 hours.

For example, a two-stage dissolution test is described in USP General Chapter <711> Dissolution, in which the integrity of an enteric coating is determined in an acidic environment and the drug release is measured in a neutral environment. The test can be performed using either medium-addition or medium exchange methods; both may start with an acid stage in 0.1N hydrochloric acid for two hours and follow with a buffer stage in phosphate buffer at pH 6.8 for e.g. 45 min or a specific time as needed for the individual drug product. Medium addition or medium exchange procedures may be used. For the medium-addition approach, a designated amount of concentrated phosphate buffer may be added to the dissolution vessel to neutralize the medium to the target pH before the buffer stage starts. The operations of adding the buffer and adjusting the pH may be completed within 5 min. For the medium-exchange approach, the acid medium may be drained after two hours, and a full amount of pH 6.8 buffer may be added to the same vessel for the buffer stage. The dosage unit is typically left undisturbed during the medium change. Alternatively, the vessel containing the acid can be removed and replaced with another vessel containing the buffer, and the dosage unit transferred to the new vessel.

Parameters of suitable API-specific biorelevant dissolution methods such as in vitro dissolution analysis can be determined by skilled persons without undue experimentation upon reading the present disclosure. For example, and without limitation, an in-vitro non-sink, gastric transfer dissolution method may be used to analyze the release and dissolution of API.

At pre-determined time points, samples may be drawn from the dissolution vessel and centrifuged using an ultracentrifuge. The supernatants may be further diluted using an HPLC diluent and analyzed by a suitable HPLC method. Parameters such as peak release rate (PRR) and the area under drug dissolution curve (AUDC), among others, may be calculated, e.g. by the linear trapezoidal method.

Each of the pulse-release components that may be combined to provide the oral pulse-release dosage form may be analyzed separately by in vitro dissolution tests, to determine the pulse-release timing for each pulse-release component of the oral pulse-release dosage form. The "beginning" of release from a pulse-release component may be defined as the time at which a detectable amount of the API is present in the dissolution media, or when a certain percentage of the total dose is detected in the dissolution media, e.g. at least 1%, 5%, or 10% of the total amount of the API present in the particular pulse-release component.

For example, in some embodiments, the simulated gastrointestinal environment may be an aqueous solution of 0.1N HCl pH 1.1 for 2 hours followed by 8 hours in sodium phosphate buffer at pH 6.8, at 37° C.±0.5° C.

In some embodiments, when the pulse-release dosage form is placed in a simulated gastrointestinal environment, the pulse-release dosage form may provide a second time of peak release rate ($PRR_2$) of the API from about 2 to 6 hours after a first time of peak release rate ($PRR_1$). For example, FIG. 1 and Example 3 describe example in vitro dissolution data of an example pulse-release dosage form of the present disclosure. In some embodiments, when the pulse-release dosage form is placed in a simulated gastrointestinal environment, a first time of PRR of the API may be after 1-2 hours, and a second time of PRR may be from about 2 to 6 hours after the first time of PRR.

In some embodiments, the pulse-release dosage form may comprise a total dose, e.g. a total daily dose, of a cannabinoid API from 1 mg to 100 mg, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg.

In some embodiments, the first pulse-release component ($C_1$) may be an immediate release (IR) formulation of the cannabinoid API. For example, an IR formulation of the API may include, without limitation, the first portion ($P_1$) of the cannabinoid API (API-$P_1$), as well as one or more binders, one or more disintegrants, one or more lubricants, one or more flow aids, or any combinations thereof. In some embodiments, the second pulse-release component ($C_2$) may be a delayed release (DR) formulation of the cannabinoid API. For example, a DR formulation of the API may include, without limitation, the second portion ($P_2$) of the cannabinoid API (API-$P_2$), as well as one or more binders, one or more lubricants, one or more flow aids, or any combinations thereof, and the second pulse-release component may be coated with a layer of one or more pH-dependent or non-pH-dependent polymers, one or more plasticizers, or both.

In some embodiments, the binder may include, but is not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

In some embodiments, the binders may be present in a pulse-release component of the pulse-release dosage form in the range of 1.0 to 60% (W/W).

In addition, other ingredients that may be included in a pulse-release component of the pulse-release dosage form to aid in the dissolution of the API, or the breakdown of the pulse-release component after ingestion or administration may include, without limitation, one or more surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, a non-ionic surfactant such as the Pluronic line of surfactants, or any other material with surface active properties.

In some embodiments, the disintegrant may include, but is not limited to, sodium starch glycolate, corn starch, rice starch, gar gum, polyvinylpolypyrrolidone, croscarmellose, and hydroxypropylmethylcellulose, among others.

In some embodiments, the disintegrants may be present in a pulse-release component of the pulse-release dosage form in the range of 0.05-15% (W/W).

In some embodiments, the lubricant may include, but is not limited to, magnesium stearate, calcium stearate, and stearic acid, among others.

In some embodiments, the lubricants may be present in a pulse-release component of the pulse-release dosage form in the range of 0.05-5% (W/W).

In some embodiments, the flow aid may include, but is not limited to, colloidal silicone dioxide, and magnesium stearate, among others.

In some embodiments, the flow aids may be present in a pulse-release component of the pulse-release dosage form in the range of 0.05-0.5% (W/W).

In some embodiments, the polymer coating may include, but is not limited to, one or more pH-dependent or non-pH-dependent excipients. Examples of non-pH dependent polymers include ethyl cellulose, hydroxypropylmethyl cellulose, hydroxyethyl cellulose, hydroxypropyl cellulose, carboxymethyl cellulose, copolymer of ethyl acrylate, methyl methacrylate (e.g., Eudragit R S), among others. Examples of pH-dependent excipients include methacrylic acid copolymers, hydroxypropylmethyl cellulose acetate succinate, hydroxypropylmethyl cellulose phthalate, and cellulose acetate phthalate, among others. The pH-dependent polymer coating may also include a pore former, such as povidone, polyethylene glycol, hydroxypropyl cellulose, hydroxypropylmethyl cellulose, among others, sugars such as sucrose, mannitol, lactose, and salts, such as sodium chloride, sodium citrate, among others. In some embodiments, the polymer coating may include a plasticizer, such as acetylated citrated esters, acetylated glycerides, castor oil, citrate esters, dibutylsebacate, glyceryl monostearate, diethyl phthalate, glycerol, medium chain triglycerides, propylene glycol, and polyethylene glycol. The coating may also include one or more additional excipients, such as lubricants (e.g., magnesium stearate, talc among others). The coating can be applied using conventional coating techniques such as fluidized bed coating, pan coating, among others.

In certain embodiments, the pH-dependent polymer can be a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers. In certain other embodiments, the acrylic polymer is comprised of one or more ammonia methacrylate copolymers. Ammonio methacrylate copolymers are well known in the art, and are described as fully polymerized copolymers of acrylic and methacrylic acid esters with a low content of quaternary ammonium groups. In still other embodiments, the acrylic polymer may be an acrylic resin lacquer such as a Eudragit®. In further embodiments, the acrylic polymer comprises a mixture of two acrylic resin lacquers commercially available from Evonik/Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. Eudragit® S-100 and Eudragit® L-100 are also suitable for use herein. The code designations RL (high permeability) and RS (low permeability) refer to the permeability properties of these agents. Eudragit® mixtures are insoluble in water and in digestive fluids. However, multi-particulate systems formed to include the same are swellable and permeable in aqueous solutions and digestive fluids. The polymers described above such as Eudragit® RL/RS may be mixed together in any desired ratio in order to ultimately obtain an extended release formulation having a desirable dissolution profile. One skilled in the art will recognize that other acrylic polymers may also be used, such as, for example, Eudragit® L.

In some embodiments, the polymer coatings may be present in a pulse-release component of the pulse-release dosage form in the range of 0.5-35% (W/W).

In some embodiments, the pulse-release dosage form may include API coated cores. In some embodiments, the cores may comprise non-pareils or sugar spheres.

In some embodiments, the pulse-release dosage form may optionally comprise a seal coat. In some embodiments, a DR pulse-release component of the pulse-release dosage form may be coated with a polymer coating by fluidized bed coating.

In some embodiments, a pulse-release component of the present disclosure can be prepared by any suitable method known in the art, such as mixing the ingredients in a suitable pharmaceutical mixer or granulator such as a planetary mixer, high-shear granulator, fluid bed granulator, or extruder, in the presence of water or other solvent, or in a hot melt process. If water or other solvent is used, the blend may be dried in a suitable pharmaceutical drier, such as a vacuum oven or forced-air oven. After allowing the product to cool, the product may be sieved or granulated, and compressed using a suitable tablet press, such as a rotary tablet press.

A pharmaceutical formulation of the present disclosure may be further processed into a solid dosage form suitable for oral administration, such as a pill, tablet or capsule. In some embodiments, the pharmaceutical formulation of the present disclosure may be provided in oral dosage forms such as a syrup, film, orally-disintegrating tablet, a liquid solution or suspension (e.g., drink or syrup), a powder, or liquid or solid crystals, or a paste.

An example method of formulating an example pulse-release oral dosage form of the present disclosure is described in Example 2.

In some embodiments, in the oral pulse-release dosage form of the present disclosure, where the dosage, e.g. the daily dosage, of the API is divided into at least 2 separate releases, the percentage of API released from the first portion ($P_1$) may be from 25% to 75% of the total dose, e.g. the total daily dose, and the percentage of API released from the second portion ($P_2$) may be from 25% to 75% of the total dose, e.g. the total daily dose.

In certain embodiments, the cannabinoid API may be THC. In certain embodiments, the cannabinoid API may be CBN.

In some embodiments, in the oral pulse-release dosage form, the first pulse-release component ($C_1$) may include from at least 2.5 mg to at least 30 mg THC. In some embodiments, in the oral pulse-release dosage form, the first pulse-release component ($C_1$) may include from at least 1.25 mg to at least 75 mg CBN. In some embodiments, in the oral pulse-release dosage form, the second pulse-release component ($C_2$) may include from at least 2.5 mg to at least 30 mg THC. In some embodiments, in the oral pulse-release dosage form, the second pulse-release component ($C_2$) may include from at least 1.25 mg to at least 75 mg CBN.

In some embodiments, the oral pulse-release dosage form of the present disclosure may include a first cannabinoid API and a second cannabinoid API. Accordingly, in some embodiments, the oral pulse-release dosage form may include a total dose, e.g. a total daily dose of a first cannabinoid active pharmaceutical ingredient ($API_1$) and a total dose e.g a total daily dose of a second cannabinoid API ($API_2$), wherein the pulse-release dosage form comprises: a first pulse-release component ($C_1$) comprising a first portion ($P_1$) of the first cannabinoid API ($API_1P_1$) and a first portion ($P_1$) of the second cannabinoid API ($API_2P_1$); and at least a second pulse-release component ($C_2$) comprising a second portion ($P_2$) of the first cannabinoid API ($API_1P_2$) and a second portion ($P_2$) of the second cannabinoid API ($API_2P_2$). In the oral pulse-release dosage form, the total dose e.g the total daily dose of each of the APIs and the $API_2$ is divided between the first portion ($P_1$) in the first pulse-release component ($C_1$) and at least the second portion ($P_2$) in the at least second pulse-release component ($C_2$). When the pulse-release dosage form is placed in a simulated gastrointestinal environment, e.g. an aqueous solution of 0.1N HCl pH 1.1 for 2 hours followed by 8 hours in sodium phosphate buffer at pH 6.8, at 37° C.±0.5° C., the pulse-release dosage form provides release of the $API_1P_2$ and the $API_2P_2$ beginning from 2 to 6 hours after release of the $API_1P_1$ and the $API_2P_1$ begins.

In some embodiments, when the pulse-release dosage form is placed in a simulated gastrointestinal environment, the pulse-release dosage form may provide a second time of peak release rate ($PRR_2$) of each of the $API_1$ ($PRR_2API_1$) and the $API_2$ ($PRR_2API_2$) from about 2 to 6 hours after a first time of peak release rate ($PRR_1$). In some embodiments, the $PRR_1$ may be after 1-2 hours.

In some embodiments, the first cannabinoid $API_1$ may be THC and the second cannabinoid $API_2$ may be cannabinol (CBN), and the total dose, e.g. the total daily dose, of the THC is from 1 mg to 40 mg and the total dose, e.g. the total daily dose of the CBN is from 2.5 mg to 100 mg.

In some embodiments, the first cannabinoid $API_1$ may be THC and the second cannabinoid $API_2$ may be CBN, and the total dose, e.g. the total daily dose, of the THC is selected from: at least 1 mg, at least 2 mg, at least 3 mg, at least 4 mg, at least 5 mg, at least 6 mg, at least 8 mg, at least 10 mg, at least 15 mg, at least 20 mg, at least 25 mg, at least 30 mg, and at least 35 mg, and the total dose e.g. the total daily dose, of the CBN is selected from: at least 2.5 mg, at least 3 mg, at least 4 mg, at least 5 mg, at least 10 mg, at least 15 mg, at least 20 mg, at least 25 mg, at least 30 mg, at least 35 mg, and at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

In some embodiments, the first pulse-release component ($C_1$) may be an immediate release (IR) formulation of the first cannabinoid $API_1$ and the second cannabinoid $API_2$, comprising the first portion ($P_1$) of the first cannabinoid API ($API_1P_1$) and the first portion ($P_1$) of the second cannabinoid API ($API_2P_1$). In some embodiments, the second pulse-release component ($C_2$) may be a delayed release (DR) formulation of the first cannabinoid $API_1$ and the second cannabinoid $API_2$, comprising the second portion ($P_2$) of the first cannabinoid API ($API_1P_2$) and a second portion ($P_2$) of the second cannabinoid API ($API_2P_2$).

In some embodiments, for each API, the first portion ($P_1$) may be independently selected from 25% to 75% of the total dose, e.g. the total daily dose, and for each API the second portion ($P_2$) may be independently selected from 25% to 75% of the total dose, e.g. the total daily dose.

In some embodiments, the first pulse-release component ($C_1$) may comprise from 0.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The second pulse-release component ($C_2$) may comprise from 0.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN.

In some embodiments, the daily dosage is at least 1 mg THC and at least 10 mg CBN. In some embodiments, the daily dosage is at least 2 mg THC and at least 20 mg CBN. In some embodiments, the daily dosage is at least 4 mg THC and at least 40 mg CBN. In some embodiments, the daily dosage is at least 5 mg THC and at least 2.5 mg CBN. In some embodiments, the daily dosage is at least 6 mg THC and at least 3 mg CBN. In some embodiments, the daily dosage is at least 8 mg THC and at least 4 mg CBN. In some embodiments, the daily dosage is at least 5 mg THC and at least 10 mg CBN. In some embodiments, the daily dosage is at least 10 mg THC and at least 10 mg CBN. In some embodiments, the daily dosage is at least 20 mg THC and at least 10 mg CBN. In some embodiments, the daily dosage is at least 20 mg THC and at least 20 mg CBN. In some embodiments, the daily dosage is at least 10 mg THC and at least 20 mg CBN. In some embodiments, the daily dosage is at least 10 mg THC and at least 25 mg CBN. In some embodiments, the daily dosage is at least 10 mg THC and at least 30 mg CBN. In some embodiments, the daily dosage is at least 10 mg THC and at least 40 mg CBN.

Example formulations of the pulse-release oral dosage forms of the present disclosure are provided in Example 1.

In some embodiments, the oral pulse-release dosage form comprises a total dose e.g. a total daily dose of a first cannabinoid active pharmaceutical ingredient ($API_1$) and a total dose e.g. a total daily dose of a second cannabinoid API ($API_2$), wherein the pulse-release dosage form comprises a first pulse-release component ($C_1$) comprising a first portion ($P_1$) of the first cannabinoid API ($API_1P_1$) and a first portion ($P_1$) of the second cannabinoid API ($API_2P_1$), a second pulse-release component ($C_2$) comprising a second portion ($P_2$) of the first cannabinoid API ($API_1P_2$) and a second portion ($P_2$) of the second cannabinoid API ($API_2P_2$), and at least a third pulse-release component ($C_3$) comprising a third portion ($P_3$) of the first cannabinoid API ($API_1P_3$) and a third portion ($P_3$) of the second cannabinoid API ($API_2P_2$). In the oral pulse-release dosage form, the total dose e.g. the total daily dose of each of the $API_1$ and the $API_2$ is divided between the first portion ($P_1$) in the first pulse-release component ($C_1$), the second portion ($P_2$) in the second pulse-release component ($C_2$), and at least the third portion ($P_3$) in the at least third pulse-release component ($C_3$). When the pulse-release dosage form is placed in an aqueous solution of 0.1N HCl pH 1.1 for 2 hours followed by 8 hours in sodium phosphate buffer at pH 6.8, at 37° C.±0.5° C., the pulse-release dosage form provides release of the $API_1P_2$ and the $API_2P_2$ beginning from 1 to 4 hours after release of the $API_1P_1$ and the $API_2P_1$ begins, and release of the $API_1P_3$ and the $API_2P_3$ beginning from 1 to 4 hours after release of the $API_1P_2$ and the $API_2P_2$ begins.

In some embodiments, the oral pulse-release dosage form provides a second time of peak release rate ($PRR_2$) of each of the $API_1$ ($PRR_2API_1$) and the $API_2$ ($PRR_2API_2$) from about 1 to 4 hours after a first time of peak release rate ($PRR_1$) and a third time of peak release rate ($PRR_3$) of each of the $API_1$ ($PRR_3API_1$) and the $API_2$ ($PRR_3API_2$) from about 1 to 4 hours after the second time of peak release rate ($PRR_2$). In some embodiments, the $PRR_1$ is after 1-2 hours.

In some embodiments, when the oral pulse-release dosage form provides release of a dosage, e.g. a daily dosage, of the $API_1$ and the $API_2$ into the gastrointestinal tract of the subject, divided into at least 3 separate releases, the first cannabinoid $API_1$ may be THC and the second cannabinoid $API_2$ may be CBN. The total dose, e.g. the total daily dose, of the THC may be from 10 mg to 40 mg and the total dose e.g. the total daily dose of the CBN may be from 5 mg to 100 mg. In some embodiments, the first cannabinoid $API_1$ is THC and the second cannabinoid $API_2$ is CBN, and the total dose e.g. the total daily dose of the THC is selected from: at least 10 mg, at least 15 mg, at least 20 mg, at least 25 mg, at least 30 mg, and at least 35 mg, and the total dose e.g. the total daily dose of the CBN is selected from: at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

In some embodiments, the first pulse-release component ($C_1$) may be an immediate release (IR) formulation of the first cannabinoid $API_1$ and the second cannabinoid $API_2$, comprising the first portion ($P_1$) of the first cannabinoid API ($API_1P_1$) and a first portion ($P_1$) of the second cannabinoid API ($API_2P_1$). The second pulse-release component ($C_2$) may be a delayed release (DR) formulation of the first cannabinoid $API_1$ and the second cannabinoid $API_2$, comprising the second portion ($P_2$) of the first cannabinoid API ($API_1P_2$) and a second portion ($P_2$) of the second cannabinoid API ($API_2P_2$). The third pulse-release component ($C_3$) may be a delayed release (DR) formulation of the first cannabinoid $API_1$ and the second cannabinoid $API_2$, comprising the third portion ($P_3$) of the first cannabinoid API ($API_1P_3$) and a third portion ($P_3$) of the second cannabinoid API ($API_2P_3$). The second pulse-release component may be coated with a first delayed-release layer comprising one or more pH-dependent and/or non-pH-dependent polymers, and optionally one or more plasticizers, one or more pore formers, and/or one or lubricants. The third pulse-release component may be coated with a second delayed-release layer comprising one or more pH-dependent and/or non-pH-dependent polymers, and optionally one or more plasticizers, one or more pore formers, and/or one or lubricants. The second delayed-release layer may provide a delayed release of 1-4 hours longer than the first delayed-release layer.

In some embodiments, for each API, the first portion ($P_1$) may be independently selected from 25% to 75% of the total dose e.g. the total daily dose, for each API, the second portion ($P_2$) may be independently selected from 25% to 75% of the total dose e.g. the total daily dose, and, for each API, the third portion ($P_3$) may be independently selected from 25% to 75% of the total dose e.g. the total daily dose.

In some embodiments, the first pulse-release component ($C_1$) may include from 2.5 mg to 30 mg of the first cannabinoid active pharmaceutical ingredient ($API_1$), wherein the $API_1$ is THC, and from at least 1.25 mg to 75 mg of the second cannabinoid active pharmaceutical ingredient ($API_1$), wherein the $API_1$ is CBN. The second pulse-release component ($C_2$) may include from 2.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN. The third pulse-release component ($C_3$) may include from 2.5 mg to 30 mg of the first cannabinoid active pharmaceutical ingredient ($API_1$), wherein the $API_1$ is THC, and from 1.25 mg to 75 mg of the second cannabinoid active pharmaceutical ingredient ($API_1$), wherein the $API_1$ is CBN.

C. Method of Treating a Sleep Disorder

In some embodiments, the present disclosure provides a method of treating a sleep disorder in a subject in need thereof, the method comprising administering to the subject an oral pulse-release dosage form of the present disclosure. In some embodiments, the administering may be up to 30 minutes, up to 1 hour, or up to 2 hours before the subject intends to begin sleeping at night.

The description herein is primarily directed to treatment of sleep disorders in subjects with a typical schedule, wherein the subject intends to go to sleep starting from around 9 P.M. to about midnight, for example. Accordingly, terms used herein such as "at night", "during the night" and so on are intended to refer to the usual period of time when the subject intends to be asleep, and, similarly, terms such as "in the morning" are intended to refer to a period after the subject's usual sleeping time. It is understood, however, that the use and efficacy of the compositions and methods described herein, is not limited to such a schedule, but can be adopted for use with different daily schedules, such as night workers, or people with more variable sleep patterns.

In some embodiments, the term sleep disorder as used herein more particularly refers to insomnia. Insomnia may include a difficulty falling asleep or staying asleep, or both. In some embodiments, the sleep disorder may be characterized primarily or predominantly by various symptoms, such as difficulty falling asleep or may be characterized primarily or predominantly by difficulty staying asleep, either in an individual subject, or in a group of subjects, such as a population of subjects. In some embodiments, the sleep disorder may include, without limitation, one or more of insufficient total sleeping time during the night, increased frequency of awakenings during the night, increased number of times out of bed at night, increased time awake at night, increased latency to sleep onset, deviations from proportions of time or duration of time in light sleep, deep sleep and/or REM sleep compared to those typically seen in individuals that do not experience insomnia, and the insomnia may produce a number of effects, such as not feeling well rested in the morning and/or during the day, decreased sleep satisfaction, increase in number of naps during the day, decreased wakefulness during daytime activities such as during work or school, or any combinations thereof.

In some embodiments, administering a subject in need of treatment for a sleep disorder with an oral pulse-release dosage form of the present disclosure may provide effective treatment of one or more aspects of the subject's sleep disorder.

For example, as described in Example 4, an example pulse-release dosage form comprising two example cannabinoid API's, THC and CBN provided effective treatment of insomnia in a group of subjects. In particular, the subjects in the study described in Example 4 experienced insomnia, primarily or predominantly characterized by difficulty staying asleep at night. Traditional sleep aids were marginally effective, and had a profound impact on quality of sleep, and in particular REM and deep sleep components of their sleep experience. The example formulation provided the subjects with longer sleep duration, and no deleterious effects on REM and deep sleep components of the sleep experience. In addition, surprisingly, the subjects experienced few residual effects (or "hangover") of the treatment. This is in stark contrast to other drugs commonly used for sleep disorders Surprisingly, the treatment did not affect all aspects of the subjects' sleep experience equally. For example, there was no effect on objective measures of latency to sleep onset, number of awakenings during the night, and no increase in time in REM sleep or deep sleep.

Recent studies indicate that individuals using *Cannabis* expect it to decrease their sleep-related problems (Altman et al., 2019) and are likely to reduce their use of sleep medications (Piper et al., 2017). Participants in the study by Altman and colleagues (2019) reported that using *Cannabis* helped them fall asleep about 15 minutes faster and sleep for about 2 hours longer. Nonetheless, previous studies have shown that the optimal concentration, dosage, timing, and route of administration for treating sleep disorders remain unknown (Babson et al., 2017).

Unexpectedly, as described in Example 5, and in contrast to the findings described in Example 4, administering subjects reporting difficulty in falling asleep with the same dosage of 10 mg THC and 5 mg CBN, but delivered in an immediate release dosage form via the sublingual route, did not result in any objectively measured improvements in any aspect of sleep. To the contrary, surprisingly, 10 mg THC and 5 mg CBN delivered in an immediate release dosage form via the sublingual route significantly increased the time to fall asleep in these subjects.

Therefore, not all administration routes or dosage forms of cannabinoids, or dosage timing, may be expected to be useful for treating subjects experiencing insomnia. In addition, not all symptoms of insomnia may be effectively or equally treated by administering a subject with various formulations of cannabinoids.

Accordingly, the oral pulse-release compositions and dosage forms described herein may provide particular advantages as compared to other medications for treating sleep disorders.

In some embodiments, administering a subject in need of treatment for a sleep disorder with an oral pulse-release dosage form of the present disclosure may result in an increase in the subject's total sleeping time during the night.

In some embodiments, the administering may result in an increase in the subject's total light sleeping time during the night.

In some embodiments, the administering may result in an increase in the subject's light sleeping time as a proportion of total sleeping time during the night.

In some embodiments, the administering may result in an increase in the subject's total time in bed during the night.

In some embodiments, the effects of the administering on the subject may be measured using a SleepScore Max® system (e.g., see Example 4).

In some embodiments, the administering may result in an increase in SleepScore number as determined using a SleepScore Max® system.

In some embodiments, the administering may result in the subject experiencing an increase in feeling well rested in the morning and/or during the day, perceived sleep quality, perceived total sleep time during the night, sleep satisfaction, or any combinations thereof. The administering may result in the subject experiencing a decrease in perceived frequency of awakenings during the night, number of times out of bed at night, number of naps during the day, or perceived time awake at night, or any combinations thereof.

In some embodiments, the subject in need of treatment may be experiencing insomnia that is primarily characterized by an inability to stay asleep during the night. In some embodiments, the insomnia may be characterized using objective measurements, e.g. using a SleepScore Max® system. In some embodiments, characterization of the sleep disorder is reported by the subject, e.g. identified subjectively, or without using objective analysis e.g. using a SleepScore Max® system.

In some embodiments, the administering may not result in a decrease in latency to sleep onset, an alteration of time in deep sleep and/or REM sleep, a hangover effect during the day after the administering, or any combinations thereof.

In some embodiments, the administering may result in a decrease in latency to sleep onset.

In some embodiments, the subject may have been previously been administered with one or more cannabinoids for treating a medical condition. For example, the subject may have previously used medical marijuana for one or more medical conditions.

The term "subject" as used herein refers to a warm blooded animal such as a mammal which is treated for a condition that causes at least one symptom. It is understood that at least humans, dogs, cats, and horses are within the scope of the meaning of the term. In some embodiments, the subject is a human. In particular, the subject may be in need of treatment for a sleep disorder, e.g. insomnia.

As used herein, the term "treat" or "treatment", or a derivative thereof, contemplates partial or complete amelioration of at least one symptom associated with the condition of the subject.

EXAMPLES

The present examples are provided for illustrative purposes only. They are not intended to and should not be interpreted to encompass the full breadth of the disclosure.

Example 1. Formulations of Example THC and CBN Oral Pulse-Release Dosage Forms This Example provides example formulations of a pulse-release THC and CBN oral dosage forms of the present disclosure.

Example 1(a)

| First pulse-release component | | |
|---|---|---|
| THC | 5 mg | 5.7% |
| CBN | 2.5 mg | 2.8% |
| Microcrystalline Cellulose | 65 mg | 73.9% |
| Hydroxypropylmethylcellulose | 15 mg | 17.0% |
| Magnesium stearate | 0.5 mg | 0.6% |
| Total | 88.0 mg | 100.0% |
| Second pulse-release component | | |
| THC | 5 mg | 3.8% |
| CBN | 2.5 mg | 1.9% |
| Microcrystalline Cellulose | 95 mg | 71.4% |
| Methacrylic acid copolymer | 30 mg | 22.6% |
| Magnesium stearate | 0.25 mg | 0.2% |
| Colloidal silicone dioxide | 0.25 mg | 0.2% |
| Total | 133.0 mg | 100.0% |

Example 1(b)

| First pulse-release component | | |
|---|---|---|
| THC | 5 mg | 5.4% |
| CBN | 2.5 mg | 2.7% |
| Microcrystalline Cellulose | 65 mg | 70.7% |
| Hydroxypropylmethylcellulose | 10 mg | 10.8% |
| Lactose | 5 mg | 5.4% |
| Sodium starch glycolate | 4 mg | 4.3% |
| Magnesium stearate | 0.5 mg | 0.5% |
| Total | 92.0 mg | 100.0% |
| Second pulse-release component | | |
| THC | 5 mg | 3.0% |
| CBN | 2.5 mg | 1.5% |
| Microcrystalline Cellulose | 120 mg | 71.1% |
| Methacrylic acid copolymer | 40 mg | 23.7% |
| Magnesium stearate | 0.7 mg | 0.4% |
| Colloidal silicone dioxide | 0.5 mg | 0.3% |
| Total | 168.7 mg | 100.0% |

Example 1(c)

This is an example of a first pulse-release component that may be combined with any second pulse-release component described herein, e.g. may be combined with the second pulse-release component of Example 1(b) in some embodiments.

| | | |
|---|---|---|
| THC | 3.27% | 10 mg |
| CBN | 1.63% | 5 mg |
| Sugar Spheres | 20.60% | 63 mg |
| Microcrystalline cellulose 200 | 16.50% | 50.5 mg |
| Microcrystalline cellulose 302 | 24.10% | 73.7 mg |
| Croscarmellose sodium | 5.80% | 17.7 mg |
| Isomalt | 24.20% | 74 mg |
| FD&C Blue #2 | 0.30% | 0.9 mg |
| Silicone dioxide | 0.50% | 1.5 mg |
| Magnesium stearate | 1.00% | 3.1 mg |
| Non-functional coating | 2.10% | 6.4 mg |
| | 100.00% | 305.8 mg |

Example 1(d)

This is an example of a first pulse-release component that may be combined with any second pulse-release component described herein, e.g. may be combined with the second pulse-release component of Example 1(b) in some embodiments.

| | | |
|---|---|---|
| THC | 3.27% | 10 mg |
| CBN | 1.63% | 5 mg |
| Sugar Spheres | 20.60% | 63 mg |
| Microcrystalline cellulose 200 | 16.50% | 50.5 mg |
| Microcrystalline cellulose 302 | 24.10% | 73.7 mg |
| Croscarmellose sodium | 5.80% | 17.7 mg |
| Isomalt | 24.20% | 74 mg |
| FD&C Blue #2 | 0.30% | 0.9 mg |
| Silicone dioxide | 0.50% | 1.5 mg |
| Magnesium stearate | 1.00% | 3.1 mg |
| Non-functional coating | 2.10% | 6.4 mg |
| | 100.00% | 305.8 mg |

Example 1(e)

| First pulse-release component | | |
|---|---|---|
| THC | 5 mg | 4.6% |
| CBN | 2.5 mg | 2.3% |
| Lactose | 85 mg | 78.7% |
| Polyvinylpyrrolidone | 10 mg | 9.2% |
| Polyvinylpolypyrrolidone | 5 mg | 4.6% |
| Magnesium stearate | 0.5 mg | 0.5% |
| Total | 108.0 mg | 100.0% |

| Second pulse-release component | | |
|---|---|---|
| THC | 5 mg | 3.8% |
| CBN | 2.5 mg | 1.9% |
| Microcrystalline Cellulose | 95 mg | 71.4% |
| Methacrylic acid copolymer | 30 mg | 22.6% |
| Magnesium stearate | 0.25 mg | 0.2% |
| Colloidal silicone dioxide | 0.25 mg | 0.2% |
| Total | 133.0 mg | 100.0% |

Example 1(f)

| First pulse-release component | | |
|---|---|---|
| THC | 10.0 mg | 5.3% |
| CBN | 5.0 mg | 2.7% |
| Microcrystalline Cellulose | 125.0 mg | 66.8% |
| Hydroxypropylmethylcellulose | 35.0 mg | 18.7% |
| Croscarmellose Sodium | 11 mg | 5.9% |
| Magnesium stearate | 1.2 mg | 0.6% |
| Total | 187.2 mg | 100.0% |

| Second pulse-release component | | |
|---|---|---|
| THC | 5 mg | 3.8% |
| CBN | 2.5 mg | 1.9% |
| Microcrystalline Cellulose | 95 mg | 71.4% |
| Methacrylic acid copolymer | 30 mg | 22.6% |
| Magnesium stearate | 0.25 mg | 0.2% |
| Colloidal silicone dioxide | 0.25 mg | 0.2% |
| Total | 133.0 mg | 100.0% |

Example 1(g)

| First pulse-release component | | |
|---|---|---|
| THC | 10.0 mg | 5.3% |
| CBN | 5.0 mg | 2.7% |
| Microcrystalline Cellulose | 125.0 mg | 66.8% |
| Hydroxypropylmethylcellulose | 35.0 mg | 18.7% |
| Croscarmellose Sodium | 11 mg | 5.9% |
| Magnesium stearate | 1.2 mg | 0.6% |
| Total | 187.2 | 100.0% |

| Second pulse-release component | | |
|---|---|---|
| THC | 10 mg | 3.6% |
| CBN | 5 mg | 1.8% |
| Microcrystalline Cellulose | 200 mg | 71.2% |
| Methacrylic acid copolymer | 65 mg | 23.1% |
| Magnesium stearate | 0.5 mg | 0.2% |
| Colloidal silicone dioxide | 0.5 mg | 0.2% |
| Total | 281.0 mg | 100.0% |

Example 1(h)

| First pulse-release component | | |
|---|---|---|
| THC | 10.0 mg | 5.3% |
| CBN | 5.0 mg | 2.7% |
| Microcrystalline Cellulose | 125.0 mg | 66.8% |
| Hydroxypropylmethylcellulose | 35.0 mg | 18.7% |
| Croscarmellose Sodium | 11 mg | 5.9% |
| Magnesium stearate | 1.2 mg | 0.6% |
| Total | 187.2 mg | 100.0% |

| Second pulse-release component | | |
|---|---|---|
| THC | 20.0 mg | 6.1% |
| CBN | 10.0 mg | 3.0% |
| Microcrystalline Cellulose | 225.0 mg | 68.3% |
| Methacrylic acid copolymer | 72.5 mg | 21.9% |
| Magnesium stearate | 1.5 mg | 0.5% |
| Colloidal silicone dioxide | 0.75 mg | 0.2% |
| Total | 329.3 mg | 100.0% |

Example 1(i)

| First pulse-release component | | |
|---|---|---|
| THC | 5.0 mg | 5.3% |
| CBN | 10. 0 mg | 2.7% |
| Microcrystalline Cellulose | 125.0 mg | 66.8% |
| Croscarmellose Sodium | 11 mg | 5.9% |
| Magnesium stearate | 1.2 mg | 0.6% |
| Total | 187.2 mg | 100.0% |

| Second pulse-release component | | |
|---|---|---|
| THC | 5.0 mg | 3.8% |
| CBN | 10. 0 mg | 1.9% |
| Microcrystalline Cellulose | 215.0 mg | 71.4% |
| Hydroxypropylmethylcellulose acetate | 57.0 mg | 22.6% |
| Magnesium stearate | 1.5 mg | 0.2% |
| Colloidal silicone dioxide | 0.75 mg | 0.2% |
| Total | 289.25 mg | 100.0% |

Example 1(j)

| First pulse-release component | | |
|---|---|---|
| THC | 10.0 mg | 4.7% |
| CBN | 10.0 mg | 4.7% |
| Microcrystalline Cellulose | 135.0 mg | 63.2% |
| Hydroxypropylmethylcellulose | 41.3 mg | 19.3% |
| Croscarmellose Sodium | 16 mg | 7.5% |
| Magnesium stearate | 1.2 mg | 0.6% |
| Total | 213.5 mg | 100.0% |
| Second pulse-release component | | |
| THC | 5.0 mg | 2.7% |
| CBN | 10.0 mg | 5.4% |
| Microcrystalline Cellulose | 125.0 mg | 70.0% |
| Methacrylic acid copolymer | 43.0 mg | 23.4% |
| Magnesium stearate | 0.6 mg | 0.3% |
| Colloidal silicone dioxide | 0.3 mg | 0.2% |
| Total | 183.9 mg | 100.0 |

Example 1(k)

| First pulse-release component | | |
|---|---|---|
| THC | 10.0 mg | 4.7% |
| CBN | 10.0 mg | 4.7% |
| Microcrystalline Cellulose | 135.0 mg | 63.2% |
| Hydroxypropylmethylcellulose | 41.3 mg | 19.3% |
| Croscarmellose Sodium | 16 mg | 7.5% |
| Magnesium stearate | 1.2 mg | 0.6% |
| Total | 213.5 mg | 100.0% |
| Second pulse-release component | | |
| THC | 5.0 mg | 2.7% |
| CBN | 10.0 mg | 5.4% |
| Microcrystalline Cellulose | 125.0 mg | 70.0% |
| Cellulose Acteate Pthalate | 43.0 mg | 23.4% |
| Magnesium stearate | 0.6 mg | 0.3% |
| Third pulse-release component | | |
| THC | 5.0 mg | 2.7% |
| CBN | 10.0 mg | 5.4% |
| Microcrystalline Cellulose | 125.0 mg | 70.0% |
| Methacrylic acid copolymer | 43.0 mg | 23.4% |
| Magnesium stearate | 0.6 mg | 0.3% |

Example 1(l)

| First pulse-release component | | |
|---|---|---|
| THC | 2.5 mg | 1.3% |
| CBN | 1.25 mg | 0.6% |
| Microcrystalline Cellulose | 135.0 mg | 68.4% |
| Hydroxypropylmethylcellulose | 41.3 mg | 20.9% |
| Croscarmellose Sodium | 16 mg | 8.1% |
| Magnesium stearate | 1.2 mg | 0.6% |
| Total | 197.25 mg | 100.0% |
| Second pulse-release component | | |
| THC | 2.5 mg | 1.4% |
| CBN | 1.25 mg | 0.7% |
| Microcrystalline Cellulose | 125.0 mg | 72.4% |
| Methacrylic acid copolymer | 43.0 mg | 24.9% |
| Magnesium stearate | 0.6 mg | 0.3% |
| Colloidal silicone dioxide | 0.3 mg | 0.2% |
| Total | 172.65 mg | 100.0% |

Example 1(m)

| First pulse-release component | | |
|---|---|---|
| THC | 3.0 mg | 1.5% |
| CBN | 1.5 mg | 0.8% |
| Microcrystalline Cellulose | 135.0 mg | 68.2% |
| Hydroxypropylmethylcellulose | 41.3 mg | 20.9% |
| Croscarmellose Sodium | 16.0 mg | 8.1% |
| Magnesium stearate | 1.2 mg | 0.6% |
| Total | 198.0 mg | 100.0 |
| Second pulse-release component | | |
| THC | 3.0 mg | 1.7% |
| CBN | 1.5 mg | 0.9% |
| Microcrystalline Cellulose | 125.0 mg | 72.1% |
| Methacrylic acid copolymer | 43.0 mg | 24.8% |
| Magnesium stearate | 0.6 mg | 0.3% |
| Colloidal silicone dioxide | 0.3 mg | 0.2% |
| Total | 173.4 mg | 100.0% |

Example 1(n)

| First pulse-release component | | |
|---|---|---|
| THC | 4.0 mg | 2.0% |
| CBN | 2.0 mg | 1.0% |
| Microcrystalline Cellulose | 135.0 mg | 67.7% |
| Hydroxypropylmethylcellulose | 41.3 mg | 20.7% |
| Croscarmellose Sodium | 16 mg | 8.0% |
| Magnesium stearate | 1.2 mg | 0.6% |
| Total | 199.5 mg | 100.0% |
| Second pulse-release component | | |
| THC | 4.0 mg | 2.3% |
| CBN | 2.0 mg | 1.1% |
| Microcrystalline Cellulose | 125.0 mg | 71.5% |
| Methacrylic acid copolymer | 43.0 mg | 24.6% |
| Magnesium stearate | 0.6 mg | 0.3% |
| Colloidal silicone dioxide | 0.3 mg | 0.2% |
| Total | 174.9 mg | 100.0% |

Example 1(o)

| First pulse-release component | | |
|---|---|---|
| THC | 0.5 mg | 0.3% |
| CBN | 5.0 mg | 2.5% |
| Microcrystalline Cellulose | 135.0 mg | 67.8% |
| Hydroxypropylmethylcellulose | 41.3 mg | 20.8% |
| Croscarmellose Sodium | 16 mg | 8.0% |
| Magnesium stearate | 1.2 mg | 0.6% |
| Total | 199.0 mg | 100.0% |

-continued

| Second pulse-release component | | |
|---|---|---|
| THC | 0.5 mg | 0.3% |
| CBN | 5.0 mg | 2.9% |
| Microcrystalline Cellulose | 125.0 mg | 71.7% |
| Methacrylic acid copolymer | 43.0 mg | 24.7% |
| Magnesium stearate | 0.6 mg | 0.3% |
| Colloidal silicone dioxide | 0.3 mg | 0.2% |
| Total | 174.4 mg | 100.0% |

Example 1(p)

| First pulse-release component | | |
|---|---|---|
| THC | 1.0 mg | 0.5% |
| CBN | 10.0 mg | 4.9% |
| Microcrystalline Cellulose | 135.0 mg | 66.0% |
| Hydroxypropylmethylcellulose | 41.3 mg | 20.2% |
| Croscarmellose Sodium | 16 mg | 7.8% |
| Magnesium stearate | 1.2 mg | 0.6% |
| Total | 204.5 mg | 100.0% |
| Second pulse-release component | | |
| THC | 1.0 mg | 0.6% |
| CBN | 10.0 mg | 5.6% |
| Microcrystalline Cellulose | 125.0 mg | 69.5% |
| Methacrylic acid copolymer | 43.0 mg | 23.9% |
| Magnesium stearate | 0.6 mg | 0.3% |
| Colloidal silicone dioxide | 0.3 mg | 0.2% |
| Total | 179.9 mg | 100.0% |

Example 1(q)

| First pulse-release component | | |
|---|---|---|
| THC | 2.0 mg | 0.9% |
| CBN | 20.0 mg | 9.3% |
| Microcrystalline Cellulose | 135.0 mg | 62.6% |
| Hydroxypropylmethylcellulose | 41.3 mg | 19.2% |
| Croscarmellose Sodium | 16 mg | 7.4% |
| Magnesium stearate | 1.2 mg | 0.6% |
| Total | 215.5 mg | 100.0% |
| Second pulse-release component | | |
| THC | 2.0 mg | 1.0% |
| CBN | 20.0 mg | 10.5% |
| Microcrystalline Cellulose | 125.0 mg | 65.5% |
| Methacrylic acid copolymer | 43.0 mg | 22.5% |
| Magnesium stearate | 0.6 mg | 0.3% |
| Colloidal silicone dioxide | 0.3 mg | 0.2% |
| Total | 190.9 mg | 100.0% |

Example 2. Formulation of an Example Oral Pulsatile Dosage Form of THC and CBN

This Example describes a method of formulating an example 2-pulse oral dosage form of THC and CBN. For example, example THC and CBN oral dosage forms of Example 1 (e.g., Examples 1a, 1b, 1c, 1d, 1e and 1f, among others described herein) may in some embodiments be formulated according to the methods described in Example 2. In this example, the THC and CBN is formulated in a 50:50 ratio of immediate release ("IR THC+CBN", for release in pulse 1): extended release ("ER THC+CBN", for release in pulse 2).

Dispensing and Raw Material Preparation (a) Preparation of Coating Suspension:

Weigh VIVACOAT Protect E into an appropriately sized container. Weigh 60 mL Ethanol into a suitably sized beaker equipped with a magnetic stir bar. Place beaker with Ethanol onto the magnetic stir plate and begin mixing vigorously without splashing. Slowly add the VIVACOAT Protect E to the Ethanol while stirring. Stir speed may be adjusted as needed.

(b) Preparation of the Oil Containing the THC and CBN:

Heat an amount of oil sufficient to contain the desired amount of THC and CBN (e.g., about 30 mL to 120 mL) in an oven at 90° C. to lower the viscosity.

(i) Preparation of ER THC+CBN Oil:

Weigh half of the oil containing THC and CBN into a beaker with a magnetic stir bar—this half of the oil will be the ER THC+CBN oil. Place beaker on magnetic stir plate and begin spinning. Weigh out the Ethanol (approximately 60 mL) and add it to the ER THC+CBN oil. Some stirring with a spatula may be required for the stir bar to spin freely. Adjust speed of the magnetic stirrer to maintain good mixing.

(ii) Preparation of IR THC+CBN Oil:

Move the remaining half of the oil containing THC and CBN to a magnetic stir plate with a stir bar and begin stirring—this half of the oil will be the IR THC+CBN oil. Weigh out the Ethanol (approximately 60 mL) and add it to the IR THC+CBN oil. Some stirring with a spatula may be required for the stir bar to spin freely. Adjust speed of the magnetic stirrer to maintain good mixing.

(c) Preparation of the Substrate and Microcrystalline Cellulose LP200:

Weigh out a first aliquot of 1,000 g of substrate (e.g., sugar spheres) and load into the bowl of a planetary mixer. Weigh out a second aliquot of 1,000 g of substrate into a separate container and set aside. Weigh a first portion of 600 g of microcrystalline cellulose LP200 into a container. Weigh a second portion of 600 g of microcrystalline cellulose LP200 in a separate container. Weigh a third portion of 400 g of microcrystalline cellulose LP200 in a separate container.

Plating and Coating (a) Preparation of ER THC+CBN Powder:

Begin mixing the first aliquot of the substrate in the mixer at low speed. Slowly add the ER THC+CBN oil into the substrate while mixing. Maintain a slow consistent pour until all ER THC+CBN oil has been added. Use some extra Ethanol to rinse any residual oil from the beaker and add to the substrate. Slowly add the first portion of microcrystalline cellulose LP200 to the mixer. Stir well until combined, stopping when needed to break up clumps. Ensure all the ER THC+CBN oil is incorporated into substrate and microcrystalline cellulose LP200. Continue slowly mixing and slowly add the VIVACOAT Protect E/Ethanol coating suspension. Maintain a slow consistent pour until all coating suspension has been added. Slowly add the 400 g portion of microcrystalline cellulose LP200 to the mixing bowl while mixing at slow speed. Stir well until combined, stopping when needed to break up clumps. Empty mixer contents onto a baking sheet and spread out for drying.

(b) Preparation of IR THC+CBN Powder:

Begin mixing second aliquot of substrate in the mixer at low speed. Slowly add the IR THC+CBN oil into the substrate while mixing. Maintain a slow consistent pour until all the IR THC+CBN oil has been added. Use some extra Ethanol to rinse any residual oil from the beaker and add to the substrate. Slowly add the remaining microcrystalline cellulose LP200 to the mixer. Stir well until combined, stopping when needed to break up clumps. Ensure all the IR THC+CBN oil is incorporated into substrate and microcrystalline cellulose LP200. Empty mixer contents onto a baking sheet and spread out for drying.

Powder Drying

Dry the ER and IR powders under high vacuum with no heat for ~3 hours or until dry. If a vacuum environment is not available, place trays on a baker's rack and set in a low humidity (RH 45%) room overnight. Retrieve trays with dried powder. Keep ER and IR powders separate until the blending step (below). Break up clumps by hand or with a mortar and pestle. Sieve the powders separately through a #20 mesh screen. If not blending right away, double bag the powders separately and seal with a desiccant pack in the outer bag.

Blending

Load the ER and IR powder into a V-Blender. Weigh microcrystalline cellulose M302 and add it to the V-Blender. Weigh Isomalt and add it to the V-Blender. Weigh croscarmellose sodium and add it to the V-Blender. Blend the mixture at top speed for 2 minutes. Weigh and sieve blue dye through a #20 mesh screen. Add the blue dye by making a shallow pocket in the center of the powder, adding the blue dye, and filling the pocket with the powder blend. Blend mixture for 12 minutes. Weigh and sieve magnesium stearate through a #20 mesh screen. Add the magnesium stearate to the blend in the same manner as the blue dye. Blend mixture for 2 minutes. Discharge blend slowly into a poly bag. Double bag with desiccant pack in the outer bag.

Tableting

Load the powdered blend into the hopper of an Elizabeth EP 200 tablet press. Begin batch compression utilizing the following parameters: tablet tooling 9 mm round concave; tablet hardness 6-20 kp. Compress at the target weight and collect tablets in an appropriately sized container.

Example 3—In Vitro Dissolution Testing

In vitro dissolution testing was performed on a 2-pulse oral dosage form of THC and CBN.

The in vitro dissolution testing was performed as follows:

The example pulse-release oral dosage form was placed in 0.1N HCl for two hours, with sampling time points at 1, 1.5 and 2 hours, followed by 8 hours in sodium phosphate buffer pH 6.8, at 37° C.±0.5° C., with sampling at 3, 3.5, 4, 5, 6, 7, 8, 9 and 10 hours.

THC concentration was measured using HPLC.

FIG. 1 is a graph reporting the in vitro dissolution release rate (μg/mL per timepoint) of THC versus time in hours of an example 2-pulse oral pharmaceutical composition tablet. The immediate release component (providing pulse 1) began to be dissolved immediately, resulting in a first time of peak release rate ($PRR_1$) after 1-2 hours. Dissolution of the delayed release component (pulse 2) provided a second time of peak release rate ($PRR_2$) after 3-4 hours.

Figure 2:
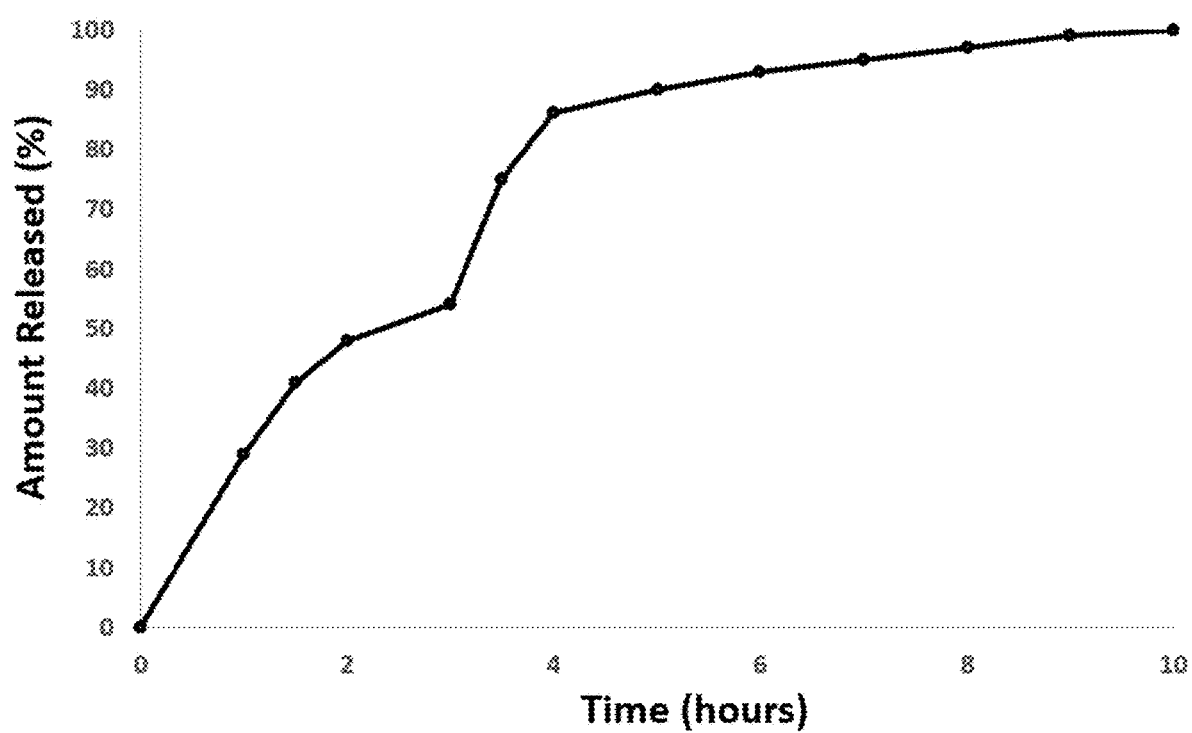
FIG. 2 is a graph reporting an example dissolution profile of cumulative release of % total THC dose versus time in hours of an example 2-pulse oral pharmaceutical composition tablet.

FIG. 2 is a graph reporting the dissolution profile of cumulative release of % total THC dose versus time in hours of the example 2-pulse oral pharmaceutical composition tablet. 50% of the total dose of the THC API was released after about 2 hours, and 90% of the total dose of THC API was released after about 5 hours.

Example 4. Effects of a Tablet Combining THC with CBN on Staying Asleep

Cannabis as a sleep improvement solution has been receiving increased attention, in light of the current legalization of Cannabis for medical use in 33 states and Washington DC. The influence of delta-9 Tetrahydrocannabinol (THC) combined with cannabinol (CBN) on sleep is preliminary, but pre-clinical research indicates that CBN may prolong sleep and be particularly effective when combined with other cannabinoids (Yoshida et al., 1995; Russo, 2011). The aim of the study in this Example was to evaluate the impact of a combination of 10 mg THC and 5 mg CBN in a pulse-release tablet on the ability for participants (medical Cannabis users) to stay asleep. The effect of the combination tablet was evaluated using objectively measured and self-reported data.

SleepScore Max® (Consumer Sleep Solutions LLC, Delaware) was used to measure objective sleep, and self-report questionnaires were used to measure perceived sleep. The SleepScore Max® device uses Ultra-Wideband Technology to track the subject's bodily gross and micro movements. SleepScore Max®, is a validated non-contact monitor designed to unobtrusively and objectively measure sleep at the user's home.

Objective data demonstrated that before using the combination tablet, participants slept 6 hours and 29 minutes on average, whereas during the combination tablet use period participants slept 20 minutes longer (6 hours and 49 minutes) on average ($p<0.001$; 5% improvement). Participants reported a 22% improvement in feeling well-rested in the morning ($p<0.0001$), with an average rating of 53.32 before product use and a rating of 65.21 during product use. Finally, participants reported an 18% increase in overall sleep quality ($p<0.0001$), going from an average of 57.36 before product use to 67.90 during product use.

This validation study found that the example dosage form combining THC with CBN was associated with improved sleep in a sample of medical Cannabis users. This was demonstrated using both objective sleep data using validated SleepScore® (Consumer Sleep Solutions LLC, Delaware) technology, and self-reported data.

The cultivation and use of the Cannabis plant for its medicinal and industrial benefits date back to ancient times. The use of Cannabis as a method to improve sleep has been receiving increased attention, in light of the current legalization of Cannabis for medical use in 33 states and Washington DC (NCSL, 2020). Recent studies indicate that individuals using Cannabis expect it to decrease their sleep-related problems (Altman et al., 2019) and are likely to reduce their use of sleep medications (Piper et al., 2017). Participants in the study by Altman and colleagues (2019) reported that using Cannabis helped them fall asleep about 15 minutes faster and sleep for about 2 hours longer. However, further research is needed to understand the objective and perceived effects of cannabinoids on sleep.

Delta-9 tetrahydrocannabinol (THC) is one of the most widely studied cannabinoids, but reviews of the scientific literature (Gates et al., 2014; Babson et al., 2017) document that its effects on sleep are not yet well understood. An early study by Cousens and DiMascio (1973) found that THC decreased time to fall asleep, measured objectively, but led to a "hangover" after-effect (i.e., continued effects, e.g. a continued "high" the following day). However, Chait (1990) found that THC was not associated with hangover effects. Other early studies suggested that THC might reduce REM sleep duration (Pivik et al., 1972; Feinberg et al., 1975) and increase deep sleep duration (Pivik et al., 1972; Barratt et al., 1974).

Recent research has benefited from a more sophisticated understanding of THC and sleep relative to earlier eras. Nonetheless, the optimal concentration, dosage, timing, and route of administration remain unknown (Babson et al., 2017). Given these complexities and more, it has been noted in the scientific literature that laboratory studies do not reflect people's naturalistic experiences of *Cannabis* use and sleep (Bowles et al., 2017). The current study categorized sleep into four commonly known stages including light sleep, deep sleep, rapid eye movement (REM), and wake.

Materials and Methods

Participants

Curio Wellness, LLC recruited medical *Cannabis* patients, certified by the Maryland Medical *Cannabis* Commission, who self-identified as experiencing insomnia, in particular the subjects in this study felt they had trouble staying asleep. Eligible participants were asked to visit Curio Wellness dispensary in person on two occasions. During the second visit, they picked up the *Cannabis* pulse-release dosage and reviewed the study instructions.

Forty-one people who met all eligibility criteria were recruited for participation. All participants signed an informed consent form prior to beginning the study, informing them of potential risks and benefits as well as other information about the voluntary study. Participants were given a $100 gift card upon completion of the study.

Design

A non-counterbalanced, pre-post study design was used. A placebo-controlled trial was preferred, however due to the State of Maryland labeling requirements for medical *Cannabis* products, this was not possible. Instead, the investigators decided a pre-product use period to establish sleep performance using SleepScore® would establish a baseline for comparison when treated with the pulse-release dosage form. Both quantitative and qualitative self-report data, as well as objective sleep data, were collected. During the first visit, study participants reviewed and signed informed consent, picked up the SleepScore Max® device, downloaded the research version of the SleepScore Max® companion app, and reviewed the study instructions. The product was tested in-home, giving the advantage of providing insight into the effectiveness of the product under real-life conditions and hence yielding more ecologically valid results.

An overview of the timeline is displayed in FIG. 3. The pre-product use period consisted of 3 weeks during which participants were instructed to track their sleep every night using SleepScore Max and complete a brief daily questionnaire each morning. During this period, participants had not yet received the test product. The product use period consisted of 3 weeks during which participants were asked to use the test product every night, track their sleep with SleepScore Max every night, and complete a brief daily questionnaire each morning. In addition to the brief daily questionnaires that were sent each morning, participants were asked to complete three more in-depth sleep experience questionnaires. The first of these sleep experience questionnaires was completed prior to product use, the second was completed after 1 week of product use, and the third was completed at the end of the study (after 3 weeks of product use).

Each study tablet contained 15 mg of total cannabinoids (10 mg of THC+5 mg of CBN). These specific concentrations are commercially available to medical *Cannabis* users in Maryland and were chosen for the current study based on previous research conducted by Curio Wellness. Tablets were a pulse-release dosage form as described in Example 1(a).

Participants were instructed to swallow the tablet up to 30 minutes before bed, every night for 3 weeks. Participants were also asked to discontinue use of any other medical *Cannabis* products 3 hours before going to bed, and to stop eating at least 2 hours before bed, during the 3 weeks of the product use period.

Objective sleep data were collected using a SleepScore Max® system, a non-contact monitor designed to unobtrusively and objectively measure sleep at the user's home. SleepScore Max® provides standard annotated 30 second epoch sleep stage data and commonly used sleep metrics such as time to fall asleep (sleep onset latency), number of awakenings, start and end of sleep sessions, and total sleep time. Time spent in light sleep, deep sleep, and REM sleep (e.g. in minutes) together add up to total sleep time. Wake after sleep onset describes the total number of minutes a person is awake after falling asleep for the first time and before waking up prior to getting up. The total time in bed describes the time between getting in and out of bed (from "lights out, start tracking session" to "lights on, stop tracking session" according to the SleepScore Max® app). With these measures, sleep efficiency and sleep maintenance can be calculated. Sleep efficiency (in %) is calculated by dividing total sleep time by time in bed. Sleep efficiency of 85% and higher is considered to reflect good sleep quality (Ohayon et al., 2017). Sleep maintenance (in %) describes the ability of staying asleep once asleep, taking into account waking up too early (before getting out of bed) and/or struggling to get back to sleep (but not the time it takes to fall asleep initially) and is calculated by dividing total sleep time by the sum of the duration of all sleep stages, including wake, after initially falling asleep. Also, all four relative stage durations (% Light, % Deep, % REM, and % Wake) were calculated by dividing stage duration by the sum of the duration of all sleep stages, including wake, after initially falling asleep.

Validity of these sleep measurements has been shown multiple times, with good performance compared to the gold standard sleep measurement technique of polysomnography (O'Hare et al., 2014; Zaffaroni et al., 2017; Schade et al., 2019; Zaffaroni et al., 2019). The SleepScore® technology can be compared to ultra-low energy radar. The sensitivity of the sensor and the performance of the signal processing algorithms allow the detection of gross body movement and full respiration patterns by measuring the micro motion of the chest cavity.

SleepScore Max® provided three sleep scores: SleepScore®, Body Score, and Mind Score. These are normalized 100-point sleep quality scales, based on proprietary algorithms, using scientific averages for a user's age and gender (Ohayon et al., 2004). SleepScore® is defined by six sleep parameters (total sleep duration, time to fall asleep, time in light sleep, time in deep sleep, time in REM, and number of awakenings throughout the night) and can be regarded as a general sleep quality scale. Mind Score reflects the amount of REM sleep, which is known to play an important role in creative thinking, problem solving, and emotional processing. Body Score reflects the amount of deep sleep, which is considered restorative sleep and is linked to the perception of feeling well-rested the next day.

Participants used the research version of the SleepScore Max® companion app, called Max R. Max R is a slimmed down version of the publicly available SleepScore Max® app, dedicated to serve as a sleep recording device, and available for researchers at request. Max R sleep recorder tracks sleep in the same way as the publicly available app, but it does not display sleep data and does not offer consumer features such as the sleep guide or smart alarm. It simply acts as a sleep tracker.

Brief daily questionnaires were sent each morning using Survey Monkey to check compliance with sleep tracking, check compliance with use of the pulse-release dosage during the product use period, and measure perceived sleep (e.g., "How long did you feel it took to fall asleep last night?"). These brief daily questionnaires were administered during the entire 6-week study, both before and during product use.

Nightly objective sleep data and daily self-report data were analyzed in R (version 3.5.2) using multilevel regression analyses, taking into account the nested structure of the data (nights within subjects). An alpha level of 0.05 was used. For the objective sleep data, analyses compared nights in the pre-product use period on which participants tracked their sleep to nights in the product use period on which participants tracked their sleep and reported using the test product. For the daily self-report data, analyses compared nights in the pre-product use period on which participants provided responses to nights in the product use period on which participants provided responses and reported using the test product.

MS Excel (version 1901, for Windows) was used to analyze the quantitative self-report sleep data from the sleep experience questionnaires. Descriptive statistics and one-tailed, paired-samples t-tests were conducted, using an alpha level of 0.05. Analyses compared responses to the sleep experience questionnaire administered before product use to the subsequent sleep experience questionnaires.

Results

Of the 41 participants who were recruited into the study, 1 did not register a SleepScore Max® account and 2 chose to withdraw. Of those who withdrew from the study, one cited a preexisting medical condition and the other experienced technological difficulties. In addition, a few individuals remained in the study but did not provide complete data. Therefore, due to missing SleepScore Max® data, the objective sleep analyses included 35 participants. Similarly, due to missing survey data, the perceived sleep analyses included self-report data from 35 participants.

Demographics

The average age of study participants was 47, ranging from 22 to 69. The sample was 57% female. Over three-quarters (77%) described their race as White, and over half (54%) were married. The majority (57%) were working full-time, and 63% had finished college or earned graduate degrees. Annual household income ranged from less than $20,000 (3%) to $100,000 or higher (40%).

Figure 4:
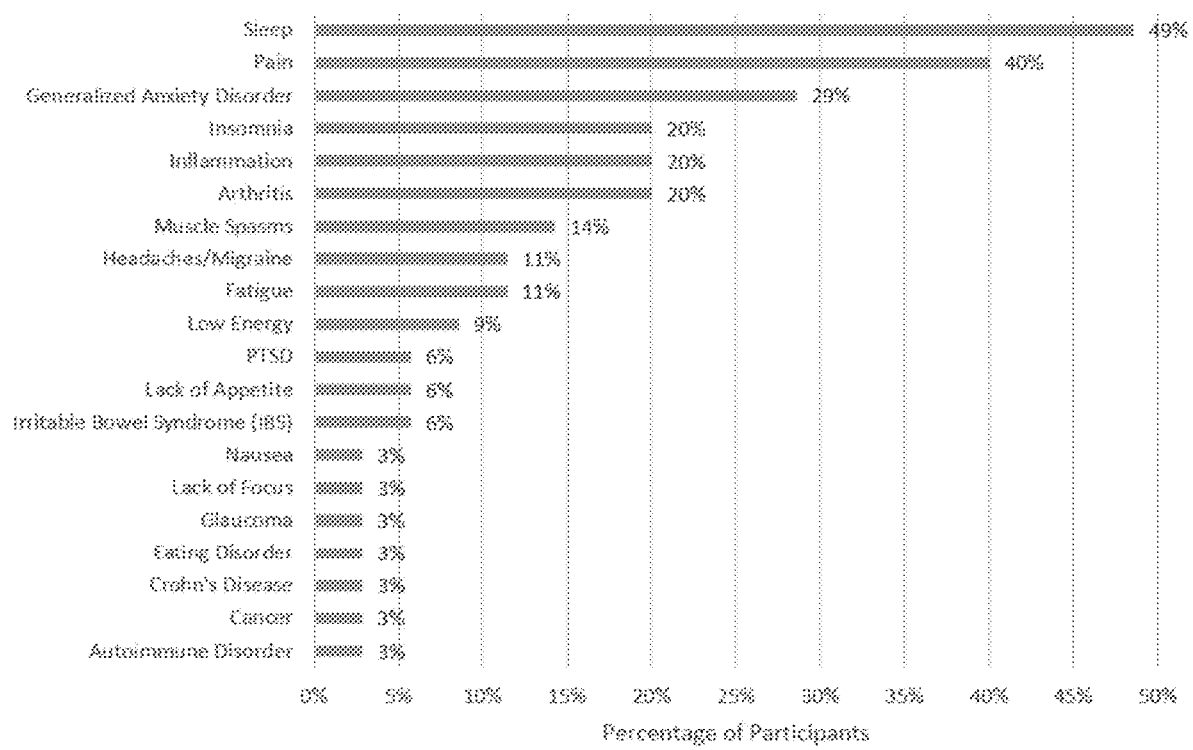
FIG. 4 is a graph reporting example medical conditions for which *Cannabis* was used. Up to 3 conditions could be selected by each participant.

At the beginning of the study, the most common medical conditions for which participants reported using Cannabis were sleep/insomnia (69%), pain (40%), and generalized anxiety disorder (29%). Full results summarizing the medical conditions for which participants reported using Cannabis are shown in FIG. 4.

Figure 5:
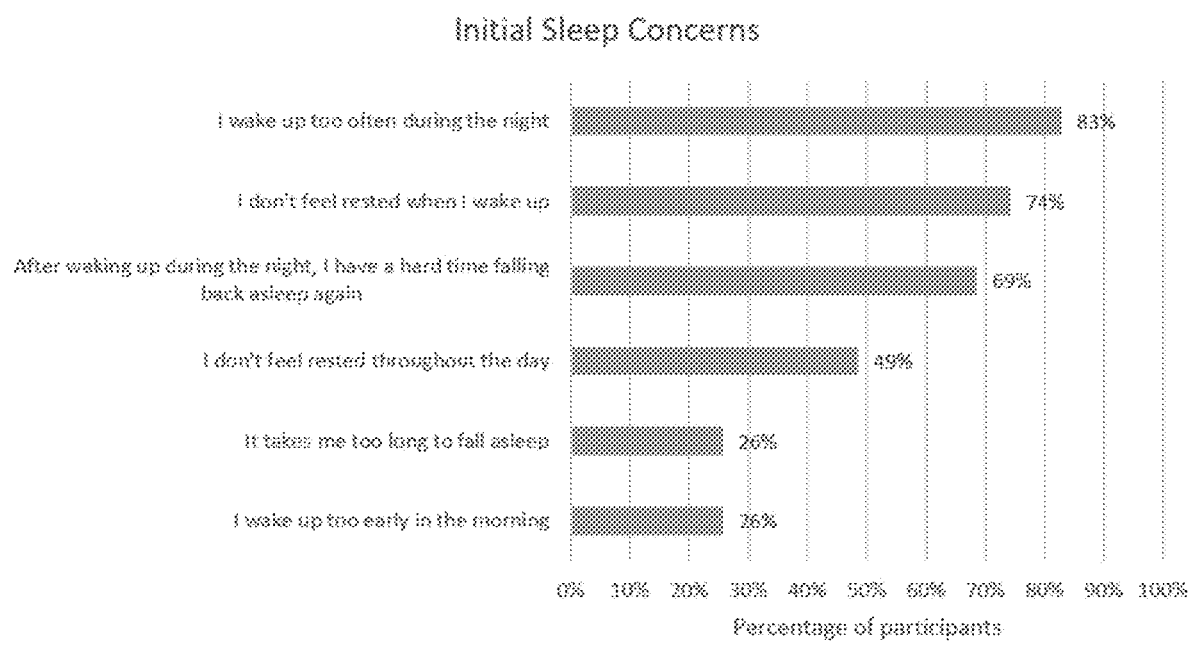
FIG. 5 is a graph reporting example sleep concerns of clinical trial participants prior to using an example pulse-release dosage form of the present disclosure. Percentages do not total 100 because multiple answers were allowed.

Participants' sleep concerns during the weeks before product use are shown in FIG. 5. The most common answer (83%) was waking up too often in the night, followed by not feeling well rested when waking up in the morning (74%). In addition, about one quarter (26%) reported taking too long to fall asleep and waking up too early in the morning. The finding that concerns about being able to stay asleep during the night outweighed concerns about being able to fall asleep confirms that the participants who were recruited for the current study were an appropriate match for the product being tested.

Figure 6:
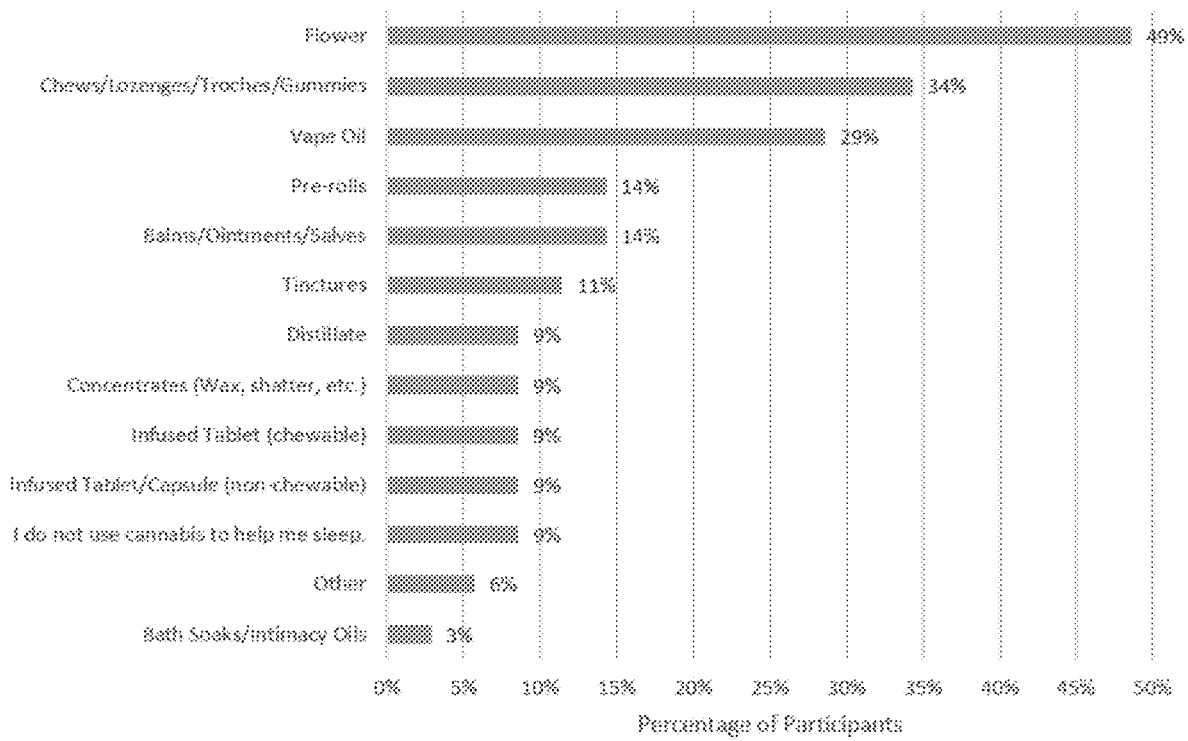
FIG. 6 is a graph reporting example forms of *Cannabis* being used by clinical trial participants to help with sleep prior to the product use period. Percentages do not total 100 because multiple answers were allowed.

Participants were asked whether medical Cannabis made them feel sleepy; 89% replied yes and 11% replied no. They reported using a variety of forms of Cannabis in the past to help with sleep. The most common form used was flower (49%). Full results summarizing forms of Cannabis study participants had used in the past to help with sleep are shown in FIG. 6.

Results of the objective sleep analyses are shown in Table 1. These results revealed that treatment effects on parameters of wake after sleep onset, number of awakenings, sleep efficiency, and sleep maintenance were not significant. Nor was there a significant change in time to fall asleep. However, participants' average length of time in bed increased by 22 minutes ($p<0.001$; 5% improvement), leading to a healthier amount of sleep. Before using the test product, study participants slept 6 hours and 29 minutes on average, whereas during the product use period they slept 20 minutes longer (6 hours and 49 minutes) on average ($p<0.001$; 5% improvement). This increase in total sleep time translated into more light sleep, both in duration ($p<0.001$; 7% increase) and proportion of time ($p=0.02$). Taken together, these changes indicate improved sleep, reflected in a significant increase in SleepScore. Prior to using the test product, participants had an average SleepScore of 78.98. While using the test product, average SleepScore rose to 80.21 ($p=0.03$; 2% increase), which is similar to the average SleepScore for SleepScore Max® users in the same age group as the study sample. Objective sleep and multilevel regression results comparing nights before product use to nights during product use for n=35 (n=1020 nights) are presented in Table 1.

TABLE 1

Objective Sleep Analyses Sleep Score: Baseline Treatment Effect vs. Baseline.

| | Observed | | Estimated | | |
|---|---|---|---|---|---|
| | Pre-test Period (Baseline) | Product Use | Constant | beta | p-value |
| SleepScore (0-100) | 78.98 | 80.21 | 79.04 | 1.232 | 0.033 |
| BodyScore (0-100) | 76.50 | 76.66 | 76.50 | 0.081 | 0.451 |
| MindScore (0-100) | 78.18 | 79.87 | 78.26 | 1.479 | 0.055 |
| Total Sleep Time (minutes) | 388.91 | 408.96 | 389.30 | 20.719 | <0.001 |
| Sleep Onset Latency (minutes) | 21.58 | 24.94 | 21.58 | 2.655 | 0.051 |
| Number of Awakenings | 4.78 | 4.94 | 4.78 | 0.214 | 0.069 |
| Wake After Sleep Onset (minutes) | 43.43 | 44.36 | 43.57 | 1.506 | 0.225 |
| Time in Bed (minutes) | 460.35 | 482.22 | 460.66 | 22.917 | <0.001 |
| Sleep Efficiency | 84.26 | 83.76 | 84.22 | −0.396 | 0.256 |

TABLE 1-continued

Objective Sleep Analyses Sleep Score: Baseline Treatment Effect vs. Baseline.

|  | Observed | | Estimated | | |
|---|---|---|---|---|---|
|  | Pre-test Period (Baseline) | Product Use | Constant | beta | p-value |
| Sleep Maintenance | 84.43 | 84.41 | 84.40 | −0.154 | 0.396 |
| Light (minutes) | 240.49 | 256.36 | 240.75 | 17.003 | <0.001 |
| REM (minutes) | 76.58 | 79.74 | 76.79 | 2.474 | 0.096 |
| Deep (minutes) | 71.84 | 72.86 | 71.76 | 1.170 | 0.241 |
| % Light sleep | 55% | 56% | 55% | 0.983 | 0.018 |
| % REM sleep | 18% | 17% | 18% | −0.276 | 0.234 |
| % Deep sleep | 17% | 17% | 17% | −0.610 | 0.067 |
| % Wake after sleep onset | 10% | 10% | 10% | −0.106 | 0.399 |

For pre-test period and the product use period, each average was calculated by averaging nights across participants, and then averaging those participants' averages to a single simple average, listed under "Observed" in the Table 1. Listed under "Estimated" in Table 1 are the outcomes of the multilevel regression analyses. Regression model was as follows: Sleepmeasure$_{ij}$=Const0$_{ij}$+B*TestPeriod$_{ij}$; TestPeriod coded as 0 for the observations during nights when participants were not using the pulse-release dosage, and 1 for nights when participants tracked their sleep and reported using the pulse-release dosage. Nights during the product use period in which participants did not have objective data or did not report using the pulse-release dosage were not included in analyses.

Analyses of the daily self-report data suggested that the pulse-release dosage helped participants experience better sleep. Analyses of the daily self-report data suggested that the test product helped participants experience better sleep. Participants perceived fewer nighttime awakenings after falling asleep, going from 2.87 before product use to 2.33 during product use (p<0.0001; 19% decrease). They also reported getting out of bed fewer times, from 1.21 before product use to 0.95 during product use (p<0.0001; 21% decrease). In addition, participants reported a 22% improvement in feeling well-rested in the morning (p<0.0001), with an average rating of 53.32 before product use and a rating of 65.21 during product use. Participants reported a 18% increase in overall sleep quality (p<0.0001), going from an average of 57.36 before product use to 67.90 during product use. See Table 2.

For pre-test period and the product use period, each average was calculated by averaging nights across participants, and then averaging those participants' averages to a single simple average, listed under "Observed" in Table 2.

Overall, study participants reported feeling more satisfied with their sleep and felt better in the morning. Before using the product, they woke up feeling rested only 2 mornings per week. By the end of the study, this had increased to 4 mornings per week. They reported napping less often during the day, presumably because they were sleeping much better at night. These effects all were shown after 1 week of using the product and were sustained through the end of the study (3 weeks of product use).

The results of the daily questionnaires were confirmed by significant sleep improvements that were observed when comparing the sleep experience questionnaires. The first of these sleep experience questionnaires was completed before the product use period, the second was completed after 1 week of product use, and the third was completed at the end of the study (after 3 weeks of product use). First, to test for a 1-week effect, we compared participants' perceptions of their sleep after 1 week of using the product to how they perceived their sleep before using the product. Significant improvements were found for number of awakenings, time awake during the night after falling asleep, total sleep time, feeling well-rested in the morning, overall sleep satisfaction, and frequency of daytime napping. Next, to test for a 3-week effect, participants' perceptions of their sleep at the end of the study were compared to how they perceived their sleep before using the product. All significant effects noted at 1 week were sustained at 3 weeks: number of awakenings,

TABLE 2

Self-report daily questionnaire and multilevel regression results comparing nights before product use to nights during product use for n = 35 (n = 1236 nights).

|  | Observed | | Estimated | | |
|---|---|---|---|---|---|
|  | Pre-test Period | Product Use | Constant | beta | p-value |
| Bedtime Sleepiness (0-100) | 65.71 | 67.02 | 65.74 | 1.293 | 0.103 |
| Time to Fall Asleep (minutes) | 24.58 | 24.25 | 24.37 | 0.059 | 0.482 |
| Number of Awakenings | 2.87 | 2.33 | 2.86 | −0.531 | <0.0001 |
| Number of Times Out of Bed | 1.21 | 0.95 | 1.21 | −0.256 | <0.0001 |
| Well-rested in the Morning (0-100) | 53.32 | 65.21 | 53.38 | 11.922 | <0.0001 |
| Sleep Quality (0-100) | 57.36 | 67.90 | 57.43 | 10.59 | <0.0001 | time awake during the night after falling asleep, total sleep time, feeling well-rested in the morning, overall sleep satisfaction, and frequency of daytime napping. Details are presented in FIG. 7 to FIG. 12.

Figure 7:
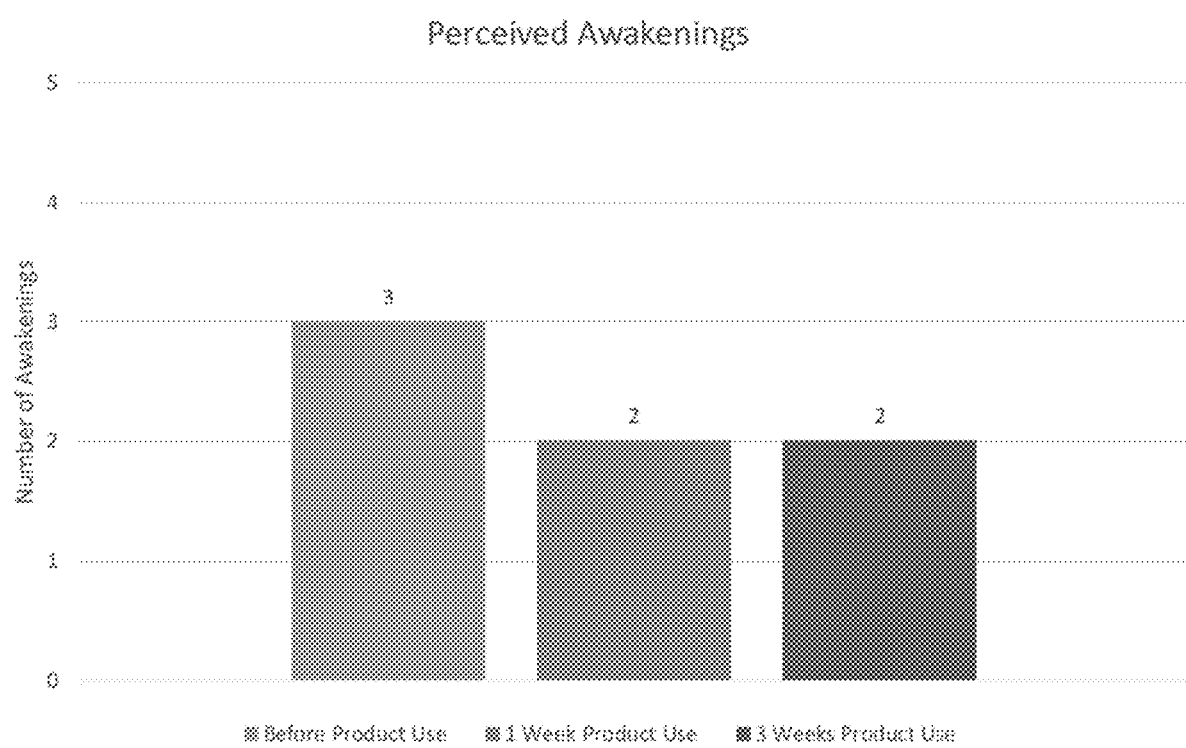
FIG. 7 is a graph reporting example data on self-reported average number of times participants woke up per night.
Figure 8:
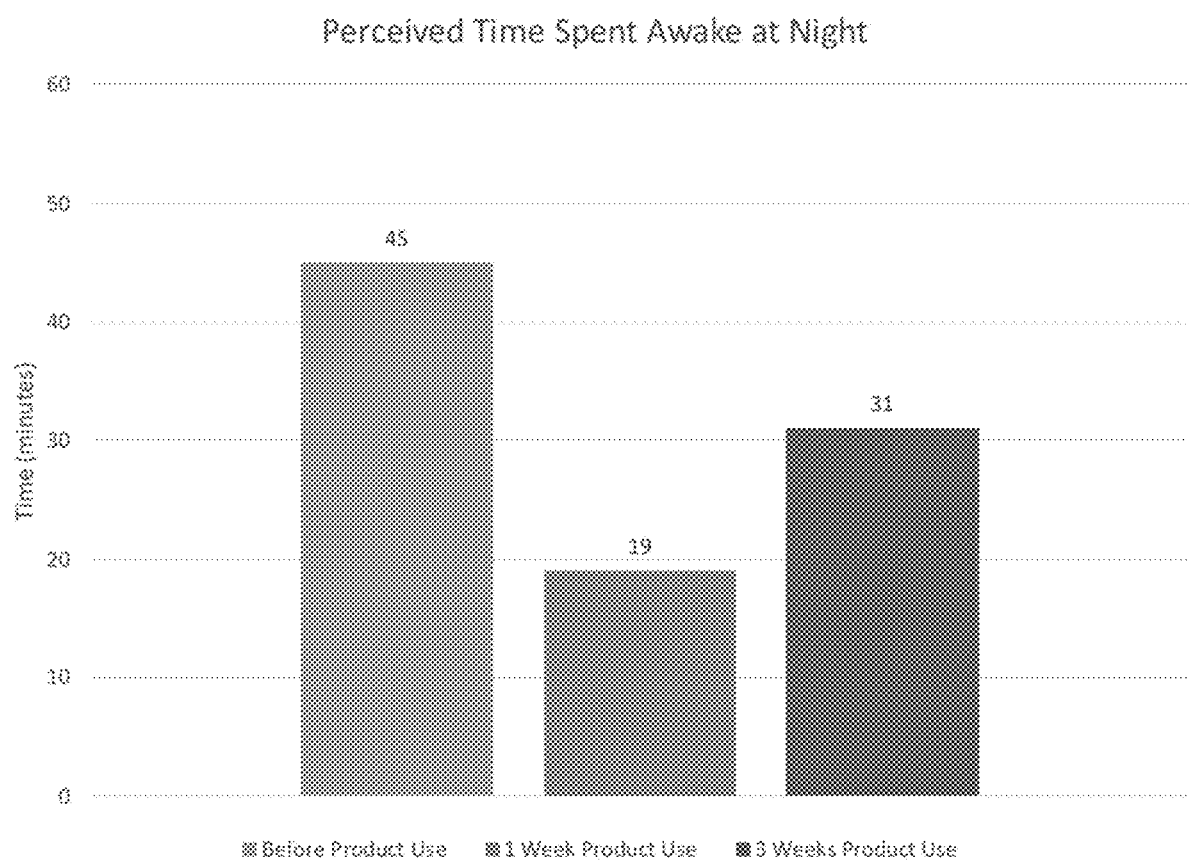
FIG. 8 is a graph reporting example self-reported average amount of time per night spent awake after initially falling asleep.
Figure 9:
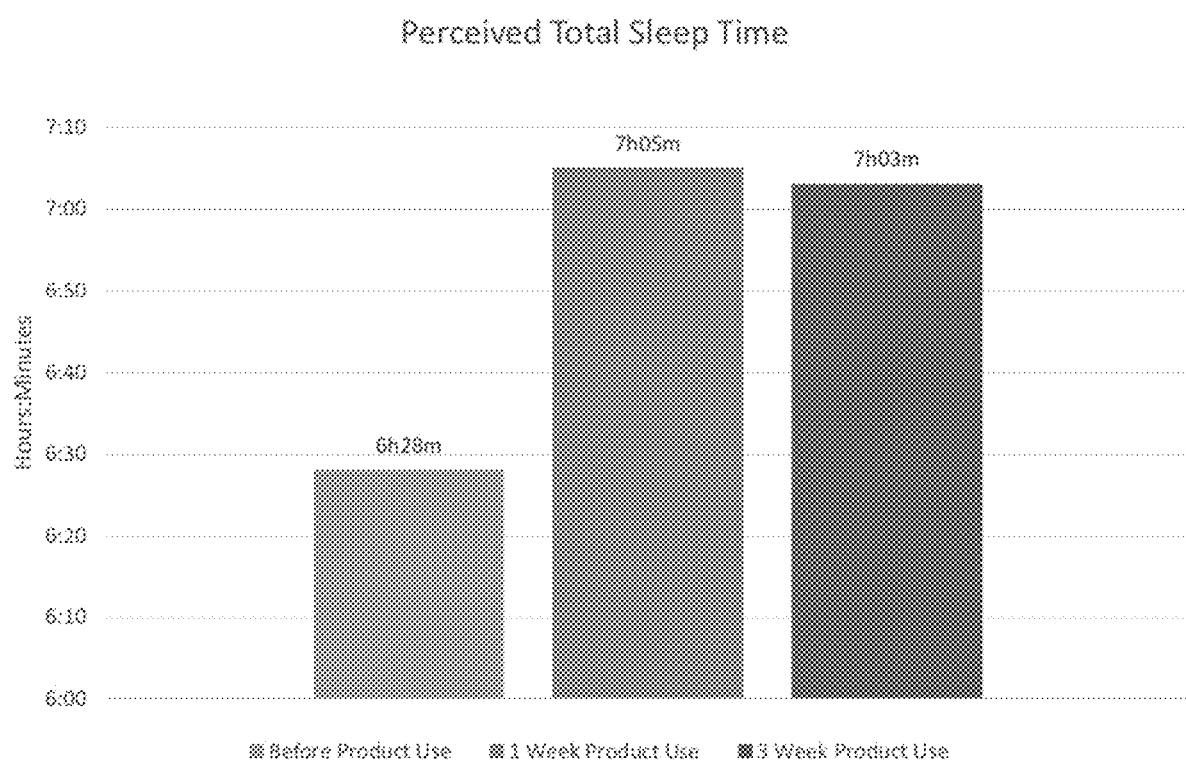
FIG. 9 is a graph reporting example self-reported average number of hours and minutes slept per night.
Figure 10:
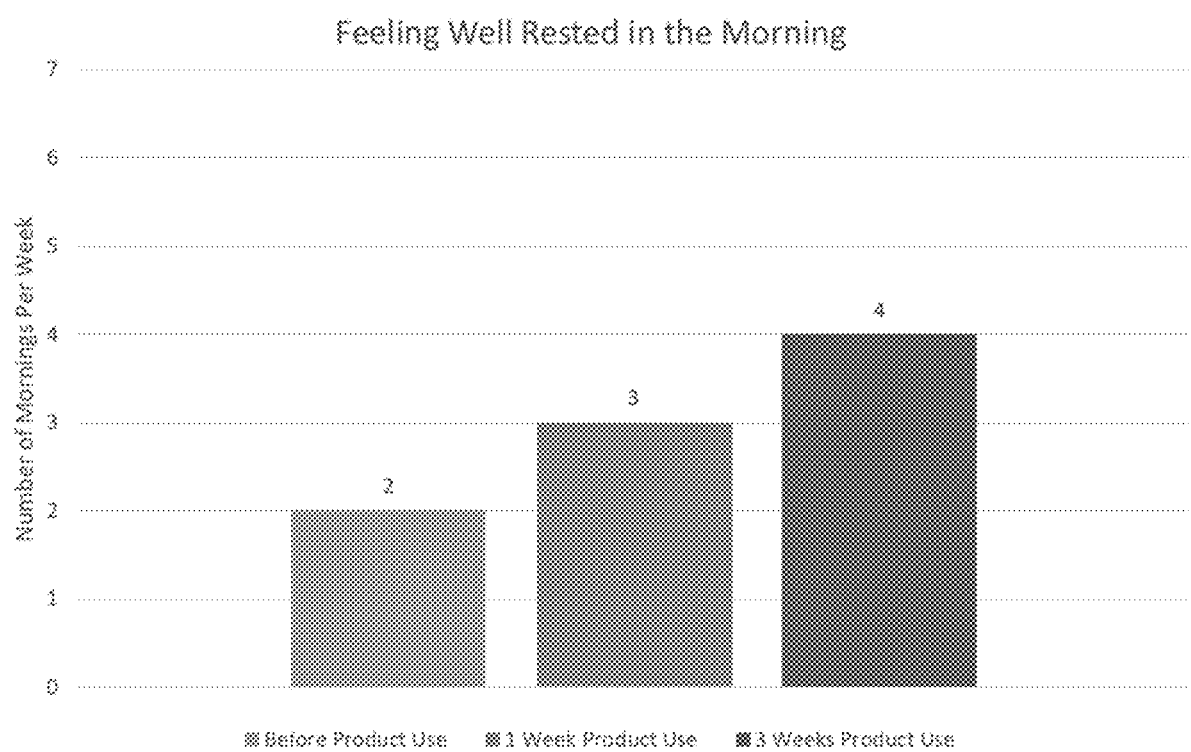
FIG. 10 is a graph reporting example self-reported number of mornings per week participants woke up feeling well rested.
Figure 11:
FIG. 11 is a graph reporting example self-reported number of nights per week participants felt satisfied with their sleep.
Figure 12:
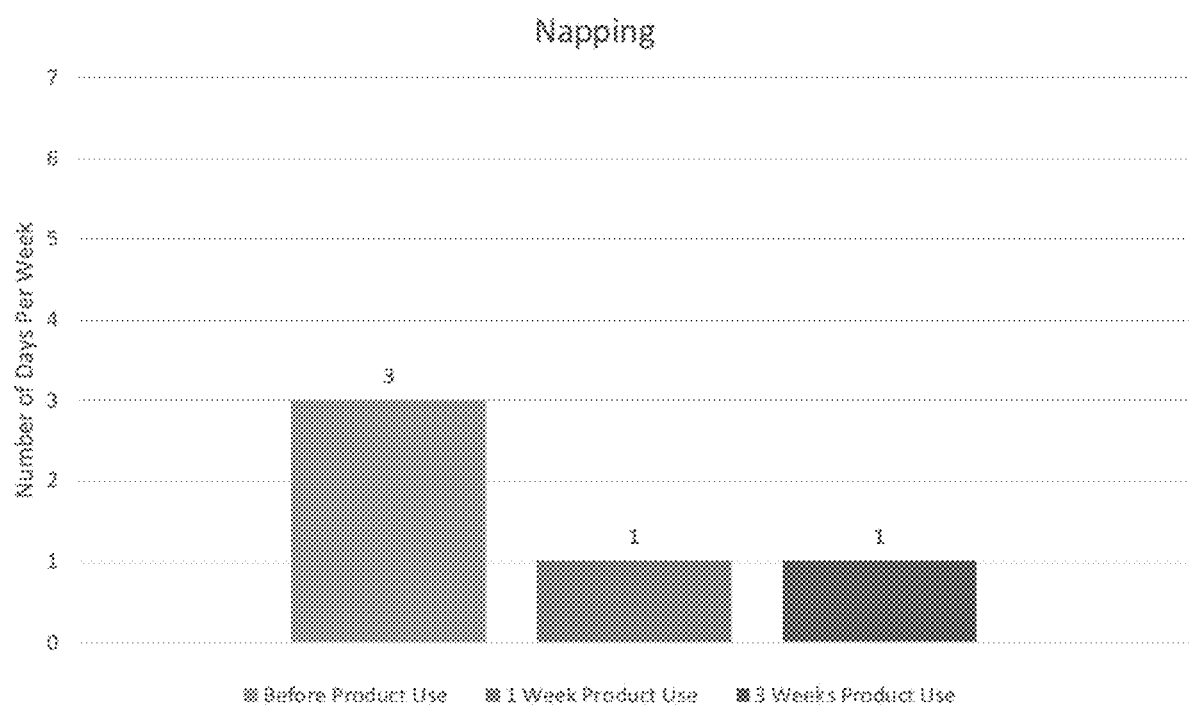
FIG. 12 is a graph reporting example self-reported number of days per week participants napped.

As shown in FIG. 7, participants felt they woke up less often during the product use period. Before using the product, they reported waking up 3 times per night on average. This decreased to 2 times per night after 1 week of using the product (p=0.009) and stayed at 2 times per night after 3 weeks of using the product (p=0.007). As shown in FIG. 8, participants felt they spent less time awake at night (after falling asleep initially) during the product use period. There was a 26-minute decrease in perceived amount of time awake after 1 week of using the product (p=0.005). After 3 weeks of product use, there was a 14-minute decrease compared to when participants were not using the product (p=0.03). As shown in FIG. 9, participants felt they slept more during the product use period. There was a 37-minute increase in perceived nightly total sleep time after 1 week of using the product (p<0.001). After 3 weeks of product use, there was a 35-minute increase compared to when participants were not using the product (p<0.001). As shown in FIG. 10, participants felt more well rested upon waking in the morning during the product use period. Before using the product, they woke up feeling rested only 2 mornings per week. This increased to 3 mornings per week after 1 week of product use (p<0.001) and 4 mornings per week after 3 weeks of product use (p<0.001). As shown in FIG. 11, participants were more satisfied with their sleep during the product use period. Before using the product, they reported feeling satisfied 3 nights per week. This increased to 4 nights per week after 1 week of product use (p=0.003) and remained at 4 nights per week after 3 weeks of product use (p=0.004). As shown in FIG. 12, participants reduced their frequency of taking daytime naps during the product use period. Before using the product, they reported napping 3 days per week. This decreased to only 1 day per week after 1 week of product use (p<0.001) and continued to be only 1 day per week after 3 weeks of product use (p<0.001). Due to the State of Maryland labeling requirements for medical Cannabis products, a placebo controlled trial was not possible regarding the conduct of this study.

The timing of this study unexpectedly coincided with the COVID-19 pandemic. Given that the study design did not include a control group, the extent to which the effects were caused by the Cannabis pulse-release dosage versus health and lifestyle changes associated with the COVID-19 pandemic cannot be fully known. Data collection occurred from February 24 to April 5. Maryland's stay-at-home directive was not ordered until Mar. 30, 2020 (Wenger & Wood, 2020), but closures of non-essential business, school closings, and other restrictions began earlier (Dance, 2020). The increase in total sleep time found in the current study sample is in the same direction as national SleepScore® data from March 16-Apr. 3, 2020, showing that, on average, people in the United States spent more time in bed and slept longer during COVID-19 restrictions compared to before (SleepScore Labs, 2020).

Discussion

In summary, the validation study in this Example evaluated the effectiveness of a pulse-release oral dosage form product combining THC with CBN to improve ability to stay asleep. Medical Cannabis patients certified by the Maryland Medical Cannabis Commission who felt they had trouble staying asleep were recruited by Curio Wellness into the study. The research participants tracked their sleep for 3 weeks and then tested the product for 3 weeks in their own homes while continuing to track their sleep. This way of testing has the advantage of providing insight into the effectiveness of the product under real-life conditions and hence yielding more ecologically valid results.

The tablets were administered as a pulse-release dosage form: the dosage form was designed so that half of the dosage was released immediately after oral administration, and the remaining half was released 2-3 hours later. The study in this Example found that an example product combining THC with CBN was directly associated with both improved objective and perceived sleep quality and duration in a sample of medical Cannabis users.

Example 5. Effects of a Tablet Combining THC with CBN on Falling Asleep

This Example describes a study evaluating the impact of a combination of 10 mg THC and 5 mg CBN in an immediate-release sublingual tablet on the ability for participants (medical Cannabis users) to fall asleep. The effect of the combination tablet was evaluated using objectively measured and self-reported data.

The combination cannabinoid tablet was tested in 28 medical Cannabis patients certified by the Maryland Medical Cannabis Commission who felt they had trouble falling asleep, covering 445 nights of use of the product.

Analysis of the objective sleep data indicated that use of the falling asleep tablet was unexpectedly associated with a statistically significant increase in how long it took to fall asleep. Participants' average sleep onset latency slightly rose from 24 minutes without intervention to 26 minutes when using the falling asleep tablet. In addition to the effect on falling asleep, the objective sleep data also showed small but significant declines in sleep efficiency (−1%) and sleep maintenance (−1%), both outcome measures reflecting the ability to spend time in bed asleep rather than awake.

Mirroring the objective data, the self-report data did not show improvement in how many minutes participants felt it took them to fall asleep. Perceived sleep onset did not change significantly across the daily questionnaires or the three sleep experience questionnaires. However, there was significant improvement in how often participants felt that they fell asleep within their preferred amount of time, going from an average of 3 nights per week to 4 nights per week.

Despite the lack of improvement in falling asleep faster, participants reported that the product helped their sleep in many other ways. At the end of the study, they felt sleepier at bedtime, felt more rested in the morning, and were more satisfied with their sleep, compared to the weeks before using the test product. They also felt they woke up less often and got out of bed less often during the night. In addition, participants reported a significant decrease in how often feelings of sleepiness affected their school, work, or private life.

Materials and Methods

Participants

Curio Wellness recruited medical Cannabis patients, certified by the Maryland Medical Cannabis Commission, who self-identified as experiencing insomnia, in particular the subjects in this study felt they had trouble falling asleep. Curio Wellness obtained informed consent from all participants and provided them with the Cannabis test product, a SleepScore Max® device, a guide for using the research version of the SleepScore Max® companion app, and additional study instructions.

To be considered for participation, the medical *Cannabis* patients had to be at least 21 years old and willing to track their sleep every night for 6 weeks. They also had to be willing to use the test product every night for 3 weeks, and willing to discontinue other *Cannabis* use at least 3 hours before bed during the product use period.

In order to test the product in a sample of otherwise healthy users, people with other sleep disorders (e.g., narcolepsy, restless leg syndrome, sleep apnea) or psychological disorders affecting sleep (e.g., clinical depression, bipolar disorder, schizophrenia) were excluded. People taking sleep medications (prescription or over-the-counter) or anticonvulsant medications were excluded, as were people who typically had 3 or more alcoholic beverages on 4 or more nights per week. Women who were pregnant, lactating, or planning to become pregnant in the next 2 months were excluded. Other exclusion criteria included being a shift worker, having a child at home under 12 months old, or planning to travel across multiple time zones or be away from home for more than 5 days during the entire study.

35 people who met all eligibility criteria were recruited for participation. All participants signed an informed consent form prior to beginning the study, informing them of potential risks and benefits as well as other information about the voluntary study. Participants were given a $100 gift card upon completion of the study.

Study Design

A non-counterbalanced, pre-post study design was implemented. Participants were aware of the sleep benefit of the intervention. Both quantitative and qualitative self-report data, as well as objective sleep data, were collected. The data collection period of the study was executed from March 23-May 3, 2020. The product was tested in-home, giving the advantage of providing insight into the effectiveness of the product under real-life conditions and hence yielding more ecologically valid results. An overview of the timeline is displayed in FIG. 13

The pre-product use period consisted of 3 weeks during which participants were instructed to track their sleep every night using SleepScore Max® and complete a brief daily questionnaire each morning. During this period, participants had not yet received the test product.

The product use period consisted of 3 weeks during which participants were asked to use the test product every night, track their sleep with SleepScore Max® sleep measurement system every night, and complete a brief daily questionnaire each morning.

In addition to the brief daily questionnaires that were sent each morning, participants were asked to complete 3 longer surveys. The first of these sleep experience questionnaires was completed prior to product use, the second was completed after 1 week of product use, and the third was completed at the end of the study (after 3 weeks of product use).

Procedures

Participants were provided with instructions on how to set up and use SleepScore Max® and the companion app. Detailed instructions for using the test product were reviewed with each participant by a Curio Wellness study staff member. Participants were asked to discontinue use of any other medical *Cannabis* products 3 hours before going to bed, and to stop eating at least 2 hours before bed, during the 3 weeks of the product use period. They were instructed to take 1 tablet 15 to 30 minutes before bed, every night for 3 weeks.

*Cannabis* Test Product

Each tablet contained 15 mg of total cannabinoids (10 mg of THC+5 mg of CBN). These specific concentrations are commercially available to medical *Cannabis* users in Maryland and were chosen for the current study based on previous research conducted by Curio Wellness. The tablet form was dissolvable immediate release, and the delivery method was sublingual.

Measures

For this study, both objective and self-report sleep data were collected.

Sleep Tracking

Objective sleep data were collected using SleepScore Max® as described in Example 4.

Questionnaires

Self-report data were collected as described in Example 4.

Data Analyses

Data analyses were performed as described in Example 4.

Results

Of the 35 individuals who were recruited into the study, one withdrew due to illness. Another participant reported technological difficulties, and some remained in the study but did not provide complete data. Therefore, due to missing SleepScore Max® data, the objective sleep analyses included 28 participants. Similarly, due to missing survey data, the perceived sleep analyses included self-report data from 26 participants.

The 28 participants who consistently tracked their sleep did so for 79% of all nights in the study. There were 481 nights of tracked sleep before test product use and 445 nights during which participants used the test product and tracked their sleep (76% compliance rate for both activities during product use).

Across the sample of 28 participants who consistently provided daily self-report data, there were 982 daily questionnaire responses (84% response rate). Participants reported using the test product for 86% of nights during the product use period (but did not track their sleep on all of those nights). For the nights participants reported not using the test product, they stated reasons such as not sleeping at home that night, worry about not waking up on time the next morning, and having a cold. No one reported taking more than the recommended dose.

According to SleepScore Max® user registration data, the average age was 41, ranging from 24 to 71. Based on data collected in the first sleep experience questionnaire, 65% were female, 84% described their race as White, and over half (54%) were married. The majority (53%) were working full-time, and 43% had finished college or earned graduate degrees. Annual household income ranged from less than $20,000 (4%) to $100,000 or higher (34%).

Figure 14:
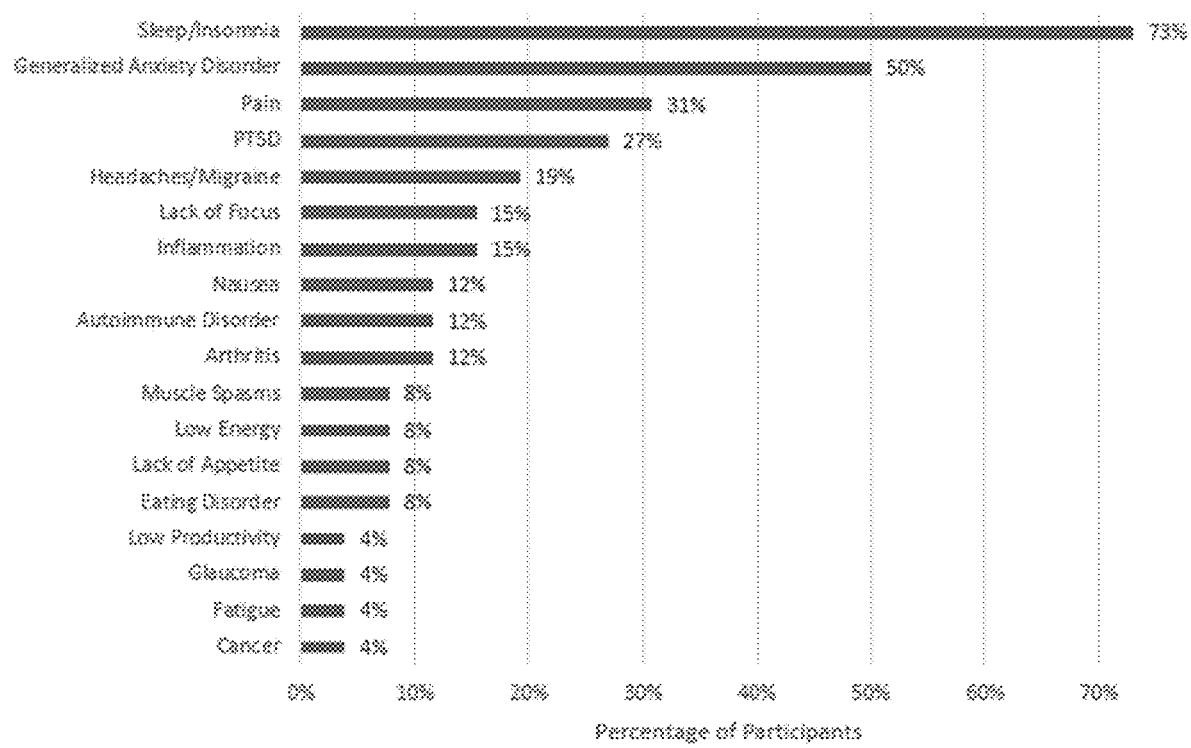
FIG. 14 is a graph reporting example medical conditions for which *Cannabis* was used. Up to 3 conditions could be selected by each participant.

At the beginning of the study, the most common medical conditions for which participants reported using *Cannabis* were insomnia (73%), generalized anxiety disorder (50%), and pain (31%). Full results are shown in FIG. 14.

Figure 15:
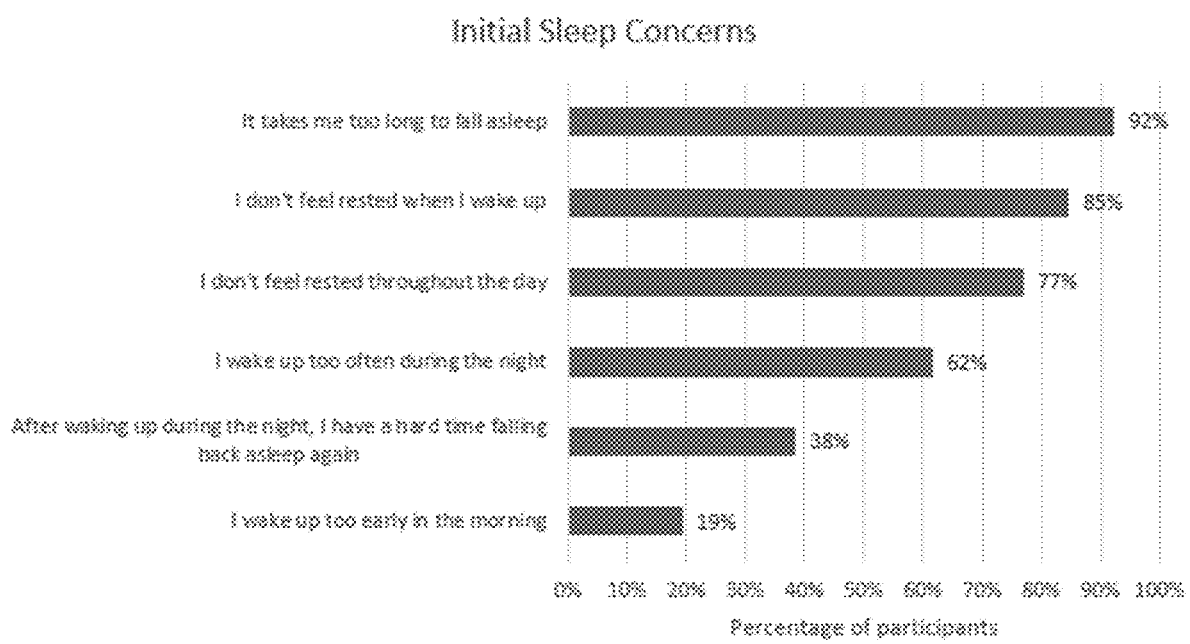
FIG. 15 is a graph reporting example sleep concerns of clinical trial participants prior to using an example pulse-release dosage form of the present disclosure. Percentages do not total 100 because multiple answers were allowed.

The most common sleep concern during the weeks before starting to use the falling asleep tablet was taking too long to fall asleep (92%), followed by not feeling well rested when waking up (85%) or throughout the day (77%). Full results are shown in FIG. 15. The finding that concerns about falling asleep outweighed other types of sleep concerns confirms that the participants who were recruited for the current study were an appropriate match for the product being tested according to their self-report.

Figure 16:
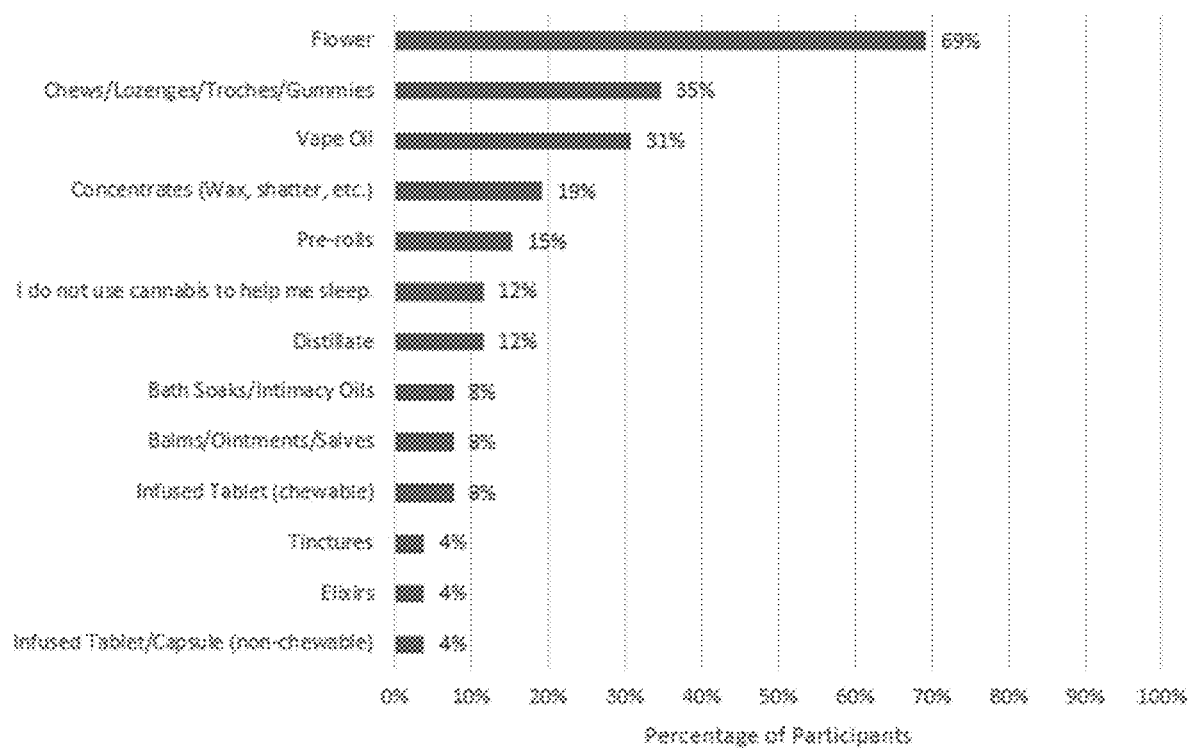
FIG. 16 is a graph reporting example forms of *Cannabis* being used by clinical trial participants to help with sleep prior to the product use period. Percentages do not total 100 because multiple answers were allowed.

Participants were asked whether medical *Cannabis* made them feel sleepy; 81% replied yes and 19% replied no. They reported using a variety of forms of *Cannabis* in the past to help with sleep. The most common form used was flower (69%). Full results are shown in FIG. 16.

Sleep Measured Objectively

Participants were recruited into the study based on self-reported difficulty falling asleep. Before product use, participants reported taking 37.50 minutes to fall asleep on average. However, objective sleep data collected before product use showed that they actually fell asleep in 23.56 minutes on average. This length of sleep onset time is longer than the average for SleepScore Max® users in the same age group as the study sample (20.58 minutes) but still within the range considered to be normal in the scientific and clinical sleep literature (less than 30 minutes; Edinger et al., 2004; Ohayon et al., 2017). In the current sample, during the period before using the product, on only 22% of nights did the participants take 30 or more minutes to fall asleep.

Therefore, it appears that there may have been little room for improvement in objective sleep onset in this sample.

Analysis of the objective sleep data indicated that the test product was unexpectedly associated with a statistically significant increase in how long it took to fall asleep (p=0.021). Before using the test product, as noted above, participants had an average sleep onset latency of 23.56 minutes. This average rose to 26.40 minutes during product use (12.05% increase). Related to the increased onset latency, a statistically significant decrease in sleep efficiency during the product use period (p=0.029) going from 84.39% before product use to 83.34% during product use (1.24% relative decrease) was observed. Similarly, sleep maintenance decreased (p=0.047), going from 84.50% before product use to 83.64% during product use (1.02% relative decrease). Taken together, these changes indicate that participants had a harder time falling asleep and staying asleep. See Table 3.

as 0 for the observations during nights when participants were not using the test product, and 1 for nights when participants tracked their sleep and reported using the test product. Nights during the product use period in which participants did not have objective data or did not report using the test product were not included in analyses.

Given these surprising results, additional analyses were performed to test whether effects would be observed in specific subgroups. An analysis was conducted to determine whether objective sleep improvement occurred in the subgroup of participants who began the study with the poorest sleep onset latency (objectively measured, above the sample median of 19.80; n=14). This subgroup had the most need for a product that could help them fall asleep faster and the most room for improvement. However, the results were not significant. Another set of analyses was performed with males and females separately. No sleep improvement was found for men or for women.

Sleep Measured by Daily Self-Report

Analyses of the daily self-report data found that the test product helped participants feel that they experienced better sleep. Participants felt sleepier at bedtime, going from 59.73 before product use to 65.93 during product use on a 0-100 scale (p<0.001; 10.38% increase). They perceived fewer nighttime awakenings after falling asleep, going from 2.95 before product use to 2.27 during product use (p<0.001; 23.05% decrease). They also reported getting out of bed fewer times, from 1.13 before product use to 0.97 during product use (p=0.01; 14.16% decrease). In addition, participants reported a 23.19% improvement in feeling well-rested

TABLE 3

Objective sleep and multilevel regression results comparing nights before product use to nights during product use for n = 28 (n = 926 nights).

|  | Observed | | Estimated | | |
| --- | --- | --- | --- | --- | --- |
|  | Pre-test Period | Product Use | Constant | beta | p-value |
| SleepScore (0-100) | 77.96 | 77.32 | 77.99 | -0.552 | 0.190 |
| BodyScore (0-100) | 75.74 | 76.03 | 75.73 | 0.419 | 0.272 |
| MindScore (0-100) | 77.40 | 77.17 | 77.45 | 0.067 | 0.469 |
| Total Sleep Time (minutes) | 400.60 | 393.74 | 400.85 | -5.520 | 0.101 |
| Sleep Onset Latency (minutes) | 23.56 | 26.40 | 23.64 | 2.748 | 0.021 |
| Number of Awakenings | 4.86 | 4.92 | 4.87 | 0.038 | 0.396 |
| Wake After Sleep Onset (minutes) | 45.03 | 46.85 | 44.88 | 1.903 | 0.175 |
| Time in Bed (minutes) | 475.24 | 473.31 | 475.29 | -0.077 | 0.493 |
| Sleep Efficiency | 84.39 | 83.34 | 84.34 | -0.887 | 0.029 |
| Sleep Maintenance | 84.50 | 83.64 | 84.47 | -0.773 | 0.047 |
| Light (minutes) | 250.11 | 246.71 | 250.28 | -2.883 | 0.202 |
| REM (minutes) | 77.50 | 74.69 | 77.71 | -2.503 | 0.086 |
| Deep (minutes) | 72.99 | 72.34 | 72.86 | -0.072 | 0.483 |
| % Light Sleep | 56% | 55% | 56% | -0.192 | 0.342 |
| % REM Sleep | 17% | 17% | 17% | -0.466 | 0.100 |
| % Deep Sleep | 17% | 17% | 17% | 0.110 | 0.393 |
| % Wake After Sleep Onset | 10% | 11% | 10% | 0.541 | 0.091 |

In Table 3, for pre-test period and the product use period, each average was calculated by averaging nights across participants, and then averaging those participants' averages to a single simple average, listed under "Observed" in Table 3. Listed under "Estimated" are the outcomes of the multilevel regression analyses. Regression model was as follows: Sleepmeasure$_{ij}$=Const0$_{ij}$+B*TestPeriod$_{ij}$; TestPeriod coded in the morning (p<0.001), with an average rating of 49.60 before product use and a rating of 61.10 during product use on a 0-100 scale. Finally, participants reported a 18.31% increase in overall sleep quality (p<0.001), going from an average of 54.30 before product use to 64.24 during product use on a 0-100 scale. However, there was no significant change for daily self-reported sleep onset. See Table 4.

TABLE 4

Self-report daily questionnaire and multilevel regression results comparing nights before product use to nights during product use for n = 28 (n = 982 nights).

| | Observed | | Estimated | | |
|---|---|---|---|---|---|
| | Pre-test Period | Product Use | Constant | beta | p-value |
| Bedtime Sleepiness (0-100) | 59.73 | 65.93 | 60.02 | 5.684 | <0.001 |
| Sleep Onset Latency (minutes) | 33.51 | 32.98 | 33.25 | −0.137 | 0.472 |
| Number of Awakenings | 2.95 | 2.27 | 2.90 | −0.621 | <0.001 |
| Number of Times Ou tof Bed | 1.13 | 0.97 | 1.11 | −0.133 | 0.010 |
| Well-rested in the Morning (0-100) | 49.60 | 61.10 | 49.91 | 11.095 | <0.001 |
| Sleep Quality (0-100) | 54.30 | 64.24 | 54.79 | 9.044 | <0.001 |

In Table 4, for pre-test period and the product use period, each average was calculated by averaging nights across participants, and then averaging those participants' averages to a single simple average, listed under "Observed" in Table 4. Listed under "Estimated" are the outcomes of the multilevel regression analyses. Regression model was as follows: Sleepmeasure$_{ij}$=Const$_{0ij}$+B*TestPeriod$_{ij}$; TestPeriod coded as 0 for the observations during nights when participants were not using the test product, and 1 for nights when participants reported using the test product. Nights during the product use period in which participants did not report using the product were not included in analyses.

Sleep Measured by Sleep Experience Questionnaires

The results of the daily questionnaires were confirmed by significant sleep improvements that were observed when comparing the sleep experience questionnaires. The first of these sleep experience questionnaires was completed before the product use period, the second was completed after 1 week of product use, and the third was completed at the end of the study (after 3 weeks of product use).

Figure 17:
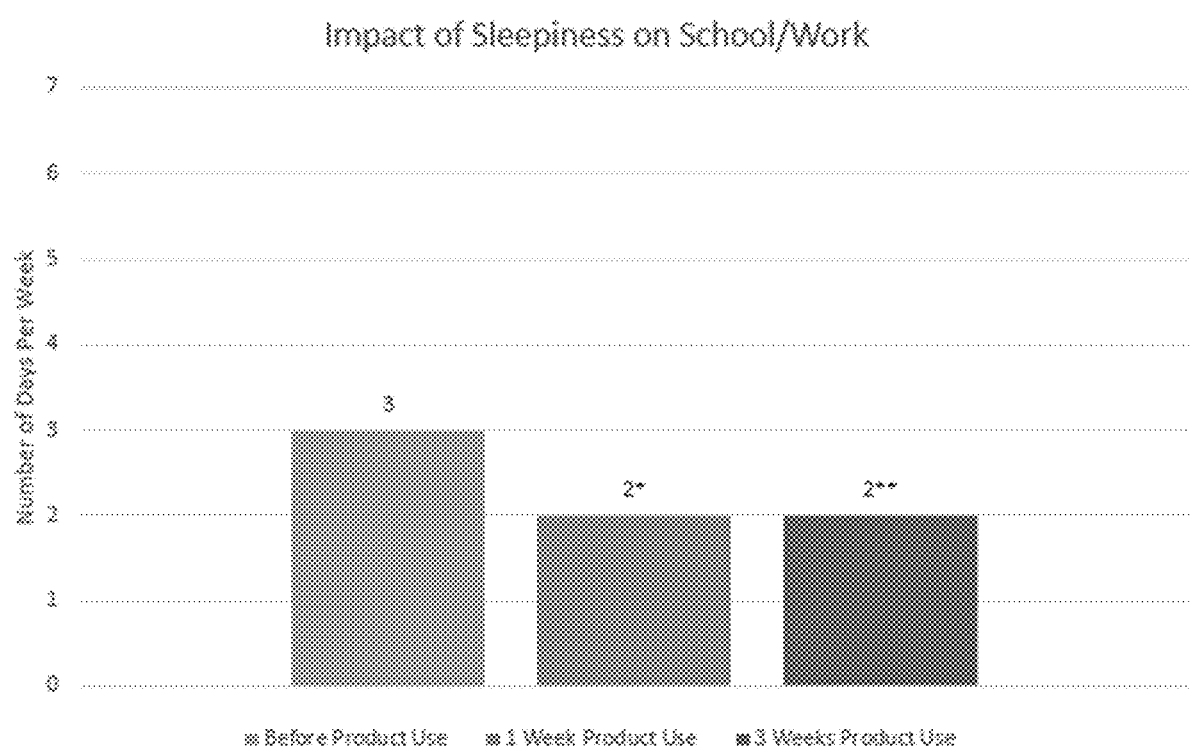
FIG. 17 is a graph reporting example data on self-reported average number of days per week participants felt so sleepy/tired that it affected them at school/work or in their private life. Note: * indicates significant at $p<0.05$ after 1 week of use. ** indicates significant at $p<0.05$ after 3 weeks of use.

First, to test for a 1-week effect, we compared participants' perceptions after 1 week of using the product to the time before using the product. There was a significant reduction in how many days feeling sleepy or tired affected school, work, or private life (see FIG. 17. No significant changes were found for how many minutes it took to fall asleep or other aspects of perceived sleep.

Figure 18:
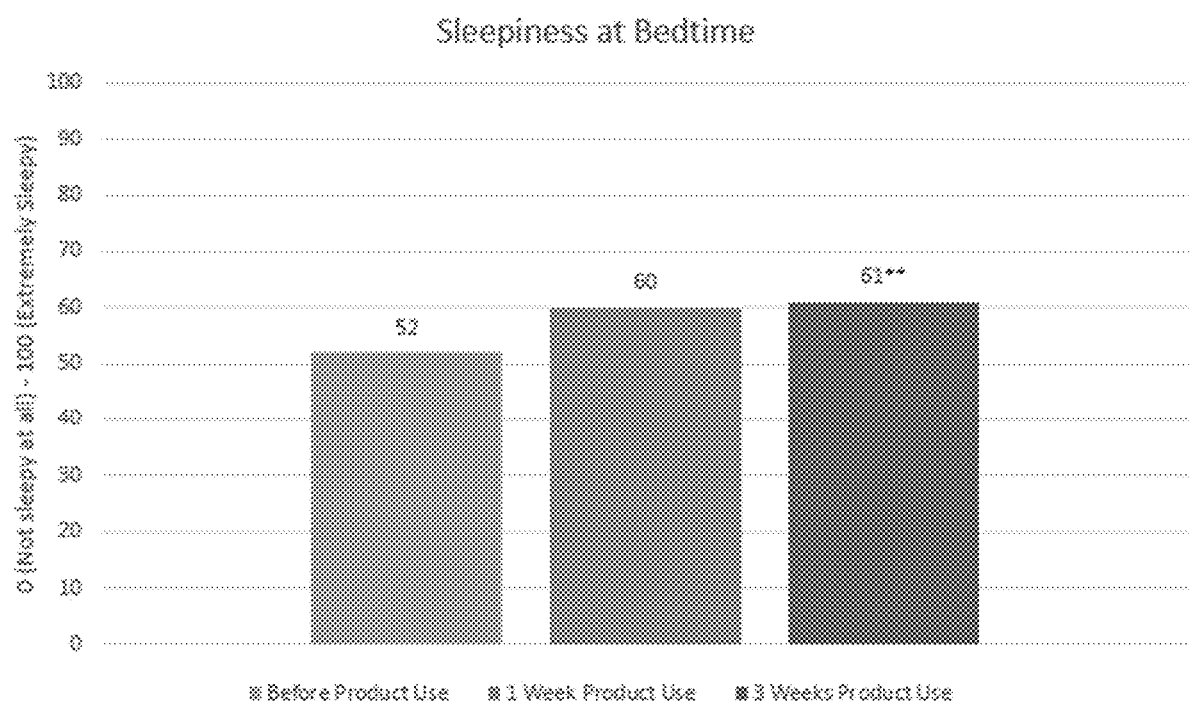
FIG. 18 is a graph reporting example data on self-reported average sleepiness of participants at bedtime. Note: ** indicates significant at $p<0.05$ after 3 weeks of use.
Figure 19:
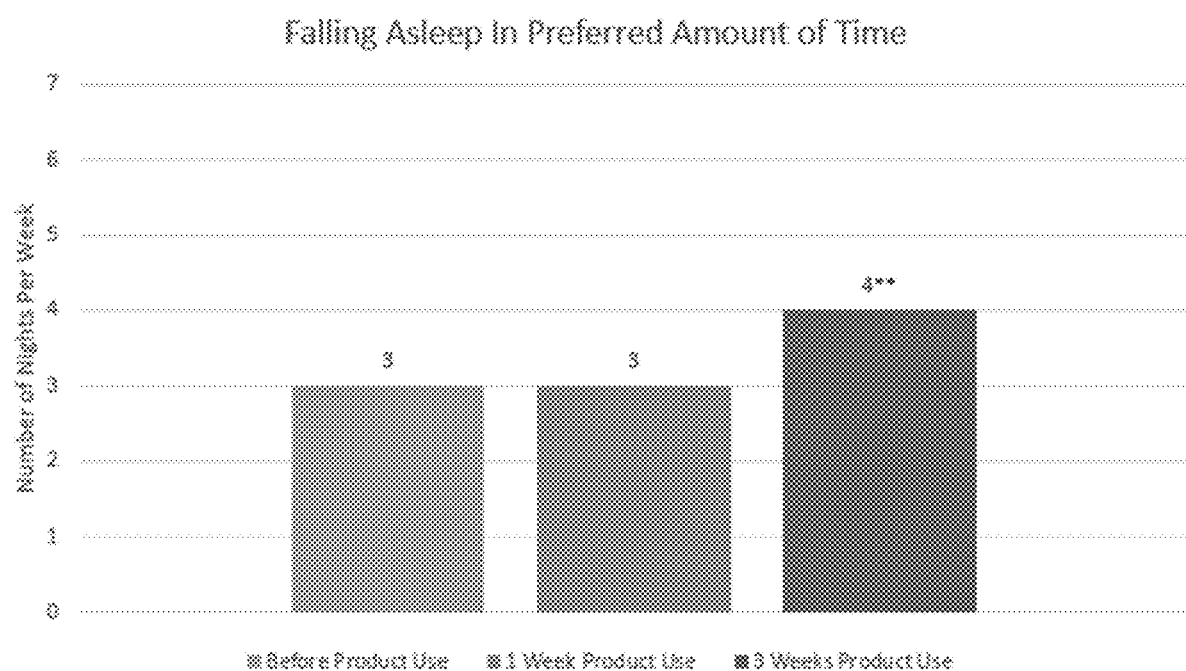
FIG. 19 is a graph reporting example data on self-reported average number of nights per week participants reported falling asleep in the amount of time that they preferred. Note: ** indicates significant at $p<0.05$ after 3 weeks of use.
Figure 20:
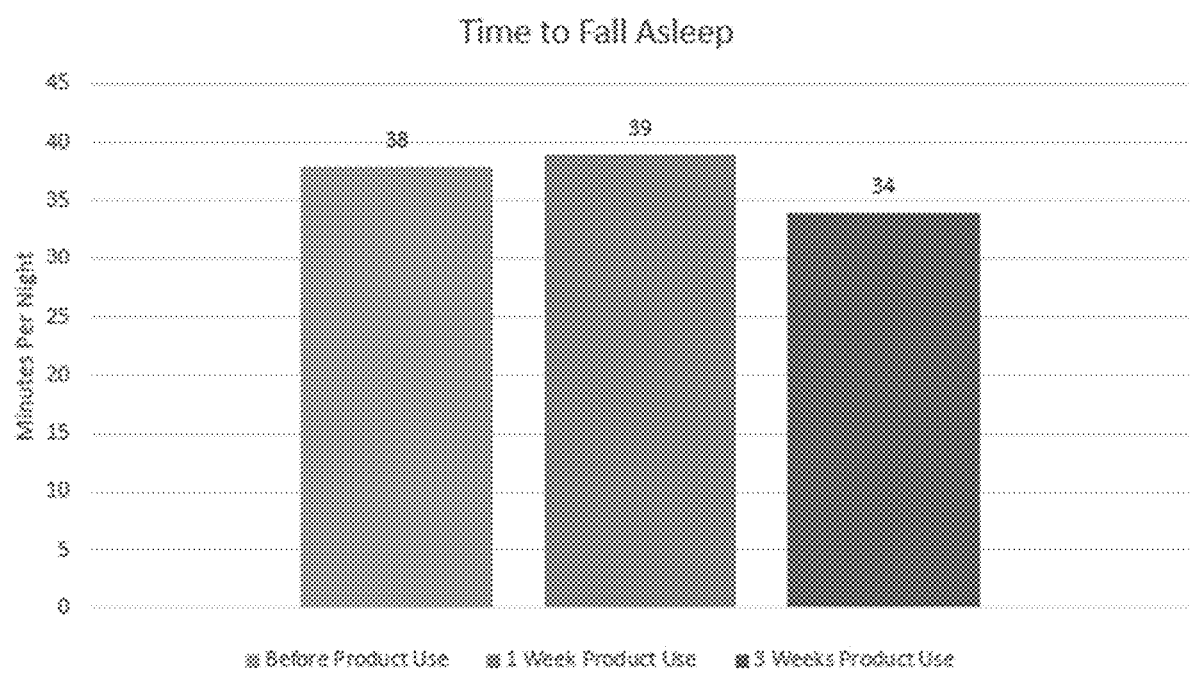
FIG. 20 is a graph reporting example data on self-reported average number of minutes it took to fall asleep per night.
Figure 21:
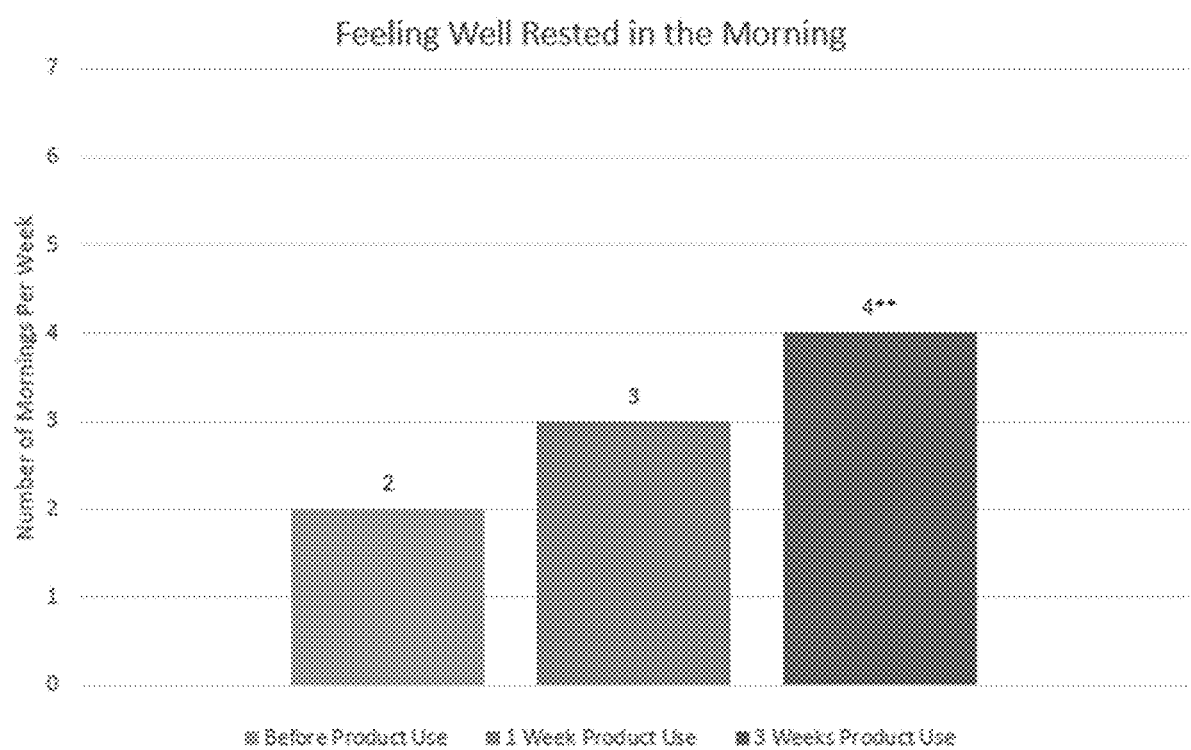
FIG. 21 is a graph reporting example data on self-reported average number of mornings per week participants woke up feeling well rested. Note: ** indicates significant at $p<0.05$ after 3 weeks of use.
Figure 22:
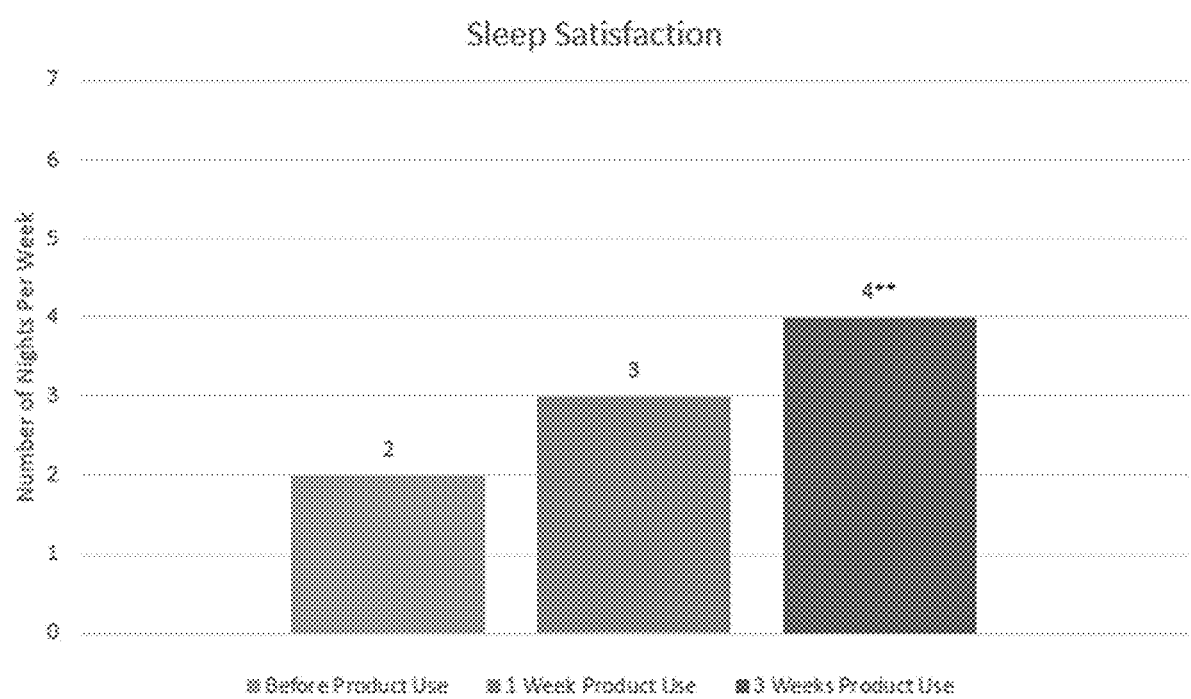
FIG. 22 is a graph reporting example data on self-reported average number of nights per week participants felt satisfied with their sleep. Note: ** indicates significant at $p<0.05$ after 3 weeks of use.

Next, to test for a 3-week effect, participants' perceptions at the end of the study were compared to the time before using the product. Similar to the aforementioned 1-week effect, there was a reduction in how many days feeling sleepy or tired affected participants' school, work, or private life (see FIG. 17). Participants reported improvements in sleepiness at bedtime (FIG. 18) and how many days per week they were able to fall asleep in their preferred amount of time (see FIG. 19), even though there was no significant change in how many minutes on average they reported it took to fall asleep (FIG. 20). In addition, there were significant improvements in feeling rested upon waking in the morning (see FIG. 21) and feeling satisfied with sleep (FIG. 22).

Discussion

This validation study evaluated the effectiveness of a product combining THC with CBN to help with falling asleep. Medical *Cannabis* patients certified by the Maryland Medical *Cannabis* Commission who felt they had trouble falling asleep were recruited by Curio Wellness into the study. The research participants tracked their sleep for 3 weeks and then tested the product for 3 weeks in their own homes while continuing to track their sleep. This way of testing has the advantage of providing insight into the effectiveness of the product under real-life conditions and hence yielding more ecologically valid results.

SleepScore Max® was used to measure objective sleep, and self-report questionnaires were used to measure perceived sleep. In addition to brief daily questionnaires that were sent each morning of the study to measure compliance and sleep experiences, participants completed 3 longer surveys assessing perceived sleep and user experiences.

Across the 28 participants with consistent objective sleep data, there were 481 nights of tracked sleep before test product use and 445 nights during which they tracked their sleep and reported using the test product (overall, 76% compliance rate for both activities during product use).

Participants were recruited into the study based on self-reported difficulty falling asleep. Before using the product, they reported taking 38 minutes to fall asleep on average. However, objective sleep data collected before product use showed that they actually were taking only 24 minutes to fall asleep on average. Taking less than 30 minutes to fall asleep is considered normal in the scientific and clinical sleep literature (Edinger et al., 2004; Ohayon et al., 2017). In the current sample, during the period before using the product, on only 22% of nights did the participants take 30 or more minutes to fall asleep. Therefore, it appears that there may have been little room for improvement in objective sleep onset in this sample.

Analysis of the objective sleep data indicated that the test product was unexpectedly associated with a statistically significant increase in how long it took to fall asleep. Participants' average onset time rose from 24 minutes before product use to 26 minutes during product use. The objective data also revealed that taking longer to fall asleep impacted sleep efficiency, meaning that participants spent less time asleep while they were in bed. Also, their ability to stay asleep was slightly negatively affected, as indicated by a decrease in sleep maintenance.

Mirroring the objective data, the self-report data did not show statistically significant improvement in how many minutes participants felt it took them to fall asleep. Perceived sleep onset did not change significantly across the daily questionnaires or the three sleep experience questionnaires. However, at the end of the study there was significant improvement in how often participants felt that they fell asleep within their preferred amount of time, going from an average of 3 nights per week to 4 nights per week.

Despite the lack of improvement in falling asleep faster, participants reported that the product helped their sleep in many other ways. At the end of the study, they felt sleepier at bedtime, felt more rested in the morning, and were more satisfied with their sleep, compared to the weeks before using the test product. They also felt they woke up less often and got out of bed less often during the night. In addition, participants reported a significant decrease in how often feelings of sleepiness affected their school, work, or private life.

When interpreting the study results, it must be considered that the timing of this study unexpectedly coincided with the COVID-19 pandemic. Given that the study design did not include a control group, the extent to which the effects were caused by the *Cannabis* test product versus health and lifestyle changes associated with the COVID-19 pandemic cannot be fully known. Data collection occurred from March 23-May 3, 2020. Maryland's stay-at-home directive was ordered on Mar. 30, 2020 (Wenger & Wood, 2020), but closures of non-essential business, school closings, and other restrictions began earlier (Dance, 2020).

REFERENCES

Watson N F, Badr M S, Belenky G, et al.; Consensus Conference Panel. Joint consensus statement of the American Academy of Sleep Medicine and Sleep Research Society on the recommended amount of sleep for a healthy adult: methodology and discussion. *Sleep*. 2015 Aug. 1; 38(8):1161-83.

Liu Y, Wheaton A G, Chapman D P, et al. Prevalence of healthy sleep duration among adults United States, 2014. MMWR Morb Mortal Wkly Rep. 2016 Feb. 19; 65(6): 137-41.

NHLBI (National Heart, Lung, and Blood Institute). National Sleep Disorders Research Plan, 2003. Bethesda, MD: National Institutes of Health; 2003.

Altman, B. R., Mian, M. N., Slavin, M., & Earleywine, M. (2019). *Cannabis* expectancies for sleep. Journal of Psychoactive Drugs, 51(5), 405-412. https://doi.org/10.1080/02791072.2019.1643053.

Babson, K. A., Sottile, J., & Morabito, D. (2017). *Cannabis*, cannabinoids, and sleep: A review of the literature. Current Psychiatry Reports, 19(4), 23. https://doi.org/10.1007/s11920-017-0775-9.

Barratt, E. S., Beaver, W., & White, R. (1974). The effects of marijuana on human sleep patterns. Biological Psychiatry, 8(1), 47-54.

Bowles, N. P., Herzig, M. X., & Shea, S. A. (2017). Recent legalization of *Cannabis* use: Effects on sleep, health, and workplace safety. Nature and Science of Sleep, 9, 249-251. https://doi.org/10.2147/NSS.S152231

Chait, L. D. (1990). Subjective and behavioral effects of marijuana the morning after smoking. Psychopharmacology, 100(3), 328-333. https://doi.org/10.1007/BF02244601

Cousens, K., & DiMascio, A. (1973). (−) Delta 9 THC as an hypnotic: An experimental study of three dose levels. Psychopharmacologia, 33(4), 355-364. https://doi.org/10.1007/BF00437513

Dance, S. (2020, March 24). Even without 'shelter in place' order, Maryland faces some of nation's strictest orders to contain coronavirus. The Baltimore Sun. Retrieved from https://www.baltimoresun.com Feinberg, I., Jones, R., Walker, J. M., Cavness, C., & March, J. (1975). Effects of high dosage delta-9-tetrahydrocannabinol on sleep patterns in man. Clinical Pharmacology & Therapeutics, 17(4), 458-66. https://doi.org/10.1002/cpt1975174458

Gates, P. J., Albertella, L., & Copeland, J. (2014). The effects of cannabinoid administration on sleep: A systematic review of human studies. Sleep Medicine Reviews, 18, 477-487. https://doi.org/10.1016/j.smrv.2014.02.005

National Conference of State Legislatures. (2020, March 10). State Medical Marijuana Laws. http://www.ncsl.org/research/health/state-medical-marijuana-laws.aspx O'Hare, E., Flanagan, D., Penzel, T., Garcia, C., Frohberg, D., & Heneghan, C. (2014). A comparison of radiofrequency biomotion sensors and actigraphy versus polysomnography for the assessment of sleep in normal subjects. Sleep and Breathing, 19(1), 91-98. https://doi.org/10.1007/s11325-014-0967-z Ohayon M. M., Carskadon M. A., Guilleminault, C., & Vitiello M. V. (2004) Meta-analysis of quantitative sleep parameters from childhood to old age in healthy individuals: Developing normative sleep values across the human lifespan. Sleep, 27(7), 1255-1273.

Ohayon, M., Wickwire, E. M., Hirshkowitz, M., Albert, S. M., Avidan, A., Daly, F. J., et al. (2017). National Sleep Foundation's sleep quality recommendations: First report. Sleep Health, 3(1), 6-19. doi: 10.1016/j.sleh.2016.11.006

Piper, B. J., DeKeuster, R. M., Beals, M. L., Cobb, C. M., Burchman, C. A., Perkinson, L., Lynn, S. T., Nichols, S. D. & Abess, A. T. (2017). Substitution of medical *Cannabis* for pharmaceutical agents for pain, anxiety, and sleep. Journal of Psychopharmacology, 31(5), 569-575. doi: 10.1177/0269881117699616

Russo, E. B. (2011). Taming THC: Potential *Cannabis* synergy and phytocannabinoid-terpenoid entourage effects. British Journal of Pharmacology, 163(7), 1344-1364. https://doi.org/10.1111/j.1476-5381.2011.01238.x Schade, M. M., Bauer, C. E., Murray, B. R., Gahan, L., Doheny, E. P., Kilroy, H., Zaffaroni, A., & Montgomery-Downs, H. E. (2019). Sleep validity of a non-contact bedside movement and respiration-sensing device. Journal of Clinical Sleep Medicine, 15(7), 1051-61. https://doi.org/10.5664/jcsm.7892

SleepScore Labs. (2020, April 22). Are We Getting More Sleep During COVID-19 Restrictions? Effects of THC combined with CBN on staying asleep. https://www.sleepscore.com/category/trouble-staying-asleep/?rfr=ssl-top-nav SleepScore Labs. (2020, May 15). Effects of THC combined with CBN on staying asleep. https://www.sleepscore.com/category/trouble-staying-asleep/?rfr=ssl-top-nav Wenger, Y., & Wood, P. (2020, March 30). Gov. Hogan issues stay-at-home order for Maryland to stop spread of the coronavirus. The Baltimore Sun. Retrieved from https://www.baltimoresun.com Yoshida, H., Usami, N., Ohishi, Y., Watanabe, K., Yamamoto, I., & Yoshimura, H. (1995). Synthesis and pharmacological effects in mice of halogenated cannabinol derivatives. Chemical and Pharmaceutical Bulletin, 43(2), 335-337. https://doi.org/10.1248/cpb.43.335

Zaffaroni, A., Coffey, S., Dodd, S., Kilroy, H., Lyon, G., O'Rourke, D., Lederer, K., Fietze, I., & Penzel, T. (2019). Sleep staging monitoring based on sonar smartphone technology. 41st Annual International Conference of the IEEE Engineering in Medicine and Biology Society (EMBC) (pp. 2230-2233). Berlin: IEEE. doi: 10.1109/EMBC.2019.8857033

Zaffaroni, A., Doheny, E. P., Gahan, L., Ivanov, Y., Kilroy, H., O'Mahony, N, & O'Rourke, D. (2017). Non-contact estimation of sleep staging. In H. Eskola, O. Väisänen, J. Viik, & J. Hyttinen (Eds.), EMBEC & NBC 2017.

EMBEC 2017, NBC 2017. IFMBE Proceedings, 65. Singapore: Springer. https://doi.org/10.1007/978-981-10-5122-7_20

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative (e.g., "or") herein is taken to mean either one or both or any combination thereof of the alternatives. The term "and/or" used herein is to be taken mean specific disclosure of each of the specified features or components with or without the other. For example, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. When particular values or compositions are provided in the instant disclosure, unless otherwise stated, the meaning of "about" or "approximately" should be assumed to be within an acceptable error range for that particular value or composition.

The term "administering", "administered" and grammatical variants refers to the physical introduction of an agent to a subject, using any of the various methods and delivery systems known to those skilled in the art. Exemplary routes of administration include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Non-parenteral routes include oral, topical, epidermal or mucosal route of administration, for example, intranasally, vaginally, rectally, sublingually or topically. Administering can also be performed, for example, once, a plurality of times, and/or over one or more extended periods.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

The above disclosure contains various examples of oral pulse-release compositions and dosage forms, and methods of treating sleep disorders in a subject by administering the oral pulse-release compositions and dosage forms. Aspects of these various examples may all be combined with one another, even if not expressly combined in the present disclosure, unless they are clearly mutually exclusive.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

What is claimed is:

1. A method of treating a sleep disorder in a subject in need thereof, the method comprising:
    administering to the subject an oral pulse-release dosage form comprising a total daily dose of a first cannabinoid active pharmaceutical ingredient ($API_1$) and a total daily dose of a second cannabinoid API ($API_2$), wherein the oral pulse-release dosage form comprises:
    a first pulse-release component ($C_1$) comprising a first portion ($P_1$) of the first cannabinoid API ($API_1P_1$) and a first portion ($P_1$) of the second cannabinoid API ($API_2P_1$); and
    at least a second pulse-release component ($C_2$) comprising a second portion ($P_2$) of the first cannabinoid API ($API_1P_2$) and a second portion ($P_2$) of the second cannabinoid API ($API_2P_2$);
        wherein the total daily dose of each of the APIs and the $API_2$ is divided between the first portion ($P_1$) in the first pulse-release component ($C_1$) and at least the second portion ($P_2$) in the at least second pulse-release component ($C_2$); and
        wherein when the pulse-release dosage form is placed in an aqueous solution of 0.1N HCl pH 1.1 for 2 hours followed by 8 hours in sodium phosphate buffer at pH 6.8, at 37° C.±0.5° C.,
        the pulse-release dosage form provides release of the $API_1P_2$ and the $API_2P_2$ beginning from 2 to 6 hours after release of the $API_1P_1$ and the $API_2P_1$ begins
    wherein:
        the first cannabinoid API ($API_1$) is delta-9-tetrahydrocannabinol (THC) and the second cannabinoid API ($API_2$) is cannabinol (CBN);
        the first pulse-release component ($C_1$) is an immediate release (IR) formulation of the first cannabinoid API ($API_1$) and the second cannabinoid API ($API_2$);
        the second pulse-release component ($C_2$) is a delayed release (DR) formulation of the first cannabinoid API ($API_1$) and the second cannabinoid API ($API_2$); and
    for each API, the first portion ($P_1$) is independently selected from 25% to 75% of the total daily dose, and for each API the second portion ($P_2$) is independently selected from 25% to 75% of the total daily dose.

2. The method of claim 1, wherein:
    the administering results in an increase in the subject's total sleeping time during the night.

3. The method of claim 1, wherein:
the administering results in an increase in the subject's total light sleeping time during the night.

4. The method of claim 1, wherein:
the administering results in an increase in the subject's light sleeping time as a proportion of total sleeping time during the night.

5. The method of claim 1, wherein:
the administering results in an increase in the subject's total time in bed during the night.

6. The method of claim 1, wherein:
the administering results in an increase in the subject's total sleeping time during the night, an increase in the subject's total light sleeping time during the night, an increase in the subject's light sleeping time as a proportion of total sleeping time during the night, an increase in the subject's total time in bed during the night, or any combination thereof, as measured by a validated sleep monitoring device.

7. The method of claim 1, wherein the administering results in:
the subject experiencing an increase in one or more of:
feeling well rested in the morning and/or during the day;
perceived sleep quality;
perceived total sleep time during the night; or
sleep satisfaction; and/or
the subject experiencing a decrease in one or more of:
perceived frequency of awakenings during the night;
number of times out of bed at night;
number of naps during the day; or
perceived time awake at night.

8. The method of claim 1, wherein:
the sleep disorder comprises insomnia, wherein the insomnia is primarily characterized by an inability to stay asleep during the night.

9. The method of claim 8, wherein the insomnia is characterized using a validated sleep monitoring device.

10. The method of claim 8, wherein characterization of the sleep disorder is reported by the subject.

11. The method of claim 1, wherein the administering does not result in:
a decrease in latency to sleep onset;
an alteration of time in deep sleep and/or REM sleep; and/or
a hangover effect during the day after the administering.

12. The method of claim 1, wherein the subject has previously been administered with one or more cannabinoids for treating a medical condition.

13. The method of claim 1, wherein the administering is up to 30 minutes, 1 hour, or 2 hours before the subject intends to begin sleeping at night.

14. The method of claim 1, wherein the pulse-release dosage form provides a second time of peak release rate ($PRR_2$) of each of the APIs ($PRR_2API_1$) and the $API_2$ ($PRR_2API_2$) from about 2 to 6 hours after a first time of peak release rate ($PRR_1$).

15. The method of claim 14, wherein the $PRR_1$ is after 1-2 hours.

16. The method of claim 1, wherein the total daily dose of the THC is from 1 mg to 40 mg and the total daily dose of the CBN is from 2.5 mg to 100 mg.

17. The method of claim 1, wherein the total daily dose of the THC is selected from: at least 1 mg, at least 2 mg, at least 3 mg, at least 4 mg, at least 5 mg, at least 6 mg, at least 8 mg, at least 10 mg, at least 15 mg, at least 20 mg, at least 25 mg, at least 30 mg, and at least 35 mg, and the total daily dose of the CBN is selected from: at least 2.5 mg, at least 3 mg, at least 4 mg, at least 5 mg, at least 15 mg, at least 20 mg, at least 25 mg, at least 30 mg, at least 35 mg, and at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

18. The method of claim 1, wherein:
the first pulse-release component ($C_1$) comprises:
the first portion ($P_1$) of the first cannabinoid API ($API_1P_1$) and the first portion ($P_1$) of the second cannabinoid API ($API_2P_1$);
one or more binders;
one or more disintegrants;
one or more lubricants; and
one or more flow aids; and
the second pulse-release component ($C_2$) comprises:
the second portion ($P_2$) of the first cannabinoid API ($API_1P_2$) and the second portion ($P_2$) of the second cannabinoid API ($API_2P_2$);
one or more binders;
one or more lubricants; and
one or more flow aids;
wherein the second pulse-release component is coated with a delayed-release layer comprising one or more pH-dependent and/or non-pH-dependent polymers, and optionally one or more plasticizers, one or more pore formers, and/or one or lubricants.

19. The method of claim 18, wherein:
in the first pulse-release component ($C_1$), the second pulse-release component ($C_2$), or both, when present:
the binders comprise from 1 to 60% (w/w);
the disintegrants comprise from 0.05 to 15% (w/w);
the lubricants comprise from 0.5 to 5 (w/w);
the flow aids comprise from 0.05 to 0.5 (w/w); and
the pH-dependent and/or non-pH-dependent polymers comprise from 0.5 to 35% (w/w).

20. The method of claim 1, wherein:
the first pulse-release component ($C_1$) comprises:
from 0.5 mg to 30 mg of the first cannabinoid active pharmaceutical ingredient ($API_1$);
from 1.25 mg to 75 mg of the second cannabinoid active pharmaceutical ingredient; and
microcrystalline cellulose, hydroxypropylmethylcellulose, and magnesium stearate; and
the second pulse-release component ($C_2$) comprises:
from 0.5 mg to 30 mg of the first cannabinoid active pharmaceutical ingredient ($API_1$);
from 1.25 mg to 75 mg of the second cannabinoid active pharmaceutical ingredient; and
microcrystalline cellulose, methacrylic acid copolymer, magnesium stearate, and colloidal silicone dioxide.

21. A method of treating a sleep disorder in a subject in need thereof, the method comprising:
administering to the subject an oral pulse-release dosage form comprising a total daily dose of a first cannabinoid active pharmaceutical ingredient ($API_1$) and a total daily dose of a second cannabinoid API ($API_2$), wherein the pulse-release dosage form comprises:
a first pulse-release component ($C_1$) comprising a first portion ($P_1$) of the first cannabinoid API ($API_1P_1$) and a first portion ($P_1$) of the second cannabinoid API ($API_2P_1$);
a second pulse-release component ($C_2$) comprising a second portion ($P_2$) of the first cannabinoid API ($API_1P_2$) and a second portion ($P_2$) of the second cannabinoid API ($API_2P_2$); and at least a third pulse-release component ($C_3$) comprising a third portion ($P_3$) of the first cannabinoid API ($API_1P_3$) and a third portion ($P_3$) of the second cannabinoid API ($API_2P_2$);

wherein the total daily dose of each of the APIs and the $API_2$ is divided between the first portion ($P_1$) in the first pulse-release component ($C_1$), the second portion ($P_2$) in the second pulse-release component ($C_2$), and at least the third portion ($P_3$) in the at least third pulse-release component ($C_3$); and wherein when the pulse-release dosage form is placed in an aqueous solution of 0.1N HCl pH 1.1 for 2 hours followed by 8 hours in sodium phosphate buffer at pH 6.8, at 37° C.±0.5° C., the pulse-release dosage form provides release of the $API_1P_2$ and the $API_2P_2$ beginning from 1 to 4 hours after release of the $API_1P_1$ and the $API_2P_1$ begins, and release of the $API_1P_3$ and the $API_2P_3$ beginning from 1 to 4 hours after release of the $API_1P_2$ and the $API_2P_2$ begins wherein:
the first cannabinoid API ($API_1$) is delta-9-tetrahydrocannabinol (THC) and the second cannabinoid API ($API_2$) is cannabinol (CBN);
the first pulse-release component ($C_1$) is an immediate release (IR) formulation of the first cannabinoid API ($API_1$) and the second cannabinoid API ($API_2$);
the second pulse-release component ($C_2$) is a delayed release (DR) formulation of the first cannabinoid API ($API_1$) and the second cannabinoid API ($API_2$); and
the third pulse-release component ($C_3$) is a delayed release (DR) formulation of the first cannabinoid API ($API_1$) and the second cannabinoid API ($API_2$); and
for each API, the first portion ($P_1$) is independently selected from 25% to 75% of the total daily dose, for each API, the second portion ($P_2$) is independently selected from 25% to 75% of the total daily dose, and, for each API, the third portion ($P_3$) is independently selected from 25% to 75% of the total daily dose.

22. The method of claim 21, wherein:
the administering results in an increase in the subject's total sleeping time during the night.

23. The method of claim 21, wherein:
the administering results in an increase in the subject's total light sleeping time during the night.

24. The method of claim 21, wherein:
the administering results in an increase in the subject's light sleeping time as a proportion of total sleeping time during the night.

25. The method of claim 21, wherein:
the administering results in an increase in the subject's total time in bed during the night.

26. The method of claim 21, wherein:
the administering results in an increase in the subject's total sleeping time during the night, an increase in the subject's total light sleeping time during the night, an increase in the subject's light sleeping time as a proportion of total sleeping time during the night, an increase in the subject's total time in bed during the night, or any combination thereof, as measured by a validated sleep monitoring device.

27. The method of claim 21, wherein the administering results in:
the subject experiencing an increase in one or more of:
feeling well rested in the morning and/or during the day;
perceived sleep quality;
perceived total sleep time during the night; or
sleep satisfaction; and/or
the subject experiencing a decrease in one or more of:
perceived frequency of awakenings during the night;
number of times out of bed at night;
number of naps during the day; or
perceived time awake at night.

28. The method of claim 21, wherein:
the sleep disorder comprises insomnia, wherein the insomnia is primarily characterized by an inability to stay asleep during the night.

29. The method of claim 28, wherein the insomnia is characterized using a validated sleep monitoring device.

30. The method of claim 28, wherein characterization of the sleep disorder is reported by the subject.

31. The method of claim 21, wherein the administering does not result in:
a decrease in latency to sleep onset;
an alteration of time in deep sleep and/or REM sleep; and/or
a hangover effect during the day after the administering.

32. The method of claim 21, wherein the subject has previously been administered with one or more cannabinoids for treating a medical condition.

33. The method of claim 21, wherein the administering is up to 30 minutes, 1 hour, or 2 hours before the subject intends to begin sleeping at night.

34. The method of claim 21, wherein:
the pulse-release dosage form provides a second time of peak release rate ($PRR_2$) of each of the APIs ($PRR_2API_1$) and the $API_2$ ($PRR_2API_2$) from about 1 to 4 hours after a first PRR ($PRR_1$) and a third time of peak release rate ($PRR_3$) of each of the APIs ($PRR_3API_1$) and the $API_2$ ($PRR_3API_2$) from about 1 to 4 hours after the second time of PRR ($PRR_2$).

35. The method of claim 34, wherein:
the $PRR_1$ is after 1-2 hours.

36. The method of claim 21, wherein:
the total daily dose of the THC is from 10 mg to 40 mg and the total daily dose of the CBN is from 5 mg to 100 mg.

37. The method of claim 21, wherein:
the total daily dose of the THC is selected from: at least 10 mg, at least 15 mg, at least 20 mg, at least 25 mg, at least 30 mg, and at least 35 mg, and the total daily dose of the CBN is selected from: at least 5 mg, at least 10 mg, at least 15 mg, at least 20 mg, at least 25 mg, at least 30 mg, at least 35 mg, and at least 40 mg, at least 45 mg, at least 50 mg, at least 55 mg, at least 60 mg, at least 65 mg, at least 70 mg, at least 75 mg, at least 80 mg, at least 85 mg, at least 90 mg, and at least 95 mg.

38. The method of claim 21, wherein:
the first pulse-release component ($C_1$) comprises:
the first portion ($P_1$) of the first cannabinoid API ($API_1P_1$) and the first portion ($P_1$) of the second cannabinoid API ($API_2P_1$);
one or more binders;
one or more disintegrants;
one or more lubricants; and
one or more flow aids; and the second pulse-release component ($C_2$) comprises:
- the second portion ($P_2$) of the first cannabinoid API ($API_1P_2$) and the second portion ($P_2$) of the second cannabinoid API ($API_2P_2$);
- one or more binders;
- one or more lubricants;
- one or more flow aids; and
- wherein the second pulse-release component is coated with a first delayed-release layer comprising one or more pH-dependent and/or non-pH-dependent polymers, and optionally one or more plasticizers, one or more pore formers, and/or one or lubricants; and the third pulse-release component ($C_3$) comprises:
- the third portion ($P_3$) of the first cannabinoid API ($API_1P_3$) and the third portion ($P_3$) of the second cannabinoid API ($API_2P_3$);
- one or more binders;
- one or more lubricants; and
- one or more flow aids; and
- wherein the third pulse-release component is coated with a second delayed-release layer comprising one or more pH-dependent and/or non-pH-dependent polymers, and optionally one or more plasticizers, one or more pore formers, and/or one or lubricants.

39. The method of claim 38, wherein, in the first pulse-release component ($C_1$), the second pulse-release component ($C_2$), and/or the third pulse-release component ($C_3$), when present:
- the binders comprise from 1 to 60% (w/w);
- the disintegrants comprise from 0.05 to 15% (w/w);
- the lubricants comprise from 0.5 to 5 (w/w);
- the flow aids comprise from 0.05 to 0.5% (w/w); and
- the pH-dependent and/or non-pH-dependent polymers comprise from 0.5 to 35% (w/w).

40. The method of claim 21, wherein:
the first pulse-release component ($C_1$) comprises:
- from 2.5 mg to 30 mg of the first cannabinoid active pharmaceutical ingredient ($API_1$);
- from 1.25 mg to 75 mg of the second cannabinoid active pharmaceutical ingredient; and
- microcrystalline cellulose, hydroxypropylmethylcellulose, croscormellose sodium, and magnesium stearate;

the second pulse-release component ($C_2$) comprises:
- from 2.5 mg to 30 mg of the first cannabinoid active pharmaceutical ingredient ($API_1$);
- from 1.25 mg to 75 mg of the second cannabinoid active pharmaceutical ingredient; and
- microcrystalline cellulose, cellulose acetate phthalate, and magnesium stearate; and the third pulse-release component ($C_3$) comprises:
- from 2.5 mg to 30 mg of the first cannabinoid active pharmaceutical ingredient ($API_1$);
- from 1.25 mg to 75 mg of the second cannabinoid active pharmaceutical ingredient; and
- microcrystalline cellulose, methacrylic acid copolymer, and magnesium stearate.

* * * * *